(12) United States Patent
Clark et al.

(10) Patent No.: US 8,597,918 B2
(45) Date of Patent: Dec. 3, 2013

(54) PROCESS OF SEPARATING COMPONENTS OF A FERMENTATION BROTH

(75) Inventors: Warren Clark, Yale, OK (US); Michael Japs, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 545 days.

(21) Appl. No.: 12/793,623

(22) Filed: Jun. 3, 2010

(65) Prior Publication Data

US 2011/0003355 A1  Jan. 6, 2011

Related U.S. Application Data

(60) Provisional application No. 61/184,292, filed on Jun. 4, 2009.

(51) Int. Cl.
| | | |
|---|---|---|
| C12P 7/18 | (2006.01) |
| C12P 7/02 | (2006.01) |
| C12P 7/00 | (2006.01) |

(52) U.S. Cl.
USPC ............ 435/158; 435/155; 435/170; 435/132

(58) Field of Classification Search
None
See application file for complete search history.

(56) References Cited

U.S. PATENT DOCUMENTS

| | | |
|---|---|---|
| 3,976,430 A | 8/1976 | Houston et al. |
| 4,048,196 A | 9/1977 | Broecker et al. |
| 4,228,949 A | 10/1980 | Jackson |
| 4,240,578 A | 12/1980 | Jackson |
| 4,301,077 A | 11/1981 | Pesa et al. |
| 4,430,430 A | 2/1984 | Momose et al. |
| 4,652,685 A | 3/1987 | Cawse et al. |
| 4,876,331 A | 10/1989 | Doi |
| 5,164,309 A | 11/1992 | Gottschalk et al. |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,413,922 A | 5/1995 | Matsuyama et al. |
| 5,461,139 A | 10/1995 | Gonda et al. |
| 5,475,086 A | 12/1995 | Tobin et al. |
| 5,478,952 A | 12/1995 | Schwartz |
| 5,502,273 A | 3/1996 | Bright et al. |
| 5,516,883 A | 5/1996 | Hori et al. |
| 5,534,432 A | 7/1996 | Peoples et al. |
| 5,563,239 A | 10/1996 | Hubbs et al. |
| 5,602,321 A | 2/1997 | John |
| 5,608,146 A | 3/1997 | Frommer et al. |
| 5,610,041 A | 3/1997 | Somerville et al. |
| 5,650,555 A | 7/1997 | Somerville et al. |
| 5,663,063 A | 9/1997 | Peoples et al. |
| 5,674,978 A | 10/1997 | Tobin et al. |
| 5,705,626 A | 1/1998 | Tobin et al. |
| 5,747,311 A | 5/1998 | Jewell |
| 5,750,848 A | 5/1998 | Krüger et al. |
| 5,766,439 A * | 6/1998 | Eyal et al. ................. 204/524 |
| 5,770,435 A | 6/1998 | Donnelly et al. |
| 5,772,890 A * | 6/1998 | Hubred ........................ 210/638 |
| 5,830,716 A | 11/1998 | Kojima et al. |
| 5,846,740 A | 12/1998 | Tobin et al. |
| 5,849,894 A | 12/1998 | Clemente et al. |
| 5,869,301 A | 2/1999 | Nghiem et al. |
| 5,908,924 A | 6/1999 | Burdette et al. |
| 5,942,660 A | 8/1999 | Gruys et al. |
| 5,958,745 A | 9/1999 | Gruys et al. |
| 5,986,133 A * | 11/1999 | Holtzapple et al. ......... 562/608 |
| 5,994,478 A | 11/1999 | Asrar et al. |
| 5,998,366 A | 12/1999 | Tobin et al. |
| 6,010,870 A | 1/2000 | Pelzer et al. |
| 6,011,139 A | 1/2000 | Tobin et al. |
| 6,011,144 A | 1/2000 | Steinbuchel et al. |
| 6,022,729 A | 2/2000 | Steinbuchel et al. |

(Continued)

FOREIGN PATENT DOCUMENTS

| | | |
|---|---|---|
| GB | 1230276 | 4/1971 |
| GB | 1314126 | 4/1973 |
| GB | 1344557 | 1/1974 |
| GB | 1512751 | 6/1978 |
| JP | 62285779 | 12/1987 |
| KR | 10-2004-0060149 | 7/2004 |
| KR | 10-2005-0076301 | 8/2005 |
| KR | 10-2005-0076317 | 8/2005 |
| KR | 10-2005-0076348 | 8/2005 |
| KR | 10-2006-0026599 | 3/2006 |

(Continued)

OTHER PUBLICATIONS

Yavorsky, D et al "The clarification of bioreactor cell cultures for biopharmaceuticals" Pharmacology Technology 2003 62-76.*
Schaep, J "Modelling the retention of ionic components for different nanofiltration membranes" Separation and Purification Technology 2001 22-23 169-179.*
ISA/US, PCT International Search Report and Written Opinion dated Aug. 30, 2010 for PCT/US2010/037329.
Branden et al., "Introduction to Protein Structure," *Garland Publishing Inc.*, New York, p. 247 (1991).

(Continued)

Primary Examiner — John S Brusca
Assistant Examiner — Gerard Lacourciere
(74) Attorney, Agent, or Firm — Jones Day

(57) ABSTRACT

A process of isolating 1,4-butanediol (1,4-BDO) from a fermentation broth includes separating a liquid fraction enriched in 1,4-BDO from a solid fraction comprising cells, removing water from said liquid fraction, removing salts from said liquid fraction, and purifying 1,4-BDO. A process for producing 1,4-BDO includes culturing a 1,4-BDO-producing microorganism in a fermentor for a sufficient period of time to produce 1,4-BDO. The 1,4-BDO-producing microorganism includes a microorganism having a 1,4-BDO pathway having one or more exogenous genes encoding a 1,4-BDO pathway enzyme and/or one or more gene disruptions. The process for producing 1,4-BDO further includes isolating 1,4-BDO.

17 Claims, 16 Drawing Sheets

(56) References Cited

U.S. PATENT DOCUMENTS

| | | |
|---|---|---|
| 6,080,562 A | 6/2000 | Byrom et al. |
| 6,091,002 A | 7/2000 | Asrar et al. |
| 6,111,658 A | 8/2000 | Tabata |
| 6,117,658 A | 9/2000 | Dennis et al. |
| 6,156,852 A | 12/2000 | Asrar et al. |
| 6,159,738 A | 12/2000 | Donnelly et al. |
| 6,204,341 B1 | 3/2001 | Asrar et al. |
| 6,228,579 B1 | 5/2001 | Zyskind et al. |
| 6,228,623 B1 | 5/2001 | Asrar et al. |
| 6,248,862 B1 | 6/2001 | Asrar et al. |
| 6,277,586 B1 | 8/2001 | Tobin et al. |
| 6,280,986 B1 | 8/2001 | Hespell et al. |
| 6,316,262 B1 | 11/2001 | Huisman et al. |
| 6,329,183 B1 | 12/2001 | Skraly et al. |
| RE37,543 E | 2/2002 | Krüger et al. |
| 6,361,983 B1 | 3/2002 | Ames |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,682,906 B1 | 1/2004 | Tobin et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,838,276 B2 | 1/2005 | Falco et al. |
| 6,897,055 B2 | 5/2005 | Möckel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,067,300 B2 | 6/2006 | Emptage et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,256,021 B2 | 8/2007 | Hermann |
| 7,309,597 B2 | 12/2007 | Liao et al. |
| 7,314,974 B2 | 1/2008 | Cao et al. |
| 7,393,676 B2 | 7/2008 | Gokman et al. |
| 7,504,250 B2 | 3/2009 | Emptage et al. |
| 7,708,865 B2 * | 5/2010 | Holtzapple et al. ............. 203/25 |
| 7,858,350 B2 | 12/2010 | Burk et al. |
| 7,947,483 B2 | 5/2011 | Burgard et al. |
| 8,067,214 B2 * | 11/2011 | Burk et al. .................... 435/158 |
| 2002/0012939 A1 | 1/2002 | Palsson |
| 2002/0164729 A1 | 11/2002 | Skraly et al. |
| 2002/0168654 A1 | 11/2002 | Maranas et al. |
| 2003/0059792 A1 | 3/2003 | Palsson et al. |
| 2003/0203459 A1 | 10/2003 | Chen et al. |
| 2003/0224363 A1 | 12/2003 | Park et al. |
| 2003/0233218 A1 | 12/2003 | Schilling |
| 2003/0233675 A1 | 12/2003 | Cao et al. |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0090645 A1 | 4/2005 | Asakura |
| 2005/0164342 A1 | 7/2005 | Tobin |
| 2005/0170480 A1 | 8/2005 | Huisman |
| 2005/0221466 A1 | 10/2005 | Liao et al. |
| 2005/0239179 A1 | 10/2005 | Skraly et al. |
| 2005/0287655 A1 | 12/2005 | Tabata et al. |
| 2006/0041152 A1 | 2/2006 | Cantrell et al. |
| 2006/0046288 A1 | 3/2006 | Ka-Yiu et al. |
| 2006/0084155 A1 | 4/2006 | Huisman et al. |
| 2006/0134760 A1 | 6/2006 | Rieping |
| 2006/0141594 A1 | 6/2006 | San et al. |
| 2007/0072279 A1 | 3/2007 | Meynial-Salles et al. |
| 2007/0087425 A1 | 4/2007 | Ohto |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0292927 A1 | 12/2007 | Donaldson et al. |
| 2008/0120732 A1 | 5/2008 | Elliot |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0229451 A1 | 9/2008 | Cao et al. |
| 2008/0261230 A1 | 10/2008 | Liao et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2008/0293125 A1 | 11/2008 | Subbian et al. |
| 2009/0023182 A1 | 1/2009 | Schilling |
| 2009/0047719 A1 | 2/2009 | Burgard et al. |
| 2009/0075351 A1 | 3/2009 | Burke et al. |
| 2009/0100536 A1 | 4/2009 | Adams et al. |
| 2009/0158452 A1 | 6/2009 | Johnson et al. |
| 2009/0246842 A1 | 10/2009 | Hawkins et al. |
| 2009/0253192 A1 | 10/2009 | Emptage et al. |
| 2009/0275096 A1 | 11/2009 | Burgard et al. |
| 2010/0099925 A1 | 4/2010 | Kharas |
| 2010/0184171 A1 | 7/2010 | Jantama et al. |
| 2010/0304453 A1 | 12/2010 | Trawick et al. |
| 2010/0330634 A1 | 12/2010 | Park et al. |
| 2011/0014669 A1 | 1/2011 | Madden et al. |
| 2011/0045575 A1 | 2/2011 | Van Dien et al. |
| 2011/0129904 A1 | 6/2011 | Burgard et al. |
| 2011/0190513 A1 | 8/2011 | Lynch |

FOREIGN PATENT DOCUMENTS

| | | |
|---|---|---|
| KR | 10-2009-0025902 | 3/2009 |
| WO | WO 82/03854 | 11/1982 |
| WO | WO 91/00917 | 1/1991 |
| WO | WO 92/19747 | 11/1992 |
| WO | WO 93/02187 | 2/1993 |
| WO | WO 93/02194 | 4/1993 |
| WO | WO 93/06225 | 4/1993 |
| WO | WO 94/11519 | 5/1994 |
| WO | WO 94/12014 | 6/1994 |
| WO | WO 94/20614 | 9/1994 |
| WO | WO 94/20615 | 9/1994 |
| WO | WO 95/11985 | 5/1995 |
| WO | WO 99/06532 | 2/1999 |
| WO | WO 99/14313 | 3/1999 |
| WO | WO 00/61763 | 10/2000 |
| WO | WO 02/055995 | 7/2002 |
| WO | WO 02/061115 | 8/2002 |
| WO | WO 03/008603 | 1/2003 |
| WO | WO 03/106998 | 12/2003 |
| WO | WO 2004/018621 | 3/2004 |
| WO | WO 2004/029235 | 4/2004 |
| WO | WO 2005/026338 | 3/2005 |
| WO | WO 2005/052135 | 6/2005 |
| WO | WO 2007/030830 | 3/2007 |
| WO | WO 2007/141208 | 12/2007 |
| WO | WO 2008/018930 A2 | 2/2008 |
| WO | WO 2008/027742 | 6/2008 |
| WO | WO 2008/115840 | 9/2008 |
| WO | WO 2008/131286 | 10/2008 |
| WO | WO 2008/144626 | 11/2008 |
| WO | WO 2009/011974 | 1/2009 |
| WO | WO 2009/023493 | 2/2009 |
| WO | WO 2009/031766 | 3/2009 |
| WO | WO 2009/049274 A2 | 4/2009 |
| WO | WO 2009/094485 | 7/2009 |
| WO | WO 2009/103026 | 8/2009 |

(56) References Cited

FOREIGN PATENT DOCUMENTS

| | | |
|---|---|---|
| WO | WO 2009/111513 | 9/2009 |
| WO | WO 2009/111513 A1 | 9/2009 |
| WO | WO 2009/131040 | 10/2009 |
| WO | WO 2010/006076 | 1/2010 |
| WO | WO 2010/085731 | 7/2010 |
| WO | WO 2011/137192 | 11/2011 |

OTHER PUBLICATIONS

Kobayashi et al., "Frementative Production of 1,4-Butanediol from Sugars by *Bacillus* sp.," *Agric. Biol. Chem.* 51(6):1689-1690 (1987).
Mullins et al., "A specialized citric acid cycle requiring succinyl-coenzyme A (CoA):acetate CoA-transferase (AarC) confers acetic acid resistance on the acidophile Acetobacter aceti," *J. Bacteriol.* 190:4933-4940 (2008).
Seffernick et al., "Melamine deaminase and atrazine chlorohydrolase: 98 percent identical but functionally different," *J. Bacteriol.* 183(3):2405-2410 (2001).
Stanley et al., "Expression and stereochemical and isotope effect studies of active 4-oxalocrotonate decarboxylase," *Biochemistry* 39(12):3514 (2000).
Vita et al., "Disulfide bond-dependent mechanism of protection against oxidative stress in pyruvate-ferredoxin oxidoreductase of anaerobic Desulfovibrio bacteria," *Biochemistry* 47(3):957-964 (2008).
Witkowski et al., "Conversion of a beta-ketoacyl synthase to a malonyl decarboxylase by replacement of the active-site cysteine with glutamine," *Biochemistry* 38(36):11643-11650 (1999).
Yakunin and Hallenbeck, "Purification and characterization of pyruvate oxidoreductase from the photosynthetic bacterium Rhodobacter capsulatus," *Biochim. Biophys. Acta.* 1409(1):39-49.
Abe et al., "Biosynthesis from gluconate of a random copolyester consisting of 3-hydroxybutyrate and medium-chain-length 3-hydroxyalkanoates by *Pseudomonas* sp. 61-3," *Int. J. Biol. Macromol.* 16(3):115-119 (1994).
Aberhart and Hsu, "Stereospecific hydrogen loss in the conversion of [2H7]isobutyrate to beta-hydroxyisobutyrate in *Pseudomonas putida*. The stereochemistry of beta-hydroxyisobutyrate dehydrogenase," *J. Chem. Soc. Perkin1.* 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Physiol.* 46(10):1724-1734 (2005).
Adams and Kletzin, "Oxidoreductase-type enzymes and redox proteins involved in fermentative metabolisms of hyperthermophilic Archaea," *Adv. Protein Chem.* 48:101-180 (1996).
Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).
Ahmed and Lewis, "Fermentation of biomass-generated synthesis gas: effects of nitric oxide," *Biotechnol. Bioeng.* 97:1080-1086 (2007).
Aidoo et al., "Cloning, sequencing and disruption of a gene from *Streptomyces clavuligerus* Involved in clavulanic acid biosynthesis," *Gene* 147(1):41-46 (1994).
Akhtar and Jones, "Construction of a synthetic YdbK-dependent pyruvate:H2 pathway in *Escherichia coli* BL21(DE3)," *Metabolic Eng.* 11:139-147 (2009).
Alber et al., "Malonyl-coenzyme A reductase in the modified 3-hydroxypropionate cycle for autotrophic carbon fixation in archaeal *Metallosphaera* and *Sulfolobus* spp.," *J. Bacteriol.* 188:8551-8559 (2006).
Alberty, "Biochemical thermodynamics," *Biochem. Biophys. Acta.* 1207:1-11 (1994).
Alhapel et al., "Molecular and functional analysis of nicotinate catabolism in *Eubacterium barkeri*," *Proc. Natl. Acad. Sci. USA* 103(33)12341-12346 (2006).

Allen et al., "DNA sequence of the putA gene from *Salmonella typhimurium*: a bifunctional membrane-associated dehydrogenase that binds DMA," *Nucleic Acid Res.* 21:1676 (1993).
Amarasingham and Davis, "Regulation of alpha-ketoglutarate dehydrogenase formation in *Escherichia coli*," *J. Biol. Chem.* 240:3664-3668 (1965).
Amos and McInerey, "Composition of poly-.beta.-hydroxyalkanoate from *Syntrophomonas wottei* grown on unsaturated fatty acid substrates," *Arch. Microbiol.* 155:103-106 (1991).
Amuro et al., "Isolation and characterization of the two distinct genes for human glutamate dehydrogenase," *Biochem. Biophys. Acta.* 1049:216-218 (1990).
Andersen and Hansen, "Cloning of the lysA gene from *Mycobacterium tuberculosis*," *Gene* 124:105-109 (1993).
Andersen et al., "A gene duplication led to specialized gamma-aminobutyrate and beta-alaine aminotransferase in yeast," *FEBS J.* 274(7):1804-1817 (2007).
Andre and Jauniaux, "Nucleotide sequence of the yeast UGA1 gene encoding GABA transaminase," *Nucleic Acids Res.* 18:3049 (1990).
Andreesen and Ljungdahl, "Formate dehydrogenase of *Clostridium thermoaceticum*: incorporation of selenium-75, and the effects of selenite, molybdate, and tungstate on the enzyme," *J. Bacteriol.* 116:867-873 (1973).
Aneja and Charles, "Poly-3-hydroxybutyrate degradation in *Rhizobium* (*Sinorhizobium*) meliloti: isolation and characterization of a gene encoding 3-hydroxybutyrate dehydrogenase," *J. Bacteriol.* 181(3):849-857 (1999).
Angrand et al., "Simplified generation of targeting constructs using ET recombination," *Nucleic Acids Res.* 27:e16. (1999).
Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68-557-562 (2000).
Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).
Aoshima and Igarshi, "Nondecarboxylating and decarboxylating isocitrate dehydrogenases: oxalosuccinate reductas as an ancestral form of isocitrate dehydrogenase," *J. Bacteriol.* 190(6):2050-2055 (2008).
Aoshima et al., "A novel enzyme, citryl-CoA lyase, catalysing the second step of the citrate cleavage reaction in *Hydrogenobacter thermophilus* TK-6," *Mol. Microbiol.* 53(3):763-770 (2004).
Aoshima et al., "A novel enzyme, citryl-CoA synthetase, catalysing the first step of the citrate cleavage reaction in *Hydrogenobacter thermophilus* TK-6," *Mol. Microbiol.* 52(3):751-756 (2004).
Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).
Aoshima, "Novel enzyme reactions related to the tricarboxylic acid cycle: phylogenetic/functional implications and biotechnological applications," *Appl. Microbiol. Biotechnol.* 75(2):249-255 (2007).
Aragon and Lowenstein, "A survey of enzymes which generate or use acetoacetyl thioesters in rat liver," *J. Biol. Chem.* 258(8):4725-4733 (1983).
Arikawa et al., "Soluble fumarate reductase isoenzymes from *Saccharomyces cerevisiae* are required for anaerobic growth," *FEMS Microbiol. Lett.* 165:111-116 (1998).
Arps et al., "Genetics of Serine Pathway Enzymes in *Methylobacterium extorquens* AM1: Phosphoenolpyruvate Carboxylase and Malyl Coenzyme A Lyase," *J. Bacteriol.* 175(12):3776-3783 (1993).
Asano and Kato, "Crystalline 3-methylaspartase from a facultative anaerobe, *Escherichia coli* strain YG1002," *FEMS Microbiol. Lett.* 118(3):255-258 (1994).
Asano et al., "Alteration of substrate specificity of aspartase by directed evolution," *Biomol. Eng.* 22:95-101 (2005).
Asuncion et al., "Overexpression, purification, crystallization and data collection of 3-methylaspartase from *Clostridium tetanomorphum*," *Acta Crystallogr.D. Biol. Crystallogr.* 57:731-733 (2001).

(56) References Cited

OTHER PUBLICATIONS

Asuncion et al., "The Structure of 3-Methylaspartase from *Clostridium tetanomorphum* Functions via the Common Enolase Chemical Step," *J. Biol. Chem*. 277(10):8306-8311 (2002).
Atsumi et al., "Non-fermentative pathways for synthesis of branched-chain higher alcohols as biofuels," *Nature* 451(7174):86-89 (2008).
Baba et al., "Construction of *Escherichia coli* K-12 in-frame, single-gene knockout mutants: the Keio collection," *Mol. Syst. Biol*. 2:2006. 0008 (2006).
Baker and van der Drift, "Purification and properties of L-erythro-3,5-diaminohexanoate dehydrogenase from *Clostridium sticklandii*," *Biochemistry* 13(2):292-299 (1974).
Baker et al., "Purification and properties of L-erythro-3,5-diaminohexanoate dehydrogenase from a lysine-fermenting *Clostirdium*," *J. Biol. Chem*. 247(23):7724-7734 (1972).
Barker et al., "Butyryl-CoA:acetoacetate CoA-transferase from a lysine-fermenting *Clostridium*," *J. Biol. Chem*. 253(4):1219-1225 (1978).
Barker et al., "Pathway of Lysine Degradation in *Fusobacterium nucleatum*," *J. Bacteriol*. 152(1):201-207 (1982).
Barrick et al., "Quantitative analysis of ribosome binding sites in *E.coli*," *Nucleic Acids Res*. 22:1287-1295 (1994).
Barrowman et al., "Immunological comparison of microbial TPP-dependent non-oxidative alpha-keto acid decarboxylase," *FEMS Microbiology Lett*. 34:57-60 (1986).
Barthelmebs et al., "Expression of *Escherichia coli* of Native and Chimeric Phenolic Acid Decarboxylases with Modified Enzymatic activites and Method for Scrreening recombinant *E. coli* Strains Expressing These Enzymes," *Appl. Environ. Microbiol*. 67:1063-1069 (2001).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol*. 172:7035-7042 (1990).
Baum et al., "A plant glutamate decarboxylase containing a calmodulin binding domain, Cloning, sequence, and functional analysis," *J. Biol. Chem*. 268:19610-19617 (1993).
Benachenhou-Lahfa et al., "PCR-mediated cloning and sequencing of the gene encoding glutamate dehydrogenase from the archaeon *Sulfolobus shilbatae*: Identification of putative amino-acid signatures for extremophilic adaptation," *Gene*. 140-17-24 (1994).
Berg et al., "A 3-Hydroxypropionate/4-Hydroxybutyrate Autotrophic Carbon Dioxide Assimilation Pathway in Archaea," *Science* 318:1782-1786 (2007).
Bergquist and Gibbs, "Degenerate oligonucleotide gene shuffling," *Methods Mol. Biol*. 352:191-204 (2007).
Bergquist et al., "Degenerate oligonucleotide gene shuffling (DOGS) and random drift mutagenesis (RNDN): two complementary techniques for enzyme evolution," *Biomol. Eng*. 22:63-72 (2005).
Berkovitch et al., "A locking mechanism preventing radical damage in the absence of substrate, as revealed by the x-ray structure of lysine 5,6-aminomutase," *Proc. Natl. Acad. Sci. USA* 101:15870-15875 (2004).
Bermejo et al., "Expression of *Clostridium acetobutylicum* ATCC 824 Genes in *Escherichia coli* for Acetone Production and Acetate Detoxification," *Appl. Environ. Microbiol*. 64(3):1079-1085 (1998).
Biellmann et al., "Aspartate-beta-semialdehyde dehydrogenase from *Escherichia coli*. Purification and general properties," *Eur. J. Biochem*. 104(1):53-58 (1980).
Binstock and Shulz, "Fatty acid oxidation complex from *Escherichia coli*," *Methods Enzymo*. 71 Pt C:403-411 (1981).
Birrer et al., "Electro-transformation of *Clostridium beijerinckii* NRRL B-592 with shuttle plasmid pHR106 and recombinant derivatives," *Appl. Microbiol. Biotechnol*. 41(1):32-38 (1994).
Bisswanger, "Substrate Specificity of the Pyruvate Dehydrogenase Complex from *Escherichi coli*," *J. Biol. Chem*. 256(2):815-822 (1981).

Blanco et al., "Critical catalytic functional groups in the mechanims of aspartate-β-semialdehyde dehydrogenase," *Acta Crystallogr. D. Biol. Crystallogr*. 60:1808-1815 (2004).
Blanco et al., "The role of substrate-binding roups in the mechanism of asparte-β-semialdehyde dehydrogenase," *Acta Crystallogr. D. Biol. Crystallog*. 60:1388-1395 (2004).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur.J Biochem*. 123:563-569 (1982).
Blattner et al., "The complete genome sequence of *Escherichia coli* K-12," *Science* 277:1453-1462 (1997).
Boles et al., "Characterization of a glucose-repressed pyruvate kinase (Pyk2p) in *Saccharomyces cerevisiae* that is catalytically insensitive to fructose-1,6-bisphosphate," *J. Bacteriol*. 179:2987-2993 (1997).
Bonnarme et al., "Itaconate biosynthesis in *Aspergillus terreus*," *J. Bacteriol*. 177(12):3573-3578 (1995).
Bonner and Bloch, "Purification and Properties of Fatty Acyl Thiesterase I from *Escherichia coli*," *J. Biol. Chem*. 247(10) 3123-3133 (1972).
Bose et al., "Genetic analysis of the methanol- and methylamine-specific methyltransferase 2 genes of *Methanosarcina acetivorans* C2A," *J. Bacteriol*. 190:4017-4026 (2008).
Botsford et al., "Accumulation of glutamate by *Salmonella typhimurium* in response to osmotic stress," *Appl. Environ. Microbiol*. 60:2568-2574 (1994).
Botting et al., "Substrate Specificity of the 3-Methylaspartate Ammonia-Lyase Reaction: Observation of Differential Relative Reaction rates for Substrate-Product Pairs," *Biochemistry* 27:2953-2955 (1988).
Bower et al., "Cloning, Sequencing, and Characterization of the *Bacillus subtilis* Biotin Biosynthetic Operon," *J. Bacteriol*. 178(14):4122-4130 (1996).
Boynton et al., "Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824," *J. Bateriol*. 178(11):3015-3024 (1996).
Bradford, "A rapid and sensitive method for the quantitation of microgram quantities of protein utilizing the principle of protein-dye binding," *Anal. Biochem*. 72:248-254 (1976).
Brandl et al., "Ability of the phototrophic bacterium *Rhodospirillum rubrum* to produce various poly (beta-hydroxyalkanoates): potential sources for biodegradable polyesters," *Int. J. Biol. Macromol*. 11:49-55 (1989).
Branlant and Branlant, "Nucleotide sequence of the *Escherichia coli* gap gene. Different evolutionay behaviour of the Nad+-binding domain and of the catalytic domain of D-glyceraldehyde-3-phosphate dehydrogenase," *Eur. J. Biochem*. 150(1):61-66 (1985).
Brasen and Schonheit, "Unusual ADP-forming acetyl-coenzyme A synthetases from the mesophilic halophilic eurarchaeon *Haloarcula marismortui* and from the hyperthermophilic crenarchaeon *Pyrobaculum aerophilum*," *Arch. Microbiol*. 183:277-287 (2004).
Bravo et al., "Reliable, sensitive, rapid and quantitative enzyme-based assay for gamma-hydroxybutyric acid (GHB)," *J. Forensic Sci*. 49:379-387 (2004).
Bredweli et al., "Reactor Design Issues for Synthesis-Gas Fermentations,". *Biotechnol Prog*. 15:834-844 (1999).
Breitkreuz et al., "A novel gamma-hydroxybutyrate dehydrogenase: identification and expression of an *Arabidopsis* cDNA and potential role under oxygen deficiency," *J. Biol. Chem*. 278:41552-41556 (2003).
Bremer, "Pyruvate Dehydrogenase, Substrate Specificity and Product Inhibition," *Eur. J. Biochem*. 8:535-540 (1969).
Bridger et al., "The subunits of succinyl-coenzyme. A synthetase—function and assembly," In Krebs' Citric Acid Cycle—Half a Century and Still Turning, *Biochem. Soc. Symp*. 54:103-111 (1987).
Brosch et al., "Genome plasticity of BCG and impact on vaccine efficacy," *Proc. Natl. Acad. Sci. U.S.A*. 104(13):5596-5601 (2007).
Bu et al., "Two human glutamate decarboxylases, 65-kDa GAD and 67-kDa GAD, are each encoded by a single gene," *Proc. Natl. Acad. Sci. U.S.A*. 89(6):2115-2119 (1992).

(56) References Cited

OTHER PUBLICATIONS

Bu, et al., "The exon-intron organization of the genes (GAD1 and GAD2) encoding two human glutamate decarboxylases (GAD67 and GAD65) suggests that they derive from a common ancestral GAD," *Genomics* 21:222-228 (1994).
Buck and Guest, "Overexpression and site-directed mutagenesis of the succinyl-CoA synthetase of *Escherichia coli* and nucleotide sequence of a gene (g30) that is adjacent to the suc operon," *Biochem. J.* 260(3):737-747 (1989).
Buck et al., "Primary Structure of the Succinyl-CoA Synthetase of *Escherichia coli*," *Biochemistry* 24:6245-6252 (1985).
Buck et al., "Cloning and expression of the succinyl-CoA synthetase genes of *Escherichia coli* K12," *J. Gen. Microbiol.* 132(6):1753-1762 (1986).
Buckel et al., "Glutaconate CoA-Transferase from *Acidaminococcus fermentans*," *Eur. J. Biochem.* 118:315-321 (1981).
Bult et al., "Complete genome sequence of the methanogenic archaeon, *Methanococcus jannaschii*," *Science* 273:1058-1073 (1996).
Burgard and Maranas, "Probing the Performance Limits of the *Escherichia coli* Metabolic Network Subject to Gene Additions or Deletions," *Biotechnol. Bioeng.* 74(5):364-375 (2001).
Burgard et al., "Minimal reaction sets for *Escherichia coli* metabolism under different growth requirements and uptake environments," *Biotechnol. Prog.* 17(5):791-797 (2001).
Burgard et al., "Optknock: a bilevel programming framework for identifying gene knockout strategies for microbial strain optimization," *Biotechnol. Bioeng.* 84(6):647-657 (2003).
Burke et al, "The Isolation, Characterization, and Sequence of the Pyruvate Kinase Gene of *Saccharomyces cerevisiae*," *J. Biol. Chem.* 258(4):2193-2201 (1983).
Buu et al., "Functional Characterization and Localization of Acetyl-CoA Hydrolase, Ach1p, in *Saccharomyces cerevisiae*," *J. Biol. Chem.* 278(19):17203-17209 (2003).
Campbell et al., "A new *Escherichia coli* metabolic competency: growth on fatty acids by a novel anaerobic β-oxidation pathway," *Mol. Microbiol.* 47(3):793-805 (2003).
Cary et al., "Cloning and expression of *Clostridium acetobutylicum* ATCC 824 acetoacetyl-coenzyme A:acetate/butyrate:coenzyme A-transferase in *Escherichia coli*," *Appl. Environ. Microbiol.* 56(6):1576-1583 (1990).
Cary et al., "Cloning and expression of *Clostridium acetobutylicum* phosphotransbutyrylase and butyrate kinase genes in *Escherichia coli*," *J. Bacteriol.* 170(10):4613-4618 (1988).
Caspi et al., "MetaCyc: a multiorganism database of metabolic pathways and enzymes," *Nucleic Acids Res.* 34(Database issue):D511-D516 (2006).
Causey et al., "Engineering *Escherichia coli* for efficient conversion of glucose to pyruvate," *Proc. Natl. Acad. Sci. U.S.A.* 101:2235-2240 (2004).
Cha and Parks, Jr., "Succinic Thiokinase. I. Purification of the Enzyme from Pig Heart," *J. Biol. Chem.* 239:1961-1967 (1964).
Chandra Raj et al., "Pyruvate decarboxylase: a key enzyme for the oxidative metabolism of lactic acid by *Acetobacter pasteurianus*," *Arch. Microbiol.* 176:443-451 (2001).
Chavez et al., "The NADP-glutamate dehydrogenase of the cyanobacterium Synechocystis 6803: cloning, transcriptional analysis and disruption of the gdhA gene," *Plant Mol. Biol.* 28:173-188 (1995).
Chen and Hiu, "Acetone-Butanol-Isopropanol Production by *Clostridium beijerinckii* (Synonym, Clostridium Butylicum)," *Biotechnology Letters* 8(5):371-376 (1986).
Chen and Lin, "Regulation of the adhE gene, which encodes ethanol dehydrogenase in *Escherichia coli*," *J. Bacteriol.* 173(24):8009-8013 (1991).
Chen et al., "A novel lysine 2,3-aminomutase encoded by the yodO gene of *Bacillus subtilis*: characterization and the observation of organic radical intermediates," *Biochem. J.* 348:539-549 (2000).

Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).
Chicco et al., "Regulation of Gene Expression of Branched-chain Keto Acid Dehydrogenase Complex in Primary Cultured Hepatocytes by Dexamethasone and cAMP Analog," *J. Biol. Chem.* 269(30):19427-19434 (1994).
Chirpich et al., "Lysine 2,3-Aminomutase. Purification and properties of a pyridoxal phosphate and S-adenosylmethionine-activated enzyme," *J. Biol. Chem.* 245(7):1778-1789 (1970).
Cho et al., "Critical residues for the coenzyme specificity of NAD+-deptendent 15-hydroxyprtaglandin dehydrogenase," *Arch. Biochem. Biophys.* 419(2): 139-146 (2003).
Chowdhury et al., "Cloning and Overexpression of the 3-Hydroxyisobutyrate Dehydrogenase Gene from *Pseudomonas putida* E23," *Biosci. Biotechnol. Biochem.* 67(2):438-441 (2003).
Chowdhury et al., "3-Hydroxyisobutyrate dehydrogenase from *Pseudomonas putida* E23: purification and characterization," *Biosci. Biotechnol. Biochem.* 60(12):2043-2047 (1996).
Christenson et al., "Kinetic analysis of the 4-methylideneimidazole-5-one-containing tyrosine aminomutase in enediyne antitumor antibiotic C-1027 biosynthesis," *Biochemistry* 42(43):12708-12718 (2003).
Chu et al., "Enzymatically active truncated cat brain glutamate decarboxylase: expression, purification, and absorption spectrum," *Arch. Biochem. Biophys.* 313:287-295 (1994).
Clark and Ljungdahl, "Purification and properties of 5,10-methylenetetrahydrofolate reductase from *Clostridium formicoaceticum*," *Methods Enzymol.* 122:392-399 (1986).
Clark and Ljungdahl, "Purification and properties of 5,10-methylenetetrahydrofolate reductase, an iron-sulfur flavoprotein from *Clostridium formicoaceticum*," *J. Biol. Chem.* 259:10845-10849 (1984).
Clark, Progress Report for Department of Energy Grant DE-FG02-88ER13941, "Regulation of Alcohol Fermentation in *Escherichia coli*," pp. 1-7 for the period: Jul. 1991-Jun. 1994.
Clarke et al., "Rational construction of a 2-hydroxyacid dehydrogenase with new substrate specificity," *Biochem. Biophys. Res. Commun.* 148:15-23 (1987).
Clausen et al., "PAD1 encodes phenylacrylic acid decarboxylase which confers resistance to cinnamic acid in *Saccharomyces cerevisiae*," *Gene* 142:107-112 (1994).
Cock et al., "A nuclear gene with many introns encoding ammonium-inductible chloroplastic NADP-specific glutamate dehydrogenase(s) in *Chlorella sorokiniana*," *Plant Mol. Biol.* 17:1023-1044 (1991).
Coco et al., "DNA shuffling method for generating highly recombined genes and evolved enzymes," *Nat. Biotechnol.* 19(4):354-359 (2001).
Cogoni et al., "*Saccharomyces cerevisiae* has a single glutamate synthase gene coding for a plant-like high-molecular-weight polypeptide," *J. Bacteriol.* 177:792-798 (1995).
Colby and Chen, "Purification and properties of 3-Hydroxybutyryl-Coenzyme A Dehydrogenase from *Clostridium beijerinckii* (*Clostridium butylicum*:) NRRL B593," *Appl. Environ. Microbiol.* 58:3297-3302 (1992).
Cole et al., "Deciphering the biology of *Mycobacterium tuberculosis* from the complete genome sequence," *Nature* 393:537-544 (1998).
Coleman et al., "Expression of a glutamate decarboxylase homologue is required for normal oxidative stress tolerance in *Saccharomyces cerevisiae*," *J. Biol. Chem.* 276:244-250 (2001).
Cooper, "Glutamate-γ-aminobutyrate transaminase," *Methods Enzymol.* 113:80-82 (1985).
Corthesy-Theulaz et al., "Cloning and characterization of *Helicobacter pylori* succinyl CoA:acetoacetate CoA-transferase, a novel prokaryotic member of the CoA-transferase family," *J. Biol. Chem.* 272(41):25659-25667 (1997).
Creaghan and Guest, "Succinate dehydrogenase-dependent nutritional requirement for succinate in mutants of *Escherichia coli* K12," *J. Gen. Microbiol.* 107(1):1-13 (1978).
Cukalovic et al., "Feasibility of production method for succinic acid derivatives: a marriage of renewable resources and chemical technology," *Biofuels Bioprod. Bioref.* 2:505-529 (2008).

(56) References Cited

OTHER PUBLICATIONS

Cunningham and Guest, "Transcription and transcript processing in the sdhCDAB-sucABCD operon of *Escherichia coli*," *Microbiology* 144:2113-2123 (1998).
Cunningham et al., "Transcriptional regulation of the aconitase genes (acnA and acnB) of *Escherichia coli*," *Microbiology* 143:3795-3805 (1997).
D'Ari and Rabinowitz, "Purification, characterization, cloning, and amino acid sequence of the bifunctional enzyme 5,10-methylenetetrahydrofolate dehydrogenase/5,10-methenyltetrahydrofolate cyclohydrolase from *Escherichia coli*," *J. Biol. Chem.* 266:23953-23958 (1991).
Darlison et al., "Nucleotide sequence of the sucA gene encoding the 2-oxoglutarate dehydrogenase of *Escherichia coli* K12," *Eur. J. Biochem.* 141(2):351-359 (1984).
Das et al, "Characterization of a corrinoid protein involved in the C1 metabolism of strict anaerobic bacterium *Moorella thermoacetica*," *Proteins* 67:167-176 (2007).
Database WPI Week 198804 Thomson Scientific, London, GB; AN 1988-025175.
Datar et al., "Fermentation of biomass-generated producer gas to ethanol," *Biotechnol. Bioeng.* 86:587-594 (2004).
Datsenko and Wanner, "One-step inactivation of chromosomal genes in *Escherichia coli* K-12 using PCR products," *Proc. Natl. Acad. Sci. U.S.A.* 97(12):6640-6645 (2000).
Davie et al., "Expression and Assembly of a Functional E1 Component (α2β32) of Mammalian Branched-Chain α-Ketoacid Dehydrogenase Complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr. Purif.* 8:430-438 (1996).
de Bok et al., "Two W-containing formate dehydrogenases (CO2-reductases) involved in syntrophic propionate oxidation by *Syntrophobacter fumaroxidans*," *Eur. J. Biochem.* 270:2476-2485 (2003).
de la Torre et al., "Identification and functional analysis of prokaryotic-type aspartate aminotransferase: implications for plant amino acid metabolism," *Plant J.* 46(3):414-425 (2006).
de Mata and Rabinowitz, "Formyl-methenyl-methylenetetrahydrofolate synthetase(combined) from yeast. Biochemical characterization of the protein from an ade3 mutant lacking the formyltetrahydrofolate synthetase function," *J. Biol. Chem.* 255:2569-2577 (1980).
Deana, "Substrate specificity of a dicarboxyl-CoA: dicarboxylic acid coenzyme A transferase from rat liver mitochondria," *Biochem. Int.* 26(4):767-773 (1992).
Deckert et al., "The complete genome of the hyperthermophilic bacterium *Aquifex aeolicus*," *Nature* 392:353-358 (1998).
Diao et al., "Crystal Structure of Butyrate Kinase 2 from *Thermotoga maritima*, a Member of the ASKHA Superfamily of Phosphotransferases," *J. Bacteriol.* 191(8):2521-2529 (2009).
Diao et al., "Crystallization of butyrate kinase 2 from *Thermotoga maritima* medicated by varpor diffusion of acetic acid," *Acta Crystallogr. D. Crystallogr.* 59:1100-1102 (2003).
Diaz et al., "Gene cloning, heterologous overexpression and optimized refolding of the NAD-glutamate dehydrogenase from haloferax mediterranei," *Extremophiles* 10(2):105-115 (2006).
Diderichsen et al., "Cloning of aldB, which encodes alpha-acetolactate decarboxylase, an exoenzyme from *Bacillus brevis*," *J. Bacteriol.* 172(8):4315-4321 (1990).
Diruggiero et al., "Expression and in vitro assembly of recombinant glutamate dehydrogenase from the hyperthermophilic archaeon *Pyrococcus furiosus*," *Appl. Environ. Microbiol.* 61:159-164 (1995).
Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153:21-33 (2009).

Dobbek et al., "Crystal structure of a carbon monoxide dehydrogenase reveals a [Ni-4Fe-5S] cluster," *Science* 293:1281-1285 (2001).
Doi et al., "Biosynthesis and characterization of poly(3-hydroxybutyrate-co-4-hydroxybutyrate) in *Alcaligenes eutrophus*," *Int. J. Biol. Macromol.* 12:106-111 (1990).
Doi et al., "Nuclear Magnetic Resonance Studies on Unusual Bacterial Copolyesters of 3-Hydroxybutyrate and 4-Hydroxybutyrate," *Macromolecules* 21:2722-2727 (1988).
Doi, "Microbial Synthesis, Physical Properties, and Biodegradability of Polyhydroxyalkanoates," *Macromol Symp.* 98:585-599 (1995).
Dombek and Ingram, "Ethanol production during batch fermentation with *Saccharomyces cerevisiae*: changes in glycolytic enzymes and internal pH," *Appl. Environ. Microbiol.* 53:1286-1291 (1987).
Donnelly and Cooper, "Succinic semialdehyde dehydrogenases of *Escherichia coli*: their role in the degradation of p-hydroxyphenylacetate and gamma-aminobutyrate," *Eur. J. Biochem.* 113(3):555-561 (1981).
Donnelly and Cooper, "Two succinic semialdehyde dehydrogenases are induced when *Escherichia coli* K-12 is grown on gamma-aminobutyrate," *J. Bacteriol.* 145:1425-1427 (1981).
Dover et al., "Genetic analysis of the gamma-aminobutyrate utilization pathway in *Escherichia coli* K-12," *J. Bacteriol.* 117(2):494-501 (1974).
Doyle et al., "Structural basis for a change in substrate specificity: crystal structure of S113E isocitrate dehydrogenase in a complex with isopropylmalate, Mg2+, and NADP," *Biochemistry* 40(14):4234-4241 (2001).
Drake and Daniel, "Physiology of the thermophilic acetogen *Moorella thermoacetica*," *Res. Microbiol.* 155:869-883 (2004).
Drake, "Demonstration of hydrogenase in extracts of the homoacetate-fermenting bacterium *Clostridium thermoaceticum*," *J. Bacteriol.* 150:702-709 (1982).
Drake, "Acetogenesis, acetogenic bacteria, and the acetyl-CoA "Wood/Ljungdahl" pathway: past and current perspectives," In H.L. Drake (ed.), *Acetogenesis* pp. 3-60 Chapman and Hall, New York, (1994).
Drewke et al., "4-O-Phosphoryl-L-threonine, a substrate of the pdxC(serC) gene product involved in vitamin $B_6$ biosynthesis," *FEBS Lett.* 390:179-182 (1996).
Duncan et al., "Acetate utilization and butyryl coenzyme A (CoA):acetate-CoA transferase in butyrate-poducing bacteria from the human large intestine," *Appl. Environ. Microbiol.* 68(10):5186-5190 (2002).
Duncan et al., "Purification and properties of NADP-dependent glutamate dehydrogenase from *Ruminococcus flavefaciens* FD-1," *Appl. Environ. Microbiol.* 58:4032-4037 (1992).
Durre and Bahl, "Microbial Production of Acetone/Butanol/Isopropanol," In *Biotechnology* vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).
Dürre et al., "Solventogenic enzymes of *Clostridium acetobutylicum*: catalytic properties, genetic organization, and transcriptional regulation," *FEMS Microbiol. Rev.* 17(3):251-262 (1995).
Dürre, "New insights and novel developments in clostridial acetone/butanol/isopropanol fermentation," *Appl. Microbiol. Biotechnol.* 49:639-648 (1998).
Edwards and Palsson, "Systems properties of the Haemophilus influenzae Rd metabolic genotype," *J. Biol. Chem.* 274(25):17410-17416 (1999).
Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).
Edwards et al., "In Silico Predictions of *Escherichia coli* metabolic capabilities are Consistent with Experimental Data," *Nat. Biotechnol.* 19(2):125-130 (2001).
Efe et al., "Options for biochemical production of 4-hydroxybutyrate and its lactone as a substitute for petrochemical production," *Biotechnol. Bioeng.* 99:1392-1406 (2008).

(56) References Cited

OTHER PUBLICATIONS

Eggen et al., "The glutamate dehydrogenase-encoding gene of the hyperthermophilic archaeon *Pyrococcus furiosus*: sequence, transcription and analysis of the deduced amino acid sequence," *Gene* 132:143-148 (1993).

Eikmanns et al., "The phosphoenolpyruvate carboxylase gene of *Corynebacterium glutamicum*: Molecular cloning, nucleotide sequence, and expression," *Mol. Gen. Genet.* 218:330-339 (1989).

Ekiel et al., "Acetate and CO2 assimilation by *Methanothrix concilii*," *J. Bacteriol.* 162(3):905-098 (1985).

Enomoto et al., "Cloning and sequencing of the gene encoding the soluble fumarate reductase from *Saccharomyces cerevisiae*," *DNA Res.* 3:263-267 (1996).

Estevez et al., "X-ray crystallographic and kinetic correlation of a clinically observed human fumarase mutation," *Protein Sci.* 11:1552-1557 (2002).

Evans et al., "A new ferredoxin-dependent carbon reduction cycle in a photosynthetic bacterium," *Proc. Natl. Acad. Sci. U.S.A.* 55(4):928-934 (1966).

Faehnle et al., "A New Branch in the Family: Structure of Aspartate-β-semialdehyde dehydrogenase from *Methanococcus jannaschii*," *J. Mol. Biol.* 353:1055-1068 (2005).

Feist et al., "The growing scope of applications of genome-scale metabolic reconstructions using *Escherichia coli*," Nat. Biotechnol. 26(6):659-667 (2008).

Fell and Small, "Fat Synthesis in Adipose Tissue. An Examination of Stoichiometric Constraints," *Biochem. J.* 238(3):781-786 (1986).

Fernandez-Valverde et al., "Purification of Pseudomonas putida Acyl coenzyme a Ligase Active with a Range of Aliphatic and Aromatic Substrates," *Appl. Environ. Microbiol.* 59:1149-1154 (1993).

Filetici et al., "Sequence of the GLT1 gene from *Saccharomyces cerevisiae* reveals the doamain structure of yeast glutamate synthese," *Yeast* 12:1359-1366 (1996).

Fischer and Sauer, "Metabolic flux profiling of *Escherichi coli* mutants in central carbon metabolism using GC-MS," *Eur. J. Biochem.* 270(5) 880-891 (2003).

Fishbein and Bessman, "Purification and properties of an enzyme in human blood and rat liver microsomes catalyzing the formation and hydrolysis of gamma-lactones. I. Tissue localization, stoichiometry, specificity, distinction from esterase," *J. Biol. Chem.* 241(21):4835-4841 (1966).

Föllner et al., "Analysis of the PHA granule-associatc proteins GA20 and GA11 in *Methylobacterium extorquens* and *Methylobacterium rhodesianum*," *J. Basic Microbiol.* 37(1):11-21 (1997).

Fong and Palsson, "Metabolic gene-deletion strains of *Escherichia coli* evolve to computationally predicted growth phenotypes," *Nat. Genet.* 36(10):1056-1058 (2004).

Fong et al., "Description and interpretation of adaptive evolution of *Escherichia coli* K-12 MG1655 by using a genome-scale in silico metabolic model," *J. Bacteriol.* 185(21):6400-6408 (2003).

Fontaine et al., "A New Type of Glucose Fermentation by *Clostridium thermoaceticum* N.Sp.," *J. Bacteriol.* 43:701-715 (1942).

Fontaine et al., "Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184(3):821-830 (2002).

Ford, et al., "Molecular properties of the lys1+ gene and the regulation of alpha-aminoadipate reductase in *Schizosaccharomyces pombe*," *Curr. Genet.* 288(2):131-137 (1995).

Forster et al., "Genome-scale reconstruction of the *Saccharomyces cerevisiae* metabolic network," *Genome Res.* 13:244-253 (2003).

Fox et al, "Characterization of the region encoding the CO-induced hydrogenase of *Rhodospirillum rubrum*," *J. Bacteriol.* 178:6200-6208 (1996).

Friedrich et al., "The complete stereochemistry of the enzymatic dehydration of 4-hydroxybutyryl coenzyme A to crotonyl coenzyme A," *Angew. Chem. Int. Ed. Engl.* 47:3254-3257 (2008).

Fries et al., "Reaction Mechanism of the Heteroameric ($\alpha_2\beta_2$) E1 Component of 2-Oxo Acid Dehydrogenase Multienzyme Complexes," *Biochemistry* 42:6996-7002 (2003).

Fuhrer, et al., "Computational prediction and experimental verification of the gene encoding the NAD+/NADP+-dependent succinate semialdehyde dehydrogenase in *Escherichia coli*," *J. Bacteriol.* 189:8073-8078 (2007).

Fujii et al., "Characterization of L-lysine 6-aminotransferase and its structural gene from *Favobacterium lutescens* IFO3084," *J. Biochem.* 128(3):391-397 (2000).

Fujii et al., "Error-prone rolling circle amplification: the simplest random mutagenesis protocol," *Nat. Protoc.* 1(5):2493-2497 (2006).

Fujii et al., "One-step random mutagenesis by error-prone rolling circle amplification," *Nucleic Acids Res.* 32(19):e145 (2004).

Fujita et al., "Novel Substrate Specificity of designer3-Isopropylmalate Dehydrogenase Derived from thermus thermophilus HBI," *Biosci. Biotechnol. Biochem.* 65(12):2695-2700 (2001).

Fukao et al., "Succinyl-coA:3-Ketoacid CoA Transferase (SCOT): Cloning of the Human SCOT Gene, Tertiary Structural Modeling of the Human SCOT Monomer, and Characterization of Three Pathogenic Mutations," *Genomics* 68:144-151 (2000).

Fukuda and Wakagi, "Substrate recognition by 2-oxoacid:ferredoxin oxidoreductase from *Sulfolobus* sp. Strain 7," *Biochim. Biophys. Acta* 1597:74-80 (2002).

Fukuda et al., "Role of a highly conserved YPITP motif in 2-oxoacid:ferredoxin oxidoreductase," *Eur. J. Biochem.* 268:5639-5646 (2001).

Furdui and Ragsdale, "The role of pyruvate ferredoxin oxidoreductase in pyruvate synthesis during autotrophic growth by the Wood-Ljungdahl pathway," *J. Biol. Chem.* 275:28494-28499 (2000).

Galagan et al., "The genome of *M. acetivorans* reveals extensive metabolic and physiological diversity," *Genome Res.* 12:532-542 (2002).

Gallego et al., "A role for glutamate decarboxylase during tomato ripening: the characterisation of a cDNA encoding a putative glutamate decarboxylase with a calmodulin-binding site," *Plant Mol. Biol.* 27:1143-1151 (1995).

Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).

Gay et al., "Cloning Structural Gene sacB, Which codes for Exoenzyme Levansucrase of *Bacillus subtilis*: Epxresion of the Gene in *Escherichia coli*," *J. Bacteriol.* 153:1424-1431 (1983).

Gerhardt et al., "Fermentation of 4-aminobutyrate by *Clostridium aminobutyricum*: cloning of two genes involved in the formation and dehydration of 4-hydroxybutyryl-CoA," *Arch. Microbiol.* 174:189-199 (2000).

Gerischer and Dürre, "mRNA Analysis of the adc Gene Region of *Clostridium acetobutylicum* during the Shift to Solventogenesis," *J. Bacteriol.* 174(2):426-433 (1992).

Gerngross and Martin, "Enzyme-catalyzed synthesis of poly((R)-(−)-3-hydroxybutyrate): formation of macroscopic granules in vitro," *Proc. Natl. Acad. Sci. U.S.A.* 93:6279-6783 (1995).

Gerngross, et al., "Overexpression and purification of the soluble polyhydroxyalkanoate synthase from *Alcalligenes eutrophus*: evidence for a required posttranslational modification for catalytic activity," *Biochemistry* 33:9311-9320 (1994).

Gibbs et al., "Degenerate oligonucleotide gene shuffling (DOGS): a method for enhancing the frequency of recombination with family shuffling," *Gene.* 271:13-20 (2001).

Gibson and McAlister-Henn, "Physical and Genetic Interactions of Cytosolic Malate Dehydrogenase with Other Gluconeogenic Enzymes," *J. Biol. Chem.* 278(28):25628-25636 (2003).

Giesel and Simon, "On the occurrence of enoate reductase and 2-oxocarboxylate reductase in clostridia and some observations on the amino acid fermentation by *Peptostreptococcus anaerobius*," *Arch. Microbiol.* 135(1):51-57 (1983).

Girbal, et al., "Regulation of metabolic shifts in *Clostridium acetobutylicum* ATCC 824," *FEMS Microbiol. Rev.* 17:287-297 (1995).

(56) References Cited

OTHER PUBLICATIONS

Goda et al., "Cloning, Sequencing, and Expression in *Escherichia coli* of the *Clostridium tetanomorphum* Gene Encoding β-Methylaspartase and Characterization of the Recombinant Protein," *Biochemistry* 31:10747-10756 (1992).

Gong et al., "Effects of transport properites of ion-exchange membranes on desalination of 1,3-propanediol fermentation broth by electrodialysis," *Desalination* 191:193-199 (2006).

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

Gonzalez and Robb, "Genetic analysis of Carboxydothermus hydrogenoformans carbon monoxide dehydrogenase genes cooF and cooS," *FEMS Microbiol. Lett.* 191:243-247 (2000).

Gonzalez, et al., "Cloning of a yeast gene coding for the glutamate synthase small subunit (GUS2) by complementation of *Saccharomyces cerevisiae* and *Escherichia coli* glutamate auxotrophs," *Mol. Microbiol.* 6:301-308 (1992).

Gonzalez-Pajuelo et al., "Metabolic engineering of *Clostridium acetobutylicum* for the industrial production of 1,3-propanediol from glycerol," *Met. Eng.* 7:329-336 (2005).

Goupil et al., "Imbalance of leucine flux in *Lactoccus lactis* and its use for the isolation of diacetyl-overproducing strains," *Appl. Environ. Microbiol.* 62(7):2636-2640 (1996).

Goupil-Feuillerat et al., "Transcriptional and translational regulation of alpha-acetolactate decarboxylase of *Lactococcus lactis* subsp. Lactis," *J. Bacteriol.* 183(19):5399-5408 (2000).

Green et al., "Catabolism of α-Ketoglutarate by a sucA Mutant of *Bradyrhizobium japonicum*: Evidence for an Alternative Tricarboxylic Acid Cycle," *J. Bacteriol.* 182(10):2838-2844 (2000).

Gregerson, et al., "Molecular characterization of NADH-dependent glutamate synthase from alfalfa nodules," *Plant Cell* 5:215-226 (1993).

Grubbs, "Olefin Metathesis," *Tetrahedron* 60:7117-7140 (2004).

Guest et al., "The fumarase genes of *Escherichia coli*: location of the fumB gene and discovery of a new gene (fumC)," *J. Gen. Microbiol.* 131:2971-2984 (1985).

Guirard and Snell, "Purification and properties of ornithine decarboxylase from *Lactobacillus* sp. 30a," *J. Biol. Chem.* 255(12):5960-5964 (1980).

Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from *Schizosaccharomyces pombe*," *Yeast* 21(15):1279-1288 (2004).

Guo et al., "Site-directed mutational analysis of the novel catalytic domains of alpha-aminoadipate reductase (Lys2p) from *Candida albicans*," *Mol. Genet. Genomics* 269(2):271-279 (2003).

Guzman, et al., "Tight regulation, modulation and high-level expression by vectors containing the arabinose PBAD promoter," *J. Bacteriol.* 177(14):4121-4130 (1995).

Hadfield et al., "Active site analysis of the potential antimicrobial target aspartate semialdehyde dehydrogenase," *Biochemistry* 40(48):14475-14483 (2001).

Hadfield et al., "Structure of aspartate-beta-semialdehyde dehydrogenase from *Escherichia coli*, a key enzyme in the aspartate family of amino acid biosynthesis," *J. Mol. Biol.* 289(4):991-1002 (1999).

Hagemeier et al., "Insight into the mechanism of biological methanol activation based on the crystal structure of the methanol-cobalamin methyltransferase complex," *Proc. Natl. Acad. Sci. U.S.A.* 103:18917-18922 (2006).

Hammer and Bode, "Purification and characterization of an inducible L-lysine:2-oxoglutarate 6-aminostransferase from *Dandida utilis*," *J. Basic Microbiol.* 32:21-27 (1992).

Hanai et al., "Engineered synthetic pathway for isopropanol production in *Escherichia coli*," *Appl. Environ. Microbiol.* 73:7814-7818 (2007).

Hansford, "Control of mitochondrial substrate oxidation," *Curr. Top. Bioenerg.* 10:217-278 (1980).

Harms and Thauer, "Methylcobalamin: coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235:653-659 (1996).

Hasegawa et al., "Transcriptional regulation of ketone body-utilizing enzyme, acetoacetyl-CoA synthetase, by C/EBPα during adipocyte differentiation," *Biochim. Biophys. Acta* 1779:414-419 (2008).

Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).

Hashidoko et al., "Cloning of a DNA Fragment Carrying the 4-Hydroxycinnamate Decarboxylase (*pof*K) Gene from *Klebsiella oxtoca*, and Its Constitutive Expression in *Escherichia coli* JM109 Cells," *Biosci. Biotech. Biochem.* 217-218 (1994).

Hashimoto et al., "Activation of L-Lysine ε-Dehydrogenase from *Agrobacterium tumefaciens* by Several Amino Acids and Monocarboxylates," *J. Biochem.* 106:76-80 (1989).

Hasson et al., "The Crystal Structure of Benzoylformate Decarboxylase at 1.6 Å Resolution: Diversity of Catalytic Residues in thiamin Diphosphate-Dependent Enzymes," *Biochemistry* 37:9918-9930 (1998).

Hawes et al., "Mammalian 3-hydroxyisobutyrate dehydrogenase," *Methods Enzymol.* 324:218-228 (2000).

Hayden et al., "Glutamate dehydrogenase of *Halobacterium salinarum*: evidence that the gene sequence currently assigned to the NADP+-dependent enzyme is in fact that of the NAD+-dependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. U.S.A.* 99(25):15926-15931 (2002).

Hein, et al., "Biosynthesis of poly(4-hydroxybutyric acid) by recombinant strains of *Escherichia coli*," *FEMS Microbiol. Lett.* 153(2):411-418 (1997).

Henne, et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy, et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).

Henning et al., "Identification of Novel enzoylformate Decarboxlyases by Growth Selection," *App. Environ. Microbiol.* 73(12)7510-7517 (2006).

Hermes et al., "Searching sequence space by definably random mutagenesis: Improving the catalytic potency of an enzyme," *Proc. Natl. Acad. Sci. U.S.A.* 87:696-700 (1990).

Herrmann et al., "Energy conservation via electron-transferring flavoprotein in anaerobic bacteria," *J. Bacteriol.* 190(3):784-791 (2007).

Herrmann et al., "Two beta-alanyl-CoA:ammonia lyases in *Clostridium propionicum*," *FEBS J.* 272:813-821 (2005).

Hesslinger et al., "Novel keto acid formate-lyase and propionate kinase enzymes are components of an anaerobic pathway in *Escherichia coli* that degrades L-threonine to propionate," *Mol. Microbiol* 27:477-492 (1998).

Hester et al., "Purification of active E1 alpha 2 beta 2 of *Pseudomonas putida* branched-chain-oxoacid dehydrogenase," *Eur. J. Biochem.* 233(3):828-836 (1995).

Heydari et al., "Highly Stable L-Lysine 6-Dehydrogenase from the Thermophile *Geobacillus stearothemophilus* Isolated from a Japanese Hot Spring: Characterization, gene Cloning and Sequencing, and Expression," *Appl. Environ. Microbiol.* 73:937-942 (2004).

Hezayen et al., "Biochemical and enzymological properties of the polyhydroxybutyrate synthase from the extremely halophilic archaeon strain 56," *Arch. Biochem. Biophys.* 403(2):284-291 (2002).

(56) References Cited

OTHER PUBLICATIONS

Hibbert et al. "Directed evolution of biocatalytic processes," *Biomol. Eng.* 22:11-19 (2005).
Hijarrubia et al., "Domain Structure characterization of the Multifunctional α-Aminoadipate Reductase from *Penicillium chrysogenum* by Limited Proteolysis," *J. Biol. Chem.* 278:8250-8256 (2003).
Hillmer and Gottschalk, "Solubilization and partial characterization of particulate dehydrogenases from *Clostridium kluyveri*," *Biochim. Biophys. Acta* 334:12-23 (1974).
Hiramitsu, et al., "Production of Poly(3-hydroxybutyrate-co-4-hydroxybutyrate) by *Alcallgenes latus*," *Biotechnol Lett.* 15:461-464 (1993).
Hirano et al., "Purification and Characterization of the alcohol dehydrogenase with a broad substrate specificity originated from 2-phenylethanol-assimilating *Brevibacterium* sp. KU 1390," *J. Biosci. Bioeng.* 100(3):318-322 (2005).
Hiser et al., "ERG10 from *Saccharomyces cerevisiae* encodes acetoacetyl-CoA thiolase," *J. Biol. Chem.* 269:31383-31389 (1994).
Hoffmeister et al., "Mitochondrial trans-2-enoyl-CoA reductase of wax ester fermentation from *Euglena gracilis* defines a new family of enzymes involved in lipid synthesis," *J. Biol. Chem.* 280:4329-4338 (2005).
Hogan et al., "Improved specificity toward substrates with ositively charged side chains by site-directed mutagenesis of the L-lactate dehydrogenase of *Bacillus stearothermophilus*," *Biochemistry* 34(13):4225-4230 (1995).
Hong and Lee, "Enhanced Production of Succinic Acid by Metabolically Engineered *Escherichia coli* with Amplified Activities of Malic Enzyme and Fumarase," *Biotechnol. Bioprocess Eng.* 9:252-255 (2004).
Hong, et al., "The genome sequence of the capnophilic rumen bacterium *Mannheimia succiniciproducens*," *Nat. Biotechnol.* 22(10):1275-1281 (2004).
Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).
Huang et al., "Identification and Characterization of a Second Butyrate Kinase from *Clostridium acetobutylicum* ATCC 824," *J. Mol. Microbiol. Biotechnol.* 2(1):33-38 (2000).
Huang et al., "Purification and Characterization of a Ferulic Acid Decarboxylase from *Pseudomonas fluorescens*," *J. Bacteriol.* 176(19):5912-5918 (1994).
Hughes et al., "Evidence for Isofunctional Enzymes in the Degradation of Phenol, *m*- and *p*-Toulate, and *p*-Cresol via Catechol meta-Cleavage Pathways in *Alcaligenes eutrophus*," *J. Bacteriol.* 158:79-83 (1984).
Hugler et al., "Autotrophic CO2 fixation via the reductive tricarboxylic acid cycle in different lineages within the phylum Aquificae: evidence for two ways of citrate cleavage," *Environ. Microbiol.* 9:81-92 (2007).
Hugler et al., "Evidence for autotrophic Co2 fixation via the reductive tricarboxylic acid cycle by members of the epsilon subdivision of proteobacteria," *J. Bacteriol.* 187(9):3020-3027 (2005).
Hugler et al., "Malonyl-coenzyme A reductase from *Chloroflexus aurantiacus*, a key enzyme of the 3-hydroxypropionate cycle for autotrophic CO(2) fixation," *J.Bacteriol.* 184:2404-2410 (2002).
Huh et al., "Global analysis of protein localization in budding yeast," *Nature* 425:686-691 (2003).
Huisman and Lalonde, "Ch. 30: Enzyme Evolution for Chemical Process Applications," In R N. Patel (ed.), *Biocatalysis in the pharmaceutical and biotechnology industries*, CRC Press, Boca Raton, FL, p. 717-742 (2007).
Huo and Viola, "Substrate specificity and identification of functional groups of homoserine kinase from *Escherichia col*," *Biochemistry* 35(50):16180-16185 (1996).
Ibarra et al., "*Escherichia coli* K-12 undergoes adaptive evolution to achieve in silico predicted optimal growth," *Nature* 420(6912):186-189 (2002).
Ichikawa et al. "Catalytic reaction of 1,3-butanediol over solid acids," *J. Mol. Catalysis A Chem.* 256:106-112 (2006).
Ichikawa et al., "PIO study on 1,3-butanediol dehydration over CeO2 (1 1 1) surface," *J. Mol. Catalysis A Chem.* 231:181-189 (2005).
Iffland et al., "Directed molecular evolution of cytochrome c peroxidase," *Biochemistry* 39(25):10790-10798 (2000).
Ikai and Yamamoto, "Identification and Analysis of a Gene Encoding L-2,4-Diaminobutyrate:2-Ketoglutarate 4-Aminotransferase Invloved in the 1,3-Diaminopropane Production Pathway in *Acinetobacter baumanni*," *J. Bacteriol.* 179(16):5118-5125 (1997).
Imai and Ohno, "Measurement of yeast intracellular pH by image processing and the change it undergoes during growth phase," *J. Biotechnol.* 38:165-172 (1995).
Ingoldsby et al., "The discovery of four distinct glutamate dehydrogenase genes ina strain of *Halobacterium salinarum*," *Gene* 349:237-244 (2005).
Ishida et al., "Efficient production of L-Lactic acid by metabolically engineered *Saccharomyces cerevisiae* with a genome-integrated L-lactate dehydrogenase gene," *Appl. Environ. Microbiol.* 71:1964-1970 (2005).
Ishige et al., "Wax ester production from n-alkanes by *Acinetobacter* sp. strain M-1: ultrastructure of cellular inclusions and role of acyl coenzyme A reductase," *Appl. Environ. Microbiol.* 68(3):1192-1195 (2002).
Ismaiel et al., "Purification and characterization of a primary-secondary alcohol dehydrogenase from two strains of *Clostridium beijerinckii*," *J. Bacteriol.* 175(16):5097-5105 (1993).
Ismail et al., "Functional genomics by NMR spectroscopy Phenylacetate catabolism in *Escherichia coli*," *Eur. J. Biochem.* 270:3047-3054 (2003).
Ito et al., "D-3-hydroxybutyrate dehydrogenase from *Pseudomonas fragi*: molecular cloning of the enzyme gene and crystal structure of the enzyme," *J. Mol. Biol.* 355(4):722-733 (2006).
Iverson et al., "Structure of the *Escherichia coli* fumarate reductase respiratory complex," *Science* 284(5422):1961-1966 (1999).
Jacobi et al., "The hyp operon gene products are required for the maturation of catalytically active hydrogenase isoenzymes in *Escherichia coli*," *Arch. Microbiol.* 158:444-451 (1992).
Jeon et al., "Heterologous expression of the alcohol dehydrogenase (adhI) gene from *Geogacillus thermoglucosidaus* strain M10EXG," *J. Biotechnol.* 135:127-133 (2008).
Jesudason and Marchessault, "Synthetic Poly[(R,S)-.beta.-hydroxyalkanoates] with Butyl and Hexyl Side Chains," *Macromolecules* 27:2595-2602 (1994).
Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).
Jiang et al., "De novo computational design of retro-aldol enzymes," *Science* 319(5868):1387-1391 (2008).
Johnson et al., "Alteration of a single amino acid changes the substrate specificity of dihydroflavonol 4-reductase," *Plant J.* 25(3):325-333 (2001).
Johnston et al., "Complete nucleotide sequence of *Saccharomyces cerevisiae* chromosome VIII," *Science* 265:2077-2082 (1994).
Jojima et al., "Production of isopropanol by metabolically engineered *Escherichia coli*," *Appl. Microbiol. Biotechnol.* 77:1219-1224 (2008).
Jones and Woods, "Acetone-butanol fermentation revisited," *Microbiol. Rev.* 50(4):484-524 (1986).
Jones et al., "Purification and characterization of D-b-hydroxybutyrate dehydrogenase expressed in *Escherichia coli*," *Biochem. Cell Biol.* 71(7-8):406-410 (1993).
Kai et al., "Phosphoenolpyruvate carboxylase: three-dimensional structure and molecular mechanisms," *Arch. Biochem. Biophys.* 414:170-179 (2003).
Kanao et al., "Characterization of isocitrate dehydrogenase from the green sulfur bacterium *Chlorbium limicola*. A carbon dioxide-fixing enzyme in the reductive tricarboxylic acid cycle," *Eur. J. Biochem.* 269(7):1926-1931 (2002).

(56) References Cited

OTHER PUBLICATIONS

Kanao et al., "Kinetic and biochemical analyses on the reaction mechanism of a bacterial ATP-citrate lyase," *Eur. J. Biochem.* 269(14):3409-3416 (2002).

Kaneko et al., "Sequence analysis of the genome of the unicellular cyanobacterium *Synechocystis* sp. strain PCC6803, II. Sequence determination of the entire genome and assignment of potential protein-coding regions," *DNA Res.* 3:109-136 (1996).

Kapatral et al., "Genome Sequence and Analysis of the Oral Bacterium *Fusobacterium nucleatum* Strain ATCC 25586," *J. Bacteriol.* 184(7):2005-2018 (2002).

Kato et al., "Open reading frame 3 of the barotolerant bacterium strain DSS12 is complementary with cydD in *Escherichia coli*: cydD functions are required for cell stability at high pressure," *J. Biochem.* 120:301-305 (1996).

Kato et al., "Production of a novel copolyester of 3-hydroxybutyric acid with a medium-chain-length 3-hydroxyalkanoic acids by *Pseudomonas* sp. 61-3 from sugars," *Appl. Microbiol. Biotechnol.* 45:363-370 (1996).

Kazahaya et al, "Aerobic Dissimilation of Glucose by Heterolactic Bacteria," *J. Gen. Appl. Microbiol.* 18(1):43-55 (1972).

Kellum and Drake, "Effects of cultivation gas phase on hydrogenase of the acetogen *Clostridium thermoaceticum*," *J. Bacteriol.* 160:466-469 (1984).

Keng and Viola, "Specificity of Aspartokinase III from *Escherichia coli* and an Examination of Important Catalytic Residues," *Arch. Biochem. Biophys.* 335:73-81 (1996).

Kessler et al., "Pyruvate-formate-lyase-deactivase and acetyl-CoA reductase activities of *Escherichia coli* reside on a polymeric protein particle encoded by adhE," *FEBS.Lett.* 281:59-63 (1991).

Khan et al., "Molecular properties and enhancement of thermostability by random mutagenesis of glutamate ehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim and Tabita, "Both subunits of ATP-citrate lyase from *Chlorobium tepidum* contribute to catalytic activity," *J. Bacteriol.* 188(18):6544-6552 (2006).

Kim et al., "Construction of an *Escherichia coli* K-12 mutant for homoethanologenic fermentation of glucose or xylose without foreign genes," Appl. Environ. Microbiol 73:1766-1771 (2007).

Kim et al., "Dihydrolipoamide Dehydrogenase Mutation Alters the NADH Sensitivity of Pyruvate Dehydrogenase Complex of *Escherichi coli* K-12," *J. Bacteriol.* 190:3851-3858 (2008).

Kim et al., "Effect of overexpression of *Actinobacillus succinogenes* phosphoenolpyruvate carboxykinase on succinate production in *Escherichia coli*," *Appl. Environ. Microbiol.* 70:1238-1241 (2004).

Kim, "Purification and Propertis of a mine α-Ketoglutarate Transaminase from *Escherichia coli*," *J. Biol. Chem.* 239:783-786 (1964).

Kimura et al., "Production of Poly(3-hydroxybutyrate-co-4-hydroxybutyrate) by *Pseudomonas acidovorans*," *Biotechnol. Lett.* 14(6):445-450 (1992).

Kinnaird et al., "The complete nucleotide sequence of the *Neurospora crassa* am (NADP-specific glutamate dehydrogenase) gene," *Gene* 26:253-260 (1983).

Kino et al., "Synthesis of DL-tryptophan by modified broad specificity amino acid racemase from *Pseudomonas putida* IFO 12996," *Appl. Microbiol. Biotechnol.* 73(6):1299-1305 (2007).

Kinoshita, "Purification of two alcohol dehydrogenases from *Zymomonas mobilis* and their properties," *Appl. Microbiol. Biotechnol.* 22:249-254 (1985).

Kirby et al., "Purification and properties of rabbit brain and liver 4-aminobutyrate aminotransferases isolated by monoclonal-antibody Immunoadsorbent chromatography," *Biochem. J.* 230:481-488 (1985).

Klasson et al., "Biological conversion of coal and coal-derived synthesis gas," *Fuel* 72:1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9(8):2067-2078 (2007).

Klenk et al., "The complete genome sequence of the hyperthermophilic, sulphate-reducing archaeon *Archaeoglobus fulgidus*," *Nature* 390:364-370 (1997).

Knapp et al., "Crystal Structure of the Truncated Cubic Core Component of the *Escherichia coli* 2-Oxoglutarate Dehydrogenase Multienzyme Complex," *J. Mol. Biol.* 289:655-668 (1998).

Knappe and Sawers, A radical-chemical route to acetyl-CoA: the anaerobically induced pyruvate formate-lyase system of *Escherichia coli*, FEMS Microbiol. Rev. 75:383-398 (1990).

Kobayashi et al., "Physiochemical, Catalytic, and Immunochemical Properties of Fumarases Crystallized Separately from Mitochondrial and Cytosolic Fractions of Rat Liver," *J. Biochem.* 89:1923-1931 (1981).

Koland and Gennis, "Proximity of rreactive cysteine residue and flavin in *Escherichia coli* pyruvate oxidase as estimated by fluorescence energy transfer," *Biochemistry* 21(18):4438-4442 (1982).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Korbert et al., "Crystallization of the NADP+-dependent Glutamate Dehydrogenase from *Escherichia coli*," *J. Mol. Biol.* 234:1270-1273 (1993).

Korolev et al., "Autotracing of *Escherichia coli* acetate CoA-transferase α-subunit structure using 3.4 Å MAD and 1.9 Å native data," *Acta. Cryst.* D58:2116-2121 (2002).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kreimeyer et al., "Indentification of the Last Unknown Genes in the fermentation Pathway of Lysine," *J. Biol. Chem.* 282:7191-7197 (2007).

Kretz et al., "Gene site saturation mutagenesis: a comprehensive mutagenesis approach," *Methods Enzymol.* 388:3-11 (2004).

Krieger et al., "Pyruvate decarboxylase from *Kluyveromyces lactis* an enzyme with an extraordinary substrate activation behaviour," *Eur. J. Biochem.* 269:3256-3263 (2002).

Kumamaru et al., "Enhanced degradation of polychlorinated biphenyls by directed evolution of biphenyl dioxgenase," *Nat. Biotechnol.* 16(7)663-666 (1998).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kunioka et al., "New bacterial copolyesters produced in *Alcaligenes eutrophus* from organic acids," *Polym. Commun.* 29:174-176 (1988).

Kurihara et al., "A Novel Putrescine Utilization Pathway Involves γ-Glutamylated Intermediates of *Escherichia coli* K-12," *J. Biol. Chem.* 280(6) 4602-4608 (2005).

Kuznetsova et al., "Enzyme genomics: Application of general enzymatic screens to discover new enzymes," *FEMS Microbiol. Rev.* 29:263-279 (2005).

Kwok and Hanson, "GFP-labelled Rubisco and aspartate aminotransferase are present in plastid stromules and traffic between plastids," *J. Experi. Bot.* 55:(397)595-604 (2004).

Kwon et al., "Brain 4-aminobutyrate aminotransferase. Isolation and sequence of a cDNA encoding the enzyme," *J. Biol. Chem.* 267:7215-7216 (1992).

Kwon et al., "Influence of gluconeogenic phosphoenolpyruvate carboxykinase (PCK) expression on succinic acid fermentation in *Escherichia coli* under high bicarbonate condition," *J. Microbiol. Biotechnol.* 16(9):1448-1452 (2006).

(56) References Cited

OTHER PUBLICATIONS

Lageveen, et al., "Formation of Polyesters by *Pseudomonas oleovorans*: Effect of Substrates on Formation and Composition of Poly-(R)-3-Hydroxyalkanoates and Poly-(R)-3-Hydroxyalkenoates," *Appl. Environ. Microbiol.* 54:2924-2932 (1988).

Laivenieks et al., "Cloning sequencing, and overexpression of the *Anaerobiospirillum succinicproducens* phosphoenolpyruvate carboxykinase (pckA) gene," *Appl. Environ. Microbiol.* 63:2273-2280 (1997).

Lam and Winkler, "Metabolic Relationships between Pyridoxine (vitamin $B_6$) and Serine Biosynthesis in *Escherichia coli* K-12," *J. Bacteriol.* 172(11):6518-6528 (1990).

Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395:147-155 (2006).

Lamed and Zeikus, "Novel NAP-linked alcohol-aldehyde/ketone oxidoreductase in thermophilic ethanologenic bacteria," *Biochem. J.* 195:183-190 (1981).

Lebbink et al., "Engineering activity and stability of *Thermotoga maritima* Glutamate Dydrogenase. I. Introduction of a Six-residue Ion-pair Network in the Hinge Region," *J. Mol. Biol.* 280:287-296 (1998).

Lebbink et al., "Engineering activity and stability of *Thermotoga maritima* glutamate dehydrogenase. II: construction of a 16-residue ion-pair network at the subunit interface," *J. Mol. Biol.* 289(2):357-369 (1999).

Leduc et al., "The Hotdog Thiesterase EntH (YbdB) Plays a Role in Vivo in Optimal Enterobactin biosynthesis by Interacting with the ArCP Domain of EntB," *J. Bacteriol.* 189(19):7112-7126 (2007).

Lee and Cho, "Identification of essential active-site residues in ornithine decarboxylase of *Nicotiana glutinosa* decarboxylating both L-ornithine and L-lysine," *Biochem. J.* 360(Pt 3):657-665 (2001).

Lee et al., "Biosynthesis of enantiopure (s)-3-hydroxybutyric acid in metabolically engineered *Escherichia coli*," *Appl. Microbiol. Biotechnol.* 79(4):633-641 (2008).

Lee et al., "Cloning and Characterization of Mannheimia succiniciproducens MBEL55E Phosphoenolpyruvate Carboxykinase (pckA) Gene," *Biotechnol. Bioprocess Eng.* 7:95-99 (2002).

Lee et al., "Phylogenetic diversity and the structural basis of substrate specificity in the beta/alpha-barrel fold basic amino acid decarboxylases," *J. Biol. Chem.* 282(37):27115-27125 (2007).

Lee et al., "A new approach to directed gene evolution by recombined extension on truncated templates (RETT)," *J. Molec. Catalysis* 26:119-129 (2003).

Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," *Appl. Microbiol. Biotechnol.* 42: 901-909 (1995).

Lee et al., "Enhanced biosynthesis of P(3HB-3HV) and P(3HB-4HB) by amplification of the cloned PHB biosynthesis genes in *Alcatigenes eutrophus*," *Biotechnol. Lett.* 19:771-774 (1997).

Lemoigne and Rouklehman, "Fermentation b-Hydroxybutyrique," *Annales des Fermentations* 5:527-536 (1925).

Lemonnier and Lane, "Expression of the second lysine decarboxylase gene of *Escherichia coli*," *Microbiology* 144(Pt 3):751-760 (1998).

Lepore et al., "The x-ray crystal structure of lysine-2,3-aminomutase from *Clostridium subterminale*," *Proc. Natl. Acad. Sci. U.S.A.* 102:13819-13824 (2005).

Lessner et al., "An unconventional pathway for reduction of $CO_2$ to methane in CO-grown *Methanosarcina acetivorans* revealed by proteomics," *Proc. Natl. Acad. Sci. U.S.A.* 103:17921-17926 (2006).

Li and Jordan, "Effecrts of Substitution of Tryptophan 412 in the Substrate Activation Pathway of Yeast Pyruvate Decarboxylase," *Biochemistry* 38:10004-10012 (1999).

Li et al., "Properties of Nicotinamide Adenine Dinucleotide Phosphate-Dependent Formate Dehydrogenase from *Clostridium thermoaceticum*," *J.Bacteriol.* 92:405-412 (1966).

Li, Guang-Shan, "Development of a reporter system for the study of gene expression for solvent production in *Clostridium beijerinckii* NRRL B592 and *Clostridium acetobutylicum* ATCC 824," Dissertation, Department of Biochemestry, Virginia Polytechnic Institute and State University (Sep. 1998).

Lian and Whitman, "Sterochemical and Isotopic Labeling Studies of 4-Oxalocrotonate Decarboxylase and Vinylpyruvate Hydratase: Analysis and Mechanistic Implications," *J. Am. Chem. Soc.* 116:10403-10411 (1994).

Liebergesell and Steinbuchel, "Cloning and nucleotide sequences of genes relevant for biosynthesis of poly(3-hydroxybutyric acid) in *Chromatium vinosum* strain D," *Eur. J. Biochem.* 209(1):135-150 (1992).

Lin et al., "Fed-batch culture of a metabolically engineered *Escherichia coli* strain designed for high-level succinate production and yield under aerobic conditions," *Biotechnol. Bioeng.* 90(6):775-779 (2005).

Lin et al., "Functional expression of horseradish peroxidase in *E. coli* by directed evolution," *Biotechnol. Prog.* 15(3):467-471 (1999).

Lingen et al., "Alteration of the Substrate Specificity of Benzoylformate Decarboxylase from *Pseudomonas putida* by Directed Evolution," *Chembiochem* 4:721-726 (2003).

Lingen et al., "Improving the carboligase activity of benzoylformate decarboxylase from *Pseudomonas putida* by a combination of directed evolution and site-directed mutagenesis," *Protein Eng.* 15:585-593 (2002).

Link et al., "Methods for generating precise deletions and insertions in the genome of wild-type *Escherichia coli*: application to open reading frame characterization," *J. Bacteriol.* 179:6228-6237 (1997).

Liu and Steinbuchel, "Exploitation of butyrate kinase and phosphotransbutyrylase from *Clostridium acetobutylicum* for the in vitro biosynthesis of poly (hydroxyalkanoic acid)," *Appl. Microbiol. Biotechnol.* 53(5):545-552 (2000).

Liu et al., "Crystal Structures of Unbound and Aminoxyacetate-Bound *Eschericiha coli* Y-Aminobutyrate Aminotransferase," *Biochem.* 43:10896-10905 (2004).

Liu et al., "Kinetic and crystallographic analysis of active site mutants of *Escherichia coli* gamma-aminobutyrate aminotransferase," *Biochemistry* 44:(8):2982-2992 (2005).

Ljungdahl and Andreesen, "Formate dehydrogenase, a selenium—tungsten enzyme from *Clostridium thermoaceticum*," *Methods Enzymol.* 53:360-372 (1978).

Ljungdahl et al., "Tungsten, a component of active formate dehydrogenase from *Clostridium thermoacetium*," *FEBS Lett.* 54:279-282 (1975).

Lokanath et al., "Crystal Structure of novel NADP-dependent 3-Hydroxyisobutyrate Dehydrogenase from *Thermus thermophilus* HB8," *J. Mol Biol.* 352:905-917 (2005).

Louie and Chan, "Cloning and characterization of the gamma-glutamyl phosphate reductase gene of *Campylobacter jejuni*," *Mol. Gen. Genet.* 240:29-35 (1993).

Louis et al., "Restricted Distribution of the Butyrate Kinase Pathway among Butyrate-Producing Bacteria from the Human Colon," *J. Bacteriol.* 186(7):2099-2106 (2004).

Lovell et al., "Cloning and expression in *Escherichia coli* of the *Clostridium thermoaceticum* gene encoding thermostable formyltetrahydrofolate synthetase," *Arch. Microbiol.* 149:280-285 (1988).

Lovell et al., "Primary structure of the thermostable formyltetrahydrofolate synthetase from *Clostridium thermoaceticum*," *Biochemistry* 29:5687-5694 (1990).

Low et al., "Mimicking somatic hypermutation: affinity maturation of antibodies displayed on bacteriophage using a bacterial mutator strain," *J. Mol. Biol.* 260(3):359-368 (1996).

Lu et al, "Functional analysis and regulation of the divergent SpuABCDEFG-spuI operons for polyamine uptake and utilization in *Pseudomonas aeruginosa* PA01," *J. Bacteriol.* 184:3765-3773 (2002).

(56) References Cited

OTHER PUBLICATIONS

Lu et al., "Sequence and expression of the gene encoding the corrinoid/iron-sulfur protein from *Clostridium thermoaceticum* and reconstitution of the recombinant protein to full activity," *J. Biol. Chem.* 268:5605-5614 (1993).
Lu et al., "Enhanced production of poly(3-hydroxybutyrate-co-3-hydroxyhexanoate) via manipulating the fatty acid beta-oxidation pathway in *E. coli,*" *FEMS Microbiol. Lett.* 221(1):97-101 (2003).
Lu et al., "Molecular cloning of polyhydroxyalkanoate synthesis operon from *Aeromonas hydrophilia* and its expression in *Escherichia coli,*" *Biotechnol. Prog.* 20(5):1332-1336 (2004).
Lutke-Eversloh and Steinbuchel, "Biochemical and molecular characterization of a succinate semialdehyde dehydrogenase involved in the catabolism of 4-hydroxybutyric acid in *Ralstonia eutropha,*" *FEMS Microbiol. Lett.* 181:63-71 (1999).
Lutz and Bujard, "Independent and tight regulation of transcriptional units in *Escherichia coli* via the LacR/O, the TetR/O and AraC/I1-I2 regulatory elements," *Nucleic Acids Res.* 25:1203-1210 (1997).
Lutz et al., "Creating multiple-crossover DNA libraries independent of sequence identity," *Proc. Natl. Acad. Sci. U.S.A.* 98(20):11248-11253 (2001).
Lutz et al., "Rapid generation of incremental truncation libraries for protein engineering using α-phosphothioate nucleotides," *Nucleic Acids Res.* 15:29(4):e16 (2001).
Ma et al., "Induced Rebuilding of Aspartase Confromation," *Ann. N.Y. Acad. Sci.* 672:60-65 (1992).
Mack and Buckel, "Conversion of glutaconate CoA-transferase from *Acidaminococcus fermentas* into an acyl-CoA hydrolase by site-directed mutagenesis," *FEBS Lett.* 405:209-212 (1997).
Mack et al., "Location of the two genes encoding glutaconate coenzyme A-transferase at the beginning of the hydroxyglutarate operon in *Acidaminococcus fermentans,*" *Eur. J. Biochem.* 226:41-51 (1994).
Maeder et al., "The *Methanosarcina barkeri* genome: comparative analysis with *Methanosarcina acetivorans* and *Methanosarcina mazei* reveals extensive rearrangement within methanosarcinal genomes," *J. Bacteriol.* 188:7922-7931 (2006).
Mahadevan and Schilling, "The effects of alternate optimal solutions in constraint-based genome-scale metabolic models," *Metab. Eng.* 5(4):264-276 (2003).
Mahadevan et al., "Application of metabolic modeling to drive bioprocess development for the production of value-added chemicals," *Biotechnol. Bioprocess Eng.* 10(5):408-417 (2005).
Mahan and Csonka, "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.* 156(3):1249-1262 (1983).
Majewski and Domach, "Simple Constrained-Optimization View of Acetate Overflow in *E. coli,*" *Biotech. Bioeng.* 35:732-738 (1990).
Majumdar et al., "Functional consequences of substitution in the active site (phosphor) histidine residue of *Escherichia coli* succinyl-CoA synthetase," *Biochim. Biophys. Acta.* 1076:86-90 (1991).
Mandal and Ghosh, "Isolation of a glutamate synthase (GOGAT)-negative, pleiotropically N utilization-defective mutant of *Azospirillum brasilense*: cloning and partial characterization of GOGAT structural gene," *J. Bacteriol.* 175:8024-8029 (1993).
Manning and Pollitt, "Tracer studies of the interconversion of R- and S-methylmalonic semialdehydes in man," *Biochem. J.* 231:481-484 (1985).
Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).
Marek and Henson, "Cloning and expression of the *Escherichia coli* K-12 sad gene," *J. Bacteriol.* 170(2):991-994 (1988).
Marks et al., "Molecular Cloning and Characterization of (R)-3-Hydroxybutyrate Dehydrogenase from Human Heart," *J. Biol. Chem.* 267:15459-15463 (1992).

Martin et al., "Engineering a mevalonate pathway in *Escherichia coli* for production of terpenoids," *Nat. Biotechnol.* 21:796-802 (2003).
Martinez-Blanco et al., "Purification and Biochemical Characterization of Phenylacetyl-CoA Ligase from *Pseudomonas putida,*" *J. Biol. Chem.* 265(12):7084-7090 (1990).
Mat-Jan et al., "Anaerobic growth defects resulting from gene fusions affecting succinyl-CoA synthetase in *Escherichia coli* K12," *Mol. Gen. Genet.* 215:276-280 (1989).
Mattevi et al., "Atomic structure of the cubic core of the pyruvate dehydrogenase multienzyme complex," *Science* 255:1544-1550 (1992).
Matthies and Schink, "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.* 58(5):1435-1439 (1992).
Mavrovouniotis, "Estimation of standard Gibbs energy changes of biotransformations," *J. Biol. Chem.* 266:14440-14445 (1991).
McKinlay et al., "Prospects for a bio-based succinate industry," *Appl. Microbiol. Biotechnol.* 76(4):727-740 (2007).
McLaggan et al., "Interdependence of K+ and glutamate accumulation during osmotic adaptation of *Escherichia coli,*" *J. Biol. Chem.* 269:1911-1917 (1994).
McPherson and Wootton, "Complete nucleotide sequence of the *Escherichia coli* gdhA gene," *Nucleic Acids Res.* 11(15):5257-5266 (1983).
Melchiorsen et al., "The level of pyruvate-formate lyase controls the shift from homolactic to mixed-acid product formation in *Lactoccus lactis,*" *Appl. Microbiol. Biotechnol.* 58(3):338-344 (2002).
Meng and Chuang, "Site-Directed Mutagenesis and functional Analysis of the Active-Site Residues of the E2 Component of Bovine Branched-Chain α-Keto Acid Dehydrogenase Complex," *Biochem.* 33:12879-12885 (1994).
Menon and Ragsdale, "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36:8484-8494 (1997).
Menzel et al., "Enzymatic evidence for an involvement of pyruvate dehydrogenase in the anaerobic glycerol metabolism of *Klebsiella pneumoniae,*" *J. Biotechnol.* 56:135-142 (1997).
Menzel et al., "Kinetic, dynamic, and pathway studies of glycerol metabolism by *Klebsiella pneumoniae* in anaerobic continuous culsutre: IV. Enzynmes and fluxes of pyruvate metabolism," *Botechnol. Bioeng.* 60(5):617-626 (1998).
Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).
Metz et al., "Purification of a jojoba embryo fatty acyl-coenzyme A reductase and expression of its cDNA in high erucic acid rapeseed," *Plant Physiol.* 122(3):635-644 (2000).
Metzer and Halpern, "In vivo cloning and characterization of the gabCTDP gene cluster of *Escherichia coli* K-12," *J. Bacteriol.* 172:3250-3256 (1990).
Metzer et al., "Isolation and properties of *Escherichia coli* K-12 mutants impaired in the utilization of gamma-aminobutyrate," *J. Bacteriol.* 137(3):1111-1118 (1979).
Miles and Guest, "Molecular genetic aspects of the citric acid cycle of *Escherichia coli,*" *Biochem. Soc. Symp.* 54:45-65 (1987).
Miller and Brenchly, "Cloning and characterization of gdhA, the structural gene for glutamate dehydrogenase of *Salmonella typhimurium,*" *J. Bacteriol.* 157:171-178 (1984).
Minard and McAlister-Henn, "Isolation, Nucleotide Sequence Analysis, and Disruption of theMDH2 Gene from *Saccharomyces cerevisiae*: Evidence for Three Isozymes of Yeast Malate Dehydrogenase," *Mol. Cell. Biol.* 11(1):370-380 (1991).
Misono and Nagasaki, "Occurrence of L-Lysine ε-Dehydrogenase in *Agrobacterium tumefaciens,*" *J. Bacteriol.* 150(1):398-401 (1982).
Miyamoto and Katsuki, "Possible physiological roles of aspartase, NAD- and NADP-requiring glutamate dehydrogenases of *Pseudomonas fluorescens,*" *J. Biochem.* 112:52-56 (1992).

(56) References Cited

OTHER PUBLICATIONS

Miyazaki et al., "α-Aminoadipate aminotransferase from an extremely thermophilic bacterium, *Thermus thermophilus*," *Microbiology* 150:2327-2334 (2004).
Mizobata et al., "Purification and Characterization of a thermostable Class II Fumarase from *Thermus thermophilus*," *Arch. Biochem. Biophys.* 355:49-55 (1998).
Momany et al., "Crystallographic Structures of a PLP-Dependent Ornithine Decarboxylase from *Lactobacillus* 30a to 3.0 Å Resolution," *J. Mol. Biol.* 242:643-655 (1995).
Monnet et al., "Regulation of branched-chain amino acid biosynthesis by α-acetolactate decarboxylase in *Streptococcus thermophilus*," *Lett. Appl. Microbiol.* 36(6):399-405 (2003).
Moore et al., "Expression and Purification of Aspartate β-Semialdehyde Dehydrogenase from Infectious Microorganisms," *Protein Expr. Purif.* 25:189-194 (2002).
Morris et al., "Nucleotide sequence of the LYS2 gene of *Saccharomyces cerevisiae*: homology to *Bacillus brevis* tyrocidine synthetase1," *Gene* 98:141-145 (1991).
Morton et al., "Cloning, sequencing, and expression of genes encoding enzymes of the autotrophic acetyl-CoA pathway in the acetogen *Clostridium thermoaceticum*," In M. Sebald (ed.), *Genetics and molecular biology of anaerobic bacteria*. Springer Verlag, New York, p. 389-406 (1992).
Morton et al., "The primary structure of the subunits of carbon monoxide dehydrogenase/acetyl-CoA synthase from *Clostridium thermoaceticum*," *J. Biol. Chem.* 266:23824-23828 (1991).
Mountain et al., "The *Klebsiella aerogenes* glutamate dehydrogenase (gdnA) gene: cloning, high-level expression and hybrid enzyme formation in *Escherichia coli*," *Mol. Gen. Genet.* 199:141-145 (1985).
Muh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).
Muh et al., "Mossbauer study of 4-hydroxybutyryl-CoA dehydratase—probing the role of an iron-sulfur cluster in an overall non-redox reaction," *Eur. J. Biochem.* 248:380-384 (1997).
Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta* 1475(3):191-206 (2000).
Muller et al., "Nucleotide exchange and excision technology (NExT) DNA shuffling: a robust method for DNA fragmentation and directed evolution," *Nucleic Acids Res.* 33(13):e117 (2005).
Muller, "Energy conservation in acetogenic bacteria," *Appl. Environ. Microbiol.* 69:6345-6353 (2003).
Muratsubaki and Enomoto, "One of the fumarate reductase isoenzymes from *Saccharomyces cerevisiae* is encoded by the OSM1 gene," *Arch. Biochem. Biophys.* 352(2):175-181 (1998).
Musfeldt and Schonheit, "Novel Type of ADP-Forming Acetyl Coenzyme A Synthetase in Hyperthermophilic Archaea: Heterologous Expression and Characterization of Isoenzymes from the Sulfate Reducer *Archaeoglobus fulgidus* and the Methanogen *Methanococcus jannaschii*," *J. Bacteriol.* 184(3):636-644 (2002).
Muyrers et al., "Rapid modification of bacterial artificial chromosomes by ET-recombination," *Nucleic Acids Res.* 27:1555-1557 (1999).
Nagasu et al., "Nucleotide Sequence of the GDH gene coding for the NADP-specific glutamate dehydrogenase of *Saccharomyces cerevisiae*," *Gene* 37:247-253 (1985).
Naggert et al., "Cloning, Sequencing, and Characterization of *Escherichia coli* thioesterasell," *J. Biol. Chem.* 266(17):11044-11050 (1991).
Nahvi et al., "Genetic control by a metabolite binding mRNA," *Chem. Biol.* 9:1043-1049 (2002).
Naidu and Ragsdale, "Characterization of a three-component vanillate O-demethylase from *Moorella thermoacetica*," *J. Bacteriol.* 183:3276-3281 (2001).
Najafpour and Younesi, "Ethanol and acetate synthesis from waste gas using batch culture of *Clostridium ljungdahlii*," *Enzyme Microb. Tech.* 38:223-228 (2006).
Najmudin et al., "Purification, crystallization and preliminary X-ray crystallographic studies on acetolactate decarboxylase," *Acta. Crystallogr. D. Biol. Crystallog.* 59:1073-1075 (2003).
Nakahigashi and Inokuchi, "Nucleotide sequence of the fadA and fadB genes from *Escherichia coli*," *Nucleic Acids Res.* 18(16):4937 (1990).
Nakano et al., "Characterization of Anaerobic Fermentative Growth of *Bacillus subtilis*: Identification of Fermentation End Products and Genes Required for Growth," *J. Bacteriol.* 179(21):6749-6755 (1997).
Namba et al., "Coenzyme A and Nicotinamide Adenine dinucleotide-deptendent Branched Chain α-Keto Acid Dehydrogenase," *J. Biol. Chem.* 244:4437-4447 (1969).
Ness et al., "Synthetic shuffling expands functional protein diversity by allowing amino acids to recombine independently," *Nat. Biotechnol.* 20(12):1251-1255 (2002).
Nexant, "1,4-Butanediol/THF—PERP Program New Report Alert," Nexant ChemSystems PERP Report 02/03-7, p. 1-5 (Jan. 2004).
Niegemann et al., "Molecular organization of the *Escherichia coli* gab cluster: nucleotide sequence of the structural genes gabD and gabP and expression of the GABA permease gene," *Arch. Microbiol.* 160:454-460 (1993).
Nimmo, "Kinetic mechanism of *Escherichia coli* isocitrate dehydrogenase and its inhibition by glyoxylate and oxaloacetate," *Biochem. J.* 234(2):317-323 (1986).
Nishizawa et al., "Gene expression and characterization of two 2-oxoacid:ferredoxin oxidoreductases from *Aeropyrum pernix* K1," *FEBS. Lett.* 579:2319-2322 (2005).
Niu, et al., "Benzene-free synthesis of adipic acid," *Biotechnol. Prog.* 18:201-211 (2002).
Nolling et al., "Genome sequence and comparative analysis of the solvent-producing bacterium *Clostridium acetobutylicum*," *J. Bacteriol.* 183(16):4823-4838 (2001).
Nowicki et al., "Recombinant tyrosine aminotransferase from *Trypanosoma cruzi*: structural characterization and site directed mutagenesis of a broad substrate specificity enzyme," *Biochim. Biophys. Acta* 1546(2):268-281 (2001).
O'Brien and Gennis, "Studies of the thiamin pyrophosphate binding site of *Escherichia coli* pyruvate oxidase. Evidence for an essential tryptophan residue," *J. Biol. Chem.* 255(8):3302-3307 (1980).
O'Brien et al., "Chemical, physical and enzymatic comparisons of formyltetrahydrofolate synthetases from thermo- and mesophilic *Clostridia*," *Experientia. Suppl.* 26:249-262 (1976).
O'Brien et al., "Regulation by lipids of cofactor binding to a peripheral membrane enzyme: binding of thiamin pyrophosphate to pyruvate oxidase," *Biochemistry* 16(14)3105-3109 (1977).
Ohgami et al., "Expression of acetoacetyl-CoA synthetase, a novel cytosolic ketone body-utilizing enzyme, in human brain," *Biochem. Pharmacol.* 65:989-994 (2003).
Ohsugi et al., "Metabolism of L-β-Lysine by a *Pseudomonas*, Purification and Properties of a Deacetylase-Thiolesterase utilizing 4-Acetamidobutyrl CoA and Related Compounds," *J. Biol. Chem.* 256:7642-7651 (1981).
Okino et al., "An efficient succinic acid production process in a metabolically engineered *Corynebacterium glutamicum* strain," *Appl. Microbiol. Biotechnol.* 81(3):459-464 (2008).
Oku and Kaneda, "Biosynthesis of Branched-chain Fatty Acids in *Bacillis subtilis*," *J. Biol. Chem.* 263:18386-18396 (1988).
Okuno et al., "2-Aminoadipate-2-oxoglutarate aminotransferase isoenzymes in human liver: a plausible physiological role in lysine and tryptophan metabolism," *Enzyme Protein* 47(3):136-148 (1993).
Oliver et al., "Determination of the nucleotide sequence for the glutamate synthase structural genes of *Escherichia coli* K-12," *Gene* 60:1-11 (1987).
Olivera et al., "Molecular characterization of the phenylacetic acid catabolic pathway in *Pseudomonas putida* U: The phenylacetyl-CoA catabolon," *Proc. Natl. Acad. Sci. U.S.A.* 95:6419-6424 (1998).
Onuffer and Kirsch, "Redesign of the substrate specificity of *Escherichia coli* aspartate aminotransferase to that of *Escherichia*

(56) References Cited

OTHER PUBLICATIONS

*coli* tyrosine aminotransferase by homology modeling and site-directed mutagenesis," *Protein Sci.* 4:1750-1757 (1995).
O'Reilly and Devine, "Sequence and analysis of the citrulline biosynthetic operon argC-F from *Bacillus subtilis,*" *Microbiology* 140:1023-1025 (1994).
Orencio-Trejo et al., "Metabolic regluation analysis of an ethanologenic *Escherichia coli* strain based on RT-PCR and enzymatic activities," *Biotechnol. Biofuels* 1:8 (2008).
Ostermeier et al., "A combinatorial approach to hybrid enzymes independent of DNA homology," *Nat. Biotechnol.* 17(12):1205-1209 (1999).
Ostermeier et al., "Combinatorial protein engineering by incremental truncation," *Proc. Natl. Acad. Sci. U.S.A.* 96(7):3562-3567 (1999).
O'Sullivan, et al., "Purification and characterisation of acetolactate decarboxylase from Leuconostoc lactis NCW1," *FEMS Microbiol. Lett.* 194(2):245-249 (2001).
Otten and Quax, "Directed evolution: selecting today's biocatalysts," *Biomol. Eng.* (22):1-9 (2005).
Palosaari and Rogers, "Purification and properties of the inducible coenzyme A-linked butyraldehyde dehydrogenase from *Clostridium acetobutylicum,*" *J. Bacteriol.* 170(7):2971-2976 (1988).
Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).
Park and Lee, "Identification and Characterization of a New Enoyl coenzyme A Hydratase involved in biosynthesis of Medium-Chain-Length Polyhdroxyalkanoates in recombinant *Escherichia coli,*" *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli,*" *Biotechnol. Bioeng.* 86:681-686 (2004).
Park et al., "Regulation of succinate dehydrogenase (sdhCDAB) operon expression ion *Escherichia coli* in response to carbon supply and anaerobiosis: role of ArcA and Fnr," *Mol. Micriobiol.* 15:473-482 (1995).
Park et al., "Aerobic regulation of the sucABCD genes of *Escherichia coli,* which encode alpha-ketoglutarate dehydrogenase and succinyl coenzyme A synthetase: roles of ArcA, Fnr, and the upstream sdhCDAB promoter," *J. Bacteriol.* 179:4138-4142 (1997).
Park et al., "Isolation and characterization of recombinant mitochondrial 4-aminobutyrate aminotransferase," *J. Biol. Chem.* 268:7636-7639 (1993).
Parkin et al., "Rapid and efficient electrocatalytic CO2/CO interconversions by *Carboxydothermus hydrogenoformans* CO dehydrogenase I on an electrode," *J. Am. Chem. Soc.* 129:10328-10329 (2007).
Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene.* 68(2): 275-283 (1988).
Pauwels et al., "The N-acetylglutamate synthase?N-acetylglutamate kinase metabolon of *Saccharomyces cerevisiae* allows cor-ordinated feedback regulation of the first two steps in arginine biosynthesis," *Eur. J. Biochem.* 270:1014-1024 (2003).
Paxton et al., "Role of branched-chain 2-oxo acid dehydrogenase and pyruvate dehydrogenase in 2-oxobutyrate metabolism," *Biochem. J.* 234:295-303 (1986).
Pelanda et al., "glutamate synthase genes of the diazotroph *Azospirillum brasillense.* Cloning, sequencing, and analysis of functional domains," *J. Biol. Chem.* 268:3099-3106 (1993).
Peoples and Sinskey, "Fine structural analysis of the Zoogloea ramigera phhA-phhB locus encoding beta-ketothiolase and acetoacetyl-CoA reductase: nucleotide sequence of phbB," *Mol. Microbiol.* 3:349-357 (1989).
Pereira et al., "Active site mutants of *Escherichia coli* citrate synthase. Effects of mutations on catalytic and allosteric properties," *J. Biol. Chem.* 269:412-417 (1994).

Peretz and Burstein, "Amino Acid Sequence of Alcohol Dehydrogenase from the Thermophilic Bacterium *Thermoanaerobium brockii,*" *Biochem.* 28:6549-6555 (1989).
Peretz et al., "Molecular cloning, nucleotide sequencing, and expression of genes encoding alcohol dehydrogenases from the thermophile *Thermoanaerobacter brockii* and the mesophile *Clostridium beijerinckii,*" *Anaerobe* 3:259-270 (1997).
Perez et al., "*Escherichia coli* YqhD exhibits aldehyde reductase activity and protects from the harmful effect of lipid peroxidation-derived aldehydes," *J. Biol. Chem.* 283(12);7346-7353 (2008).
Petersen and Bennett, "Purification of acetoacetate decarboxylase from *Clostridium acetobutylicum* ATCC 824 and cloning of the acetoacetate decarboxylase gene in *Escherichia coli,*" *Appl. Environ. Microbiol.* 56:3491-3498 (1990).
Petitdemange et al., "Regulation of the NADH and NADPH-ferredoxin oxidoreductases in clostridia of the butyric group," *Biochim. Biophys. Acta.* 421(2):334-337 (1976).
Phalip et al., "Purification and properties of the alpha-acetolactate decarboxylase from *Lactococcus lactis* subsp. Lactis NCDO 2118," *FEBS Lett.* 351:95-99 (1994).
Pharkya et al., "Exploring the overproduction of amino acids using the bilevel optimization framework OptKnock," *Biotechnol. Bioeng.* 84(7):887-899 (2003).
Pierce et al.,"The complete genome sequence of *Moorella thermoacetia* (f. *Clostridium thermoaceticum*)," *Environ. Microbiol.* 10(10):2550-2573 (2008).
Pieulle, "Isolation and analysis of the gene encoding the pyruvate-ferredoxin oxidoreductase of *Desulfovibrio africanus,* production of the recombinant enzyme in *Escherichia coli,* and effect of carboxy-terminal deletions on its stability," *J. Bacteriol.* 179:5684-5692 (1997).
Ploux et al., "The NADPH-linked acetoacetyl-CoA reductase from *Zoogloea ramigera,* Characterization and mechanistic studies of the cloned enzyme over-produced in *Escherichia coli,*" *Eur. J. Biochem.* 174:177-182 (1988).
Pohl et al., "Remarkably broad substrate tolerance of malonyl-CoA synthetase, an enzyme capable of intracellular synthesis of polyketide precursors," *J. Am. Chem Soc.* 123(24): 5822-5823 (2001).
Pohlmann et al., "Genome sequence of the bioplastic-producing "Knallgas" bacterium *Ralstonia eutropha* H16," *Nat. Biotechnol.* 24(10):1257-1262 (2006).
Poirier et al., "Polyhydroxybutyrate, a Biodegradable Thermoplastic Produced in Transgenic Plants," *Science* 256:520-523 (1992).
Polovnikova et al., "Structural and Kinetic Analysis of Catalysis by a thiamin diphosphate-Dependent Enzyme, Benzoylformate Decarboxylase " *Biochemistry* 42:1820-1830 (2003).
Poston, "Assay of leucine 2,3-aminomutase," *Methods Enzymol.* 166:130-135 (1988).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175:377-385 (1993).
Presecan et al., "The *Bacillus subtillis* genome from gerBC (311 degrees) to licR (334 degrees)," *Microbiology* 143:3313-3328 (1997).
Price et al., "Genome-scale models of microbial cells: evaluating the consequences of constraints," *Nat. Rev. Microbiol.* 2(11):886-897 (2004).
Pritchard et al., "A general model of error-prone PCR," *J. Theor. Biol.* 234:497-509 (2005).
Pritchett and Metcalf, "Genetic, physiological and biochemical characterization of multiple methanol methyltransferase isozymes in *Methanosarcina acetivorans* C2A," *Mol. Microbiol.* 56:1183-1194 (2005).
Purnell et al., "Modulation of higher-plant NAD(H)-dependent glutamate dehydrogenase activity in transgenic tobacco via alteration of beta subunit levels," *Planta* 222:167-180 (2005).
Qi et al., "Functional expression of prokaryotic and eukaryotic genes in *Escherichia coli* for conversion of glucose to *p*-hydroxystyrene," *Metab. Eng.* 9:268-276 (2007).

(56) References Cited

OTHER PUBLICATIONS

Qian et al., "Metabolic engineering of *Escherichia coli* for the production of putrescine: a four carbon diamine," *Biotechnol. Bioeng.* 104(4)651-662 (2009).
Qiu et al., "Metabolic engineering for the production of copolyesters consisting of 3-hydroxybutyrate and 3-hydroxyhexanoate by *Aeromonas hydrophilia*," *Macromol. Biosci.* 4(3):255-261 (2004).
Radhakrishnan et al., "Applications of metabolic modeling to drive bioprocess development for the production of value-aded chemicals," *Biotechnol. Bioprocess. Eng.* 10:408-417 (2005).
Ragsdale, "Enzymology of the wood-Ljungdahl pathway of acetogenesis," *Ann. NY Acad Sci.* 1125:129-136 (2008).
Ragsdale, "Life with carbon monoxide," *Crit Rev. Biochem. Mol. Biol.* 39:165-195 (2004).
Ragsdale, "Pyruvate ferredoxin oxidoreductase and its radical intermediate," *Chem. Rev.* 103:2333-2346 (2003).
Rajpal et al., "A general method for greatly improving the affinity of antibodies by using combinatorial libraries," *Proc. Natl. Acad. Sci. U.S.A.* 102(24):8466-8471 (2005).
Ramon-Maiques et al., "Structure of Acetylglutamate Kinase, a Key Enzyme for Arginine Biosynthesis and a Prototype for the Amino Acid Kinase Enzyme Family, during Catalysis," *Structure* 10:329-342 (2002).
Ramos et al., "Mutations affecting the enzymes involved in the utilization of 4-aminobutyric acid as nitrogen source by the yeast *Saccharomyces cerevisiae*," *Eur. J. Biochem.* 149:401-404 (1985).
Rangarajan et al., "Structure of [NiFe] hydrogenase maturation protein HypE from *Escherichia coli* and its interaction with HypF," *J. Bacteriol.* 190:1447-1458 (2008).
Rathinasabapathi, "Propionate, a source of β-alanine, is an inhibitor of β-alanine methylation in *Limonium latifolium*, Plumbaginaceae," *J. Plant Physiol.* 159:671-674 (2002).
Raybuck et. al., "Kinetic characterization of the carbon monoxide-acetyl-CoA (carbonyl group) exchange activity of the acetyl-CoA synthesizing CO dehydrogenase from *Clostridium thermoaceticum*," *Biochemistry* 27:7698-7702 (1988).
Recasens et al., "Cysteine Sulfinate Aminotransferase and Aspartate Aminotransferase Isoenzymes of Rat Brain. Purification, Characterization, and Further Evidence for Identity," *Biochemistry* 19:4583-4589 (1980).
Reda et al., "Reversible interconversion of carbon dioxide and formate by an electroactive enzyme," *Proc. Natl. Acad. Sci. U.S.A.* 105:10654-10658 (2008).
Redenbach et al., "A set of ordered cosmids and a detailed genetic and physical map for the 8 Mb *Streptomyces coelicolor* A3(2) chromosome," *Mol. Microbiol.* 21:77-96 (1996).
Reed et al., "An expanded genome-scale model of *Escherichia coli* K-12 (iJR904 GSM/GPR)," *Genome Biol.* 4(9):R54 (2003).
Reetz and Carballeria, "Iterative aturation mutagenesis (ISM) for rapid directed evolution of functional enzymes," *Nat. Protoc.* 2(4):891-903 (2007).
Reetz et al., "Creation of Enantioselective biocatalysts for Organic Chemistry by In Vitro Evolution," *Agnew. Chem. Int. Ed. Engl.* 36:2830-2832 (1997).
Reetz et al., "Directed Evolution of an Enantioselective Enzyme through Combinatorial Multiple-Cassette Mutagenesis," *Agnew. Chem. Int. Ed. Engl.* 40:3589-3591 (2001).
Reetz et al., "Expanding the Range of Substrate Acceptance of Enzymes: Combinatorial Active-site saturation test," *Agnew. Chem. Int. Ed. Engl.* 44:4192-4196 (2005).
Reetz et al., "Iterative Saturation Mutagenesis on the Basis of B Factors as a Strategy for Increasing Protein Thermostability,"*Agnew. Chem. Int. Ed. Engl.* 45:7745-7751 (2006).
Regev-Rudzki et al., "Yeast Aconitase in Two Locations and Two Metabolic Pathways: Seeing Small Amounts Is Believing," *Mol. Biol. Cell* 16:4163-4171 (2005).
Reidhaar-Olson and Sauer, "Combinatorial cassette mutagenesis as a probe of the informational content of protein sequences," *Science* 241(4861):53-57 (1988).

Reidhaar-Olson et al., "Random mutagenesis of protein sequences using oligonucleotide cassettes," *Methods Enzymol.* 208:564-586 (1991).
Reiser and Somerville, "Isolation of mutants of Acinetobacter calcoaceticus deficient in wax ester synthesis and complementation of one mutation with a gene encoding a fatty acyl coenzyme A reductase," *J. Bacteriol.* 179(9):2969-2975 (1997).
Reitzer, "Ammonia Assimillation and the Biosynthesis of Glutamine, Glutamate, Aspartate, Asparagine, l-Alanine, and d-Alanine," In Neidhardt (Ed.), *Escherichia coli and Salmonella: Cellular and Molecular Biology*, ASM Press: Washington, DC, p. 391-407 (1996).
Repetto and Tzagoloff, "Structure and Regulation of KGD1, the Structural Gene for Yeast α-Ketoglutarate Dehydrogenase," *Mol. Cell.* 9:2695-2705 (1989).
Resnekov et al., "Organization and regulation of the *Bacillus subtilis* odhAB operon, which encodes two of the subenzymes of the 2-oxoglutarate dehydrogenase complex," *Mol. Gen. Genet.* 234(2):285-296 (1992).
Ribeiro et al., "Microbial reduction of α-acetyl-γ-butyrolactone," *Tetrahedron: Asymmetry*, 17(6):984-988 (2006).
Rigden et al., "A cofactor-dependent phosphoglycerate mutase homolog from *Bacillus stearothermophilus* is actually a broad specificity phosphatase," *Protein Sci.* 10:1835-1846 (2001).
Ringquist et al., "Translation initiation in *Escherichia coli*: sequences within the ribosome-binding site," *Mol. Microbiol.* 6:1219-1229 (1992).
Riondet et al., "Measurement of the intracellular pH in *Escherichia coli* with the internally conjugated fluorescent probe 5- (and 6) carboxyfluorescein succinimidyl ester," *Biotechnol. Tech.* 11:735-738 (1997).
Riviere et al., "Acetyl:Succinate CoA-transferase in Procyclic *Trypanosoma brucei*," *J. Biol Chem.* 279(44):45337-45346 (2004).
Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. U.S.A.* 86:32-36 (1989).
Robinson et al., "Studies on Rat Brain Acyl-Coenzyme a Hydrolase (Short Chain)," *Biochem. Biophys. Res. Commun.* 71:959-965 (1976).
Roca et al., "Metabolic engineering of ammonium assimilation in xylose-fermenting *Saccharmyces cerevisiae* improves ethanol production," *Appl. Environ. Microbiol.* 69(8):4732-4736 (2003).
Rodriguez et al., "Characterization of the p-coumaric acid decarboxylase from *Lactobacillus plantarum* CECT 748(T)," *J. Agric. Food Chem.* 56(9):3068-3072 (2008).
Rohdich et al., "Enoate reductases of *Clostridia*. Cloning, sequencing, and expression," *J. Biol. Chem.* 276(8):5779-5787 (2001).
Romero et al., "Partial purification, characterization and nitrogen regulation of the lysine epsilon-aminotransferase of *Streptomyces clavuligerus*," *J. Ind. Microbiol. Biotechnol.* 18(4):241-246 (1997).
Rose and Weaver, "The role of the allosteric B site in the fumarase reaction," *Proc. Natl. Acad. Sci. U.S.A.* 101:3393-3397 (2004).
Rose et al., "Enzymatic phosphorylation of acetate," *J. Biol. Chem.* 211(2):737-756 (1954).
Rother and Metcalf, "Anaerobic growth of *Methanosarcina acetivorans* C2A on carbon monoxide: an unusual way of life for a methanogenic archaeon," *Proc. Natl. Acad. Sci. U.S.A.* 101:16929-16934 (2004).
Rother et al., "Genetic and proteomic analyses of CO utilization by *Methanosarcina acetivorans*," *Arch. Microbiol.* 188:463-472 (2007).
Roy and Dawes, "Cloning and Characterization of the Gene Encoding Lipamide Dehydrogenase in *Saccharomyces cerevisiae*," *J. Gen. Microbiol.* 133:925-933 (1987).
Ruldeekulthamrong et al., "Molecular characterization of lysine 6-dehydrogenase from *Achromobacter denitrificans*," *BMB Rep.* 41:790-795 (2008).
Sabo et al., "Purification and Physical Properties of Inducible *Escherichia coli* Lysine Decarboxylase," *Biochemistry* 13(4):662-670 (1974).
Saito and Doi, "Microbial synthesis and properties of poly(3-hydroxybutyrate-co-4-hydroxybutyrate) in *Comamonas acidovorans*," *Int. J. Biol. Macromol.* 16:99-104 (1994).

(56) References Cited

OTHER PUBLICATIONS

Saito et al., "Microbial Synthesis and properties of Poly(3-hydroxybutyrate-co-4-hydroxybutyrate)," *Polym. Int.* 39:169-174 (1996).
Sakai et al., "Acetate and ethanol production from H2 and CO2 by *Moorella* sp. using a repeated batch culture," *J. Biosci. Bioeng.* 99:252-258 (2005).
Sakakibara et al., "Isolation and characterization of a cDNA that encodes maize glutamate dehydrogenase," *Plant Cell Physiol.* 36:789-797 (1995).
Salmon et al., "Global gene expression profiling in *Escherichia coli* K12: effects of oxygen availability and ArcA," *J. Biol. Chem.* 280(15):15084-15096 (2005).
Samsonova et al., "Molecular cloning and characterization of *Escherichia coli* K12 ygjG gene," *BMC Microbiol.* 3:2 (2003).
Sanchez et al., "Properties and functions of two succinic-semialdehyde dehydrogenases from *Pseudomonas putida*," *Biochim. Biophys. Acta.* 953(3):249-257 (1988).
Sanchez et al., "Purification and properties of two succinic semialdehyde dehydrogenases from *Klebsiella pneumoniae*," *Biochim. Biophys. Acta.* 990(3):225-231 (1989).
Sariaslani, "Development of a Combined Biological and Chemical Process for Production of Industrial Aromatics from Renewable Resources," *Annu. Rev. Microbiol.* 61:51-69 (2007).
Sass et al., "Folding of fumarase during mitochondrial import determines its dual targeting in yeast," *J. Biol. Chem.* 278(46):45109-45116 (2003).
Sato et al., "Poly[(R)-3-Hydroxybutyrate] Formation in *Escherichia coli* from Glucose through an Enoyl-CoA Hydratase-Mediated Pathway," *J. Biosci. Bioeng.* 103(1):38-44 (2007).
Sauer et al., "Methanol:coenzyme M methyltransferase from *Methanosarcina barkeri*. Purification, properties and encoding genes of the corrinoid protein MT1," *Eur. J. Biochem.* 243:670-677 (1997).
Sawers and Boxer, "Purification and properties of membrane-bound hydrogenase isoenzyme 1 from anaerobically grown *Escherichia coli* K12," *Eur. J. Biochem.* 156:265-275 (1986).
Sawers et al., "Characterization and physiological roles of membrane-bound hydrogenase isoenzymes from *Salmonella typhimurium*," *J. Bacteriol.* 168:398-404 (1986).
Sawers et al., "Differential expression of hydrogenase isoenzymes in *Escherichia coli* K-12: evidence for a third isoenzyme," *J. Bacteriol.* 164:1324-1331 (1985).
Sawers, "The hydrogenases and formate dehydrogenases of *Escherichia coli*," *Antonie Van Leeuwenhoek* 66:57-88 (1994).
Scherf and Buckel, "Purification and properties of 4-hydroxybutyrate coenzyme A transferase from *Clostridium aminobutyricum*," *Appl. Environ. Microbiol.* 57(9):2699-2702 (1991).
Scherf and Buckel, "Purification and properties of an iron-sulfur and FAD-containing 4-hydroxybutyryl-CoA dehydratase/vinylacetyl-CoA Δ3—Δ2-isomerase from *Clostridium aminobutyricum*," *Eur. J. Biochem.* 215:421-429 (1993).
Scherf et al., "Suffinate-ethanol fermentation in *Clostridium kluyveri*: purification and characterisation of 4-hydroxybutyryl-CoA dehydratase/vinylacetyl-CoA delta 3-delta 2-isomerase," *Arch. Microbiol.* 161:239-245 (1994).
Schilling et al., "Toward Metabolic Phenomics: Analysis of Genomic Data Using Flux Balances," *Biotechnol. Prog.* 15:288-295 (1999).
Schilling et al., "Combining Pathway Analysis with Flux Balance Analysis for the Comprehensive Study of Metabolic Systems," *Biotechnol. Bioeng.* 71(4):286-306 (2000-2001).
Schilling et al., "Theory for the Systematic Definition of Metabolic Pathways and Their Use in Interpreting Metabolic Function from a Pathway-Oriented Perspective," *J. Theor. Biol.* 203(3):229-248 (2000).
Schneider et al., "The *Escherichia coli* gabDTPC operon: specific gamma-aminobutyrate catabolism and nonspecific induction," *J. Bacteriol.* 184:6976-6986 (2002).
Schulz et al., "Stereopsecific Production of the Herbicide Phosphinothricin (Glufosinate) by Transamination: Isolation and Characterization of a Phosphinothricin-Specific Transaminase from *Escherichia coli*," *Appl. Environ. Microbiol.* 56:1-6 (1990).
Scott and Jakoby, "Soluble γ-Aminobutyric-Glutamic Transaminase from *Pseudomonas fluorescens*," *J. Biol. Chem.* 234:932-936 (1959).
Seedorf et al., "The genome of *Clostridium kluyveri*, a strict anaerobe with unique metabolic features," *Proc. Natl. Acad. Sci. U.S.A.* 105(6):2128-2133 (2008).
Selifonova et al., "Rapid evolution of novel traits in microorganisms," *Appl. Environ. Microbiol.* 67(8):3645-3649 (2001).
Sen et al., "Developments in directed evolution for improving enzyme functions," *Appl. Biochem. Biotechnol.* 143(3):212-223 (2007).
Seravalli et al., "Evidence that NiNi acetyl-CoA synthase is active and that the CuNi enzyme is not," *Biochemistry* 43:3944-3955 (2004).
Seravalli et al., "Mechanism of transfer of the methyl group from (6S)-methyltetrahydrofolate to the corrinoid/iron-sulfur protein catalyzed by the methyltransferase from *Clostridium thermoaceticum*: a key step in the Wood-Ljungdahl pathway of acetyl-CoA synthesis," *Biochemistry* 38:5728-5735 (1999).
Shafiani et al., "Cloning and characterization of aspartate-β-semialdehyde dehydrogenase from *Mycobacterium tuberculosis* H37 Rv," *J. Appl. Microbiol.* 98:832-838 (2005).
Shalel-Levanon et al., "Effect of ArcA and FNR on the expression of genes related to the oxygen rregulation and the glycolysis pathway in *Escheriocha coli* under microaerobic growth conditions," *Biotechnol. Bioeng.* 92(2):147-159 (2005).
Shames et al., "Interaction of aspartate and aspartate-derived antimetabolites with the enzymes of the threonine biosynthetic pathway of *Escherichia ecoli*," *J. Biol. Chem.* 259(24):15331-15339 (1984).
Shao et al., "Random-priming in vitro recombination: an effective tool for directed evolution," *Nucleic Acids Res.* 26(2):681-683 (1998).
Sheppard et al., "Purification and properties of NADH-dependent 5, 10-methylenetetrahydrofolate reductase (MetF) from *Escherichia coli*," *J. Bacteriol.* 181:718-725 (1999).
Shi et al., "The structure of L-aspartate ammonia-lyase from *Escherichia coli*," *Biochem.* 36(30):9136-9144 (1997).
Shigeoka and Nakano, "Characterization and molecular properties of 2-oxoglutarate decarboxylase from *Euglena gracilis*," *Arch. Biochem. Biophys.* 288:22-28 (1991).
Shigeoka and Nakano, "The effect of thiamin on the activation of thiamin pyrophosphate-dependent 2-oxoglutarate decarboxylase in *Euglena gracilis*," *Biochem. J.* 292:463-467 (1993).
Shigeoka et al., "Effect of L-glutamate on 2-oxoglutarate decarboxylase in *Euglena gracilis*," *Biochem. J.* 282:319-323 (1992).
Shimomura et al., "3-Hydroxyisobutyryl-CoA Hydrolase," *Meth. Enzymol.* 324:229-240 (2000).
Shimomura et al., "Purification and Partial Characterization of 3-Hydroxyisobutyryl-coenzyme A Hydrolase of Rat Liver," *J. Biol. Chem.* 269:14248-14253 (1994).
Shimoyama et al., "MmcBC in *Pelotomaculum thermopropionicum* represents a novel group of prokaryotic fumarases," *FEMS Microbiol Lett.* 270(2):207-213 (2007).
Shingler et al., "Nucleotide Sequence and Functional Analysis of the Complete Phenol/3,4-Dimethylphenol Catabolic Pathway of *Pseudomonas* sp. Strain CF600," *J. Bacteriol.* 174(3):711-724 (1992).
Shiraki et al., "Fermentative production of (R)-(–)-(3) hydroxybutyrate using 3-hydroxybutyrate dehydrogenase null mutant of *Ralstonia eutropha* and recombinant *Escherichia coli*," *J. Biosci. Bioeng.* 102(6):529-534 (2006).
Shukla et al., "Production of D(–)-lactate from sucrose and molasses," *Biotechnol. Lett.* 26(9):689-693 (2004).
Sieber et al., "Libraries of hybrid proteins from distantly related sequences," *Nat. Biotechnol.* 19(5):456-460 (2001).
Siebers et al., "Reconstruction of the central carbohydrate metabolism of *Thermoproteus tenax* by use of genomic and biochemical data," *J. Bacteriol.* 186(7):2179-2194 (2004).

(56) References Cited

OTHER PUBLICATIONS

Siegert et al., "Exchanging the substrate specificities of pyruvate decarboxylase from *Zymomonas mobilis* and benzoylase from *Pseudomonas putida*," *Protein Eng. Des. Sel.* 18:345-357 (2005).
Siminov et al.,"Application of Gas Chromatography and Gas Chromatography-Mass Spectrometry to the Detection of γ-Hydroxybutyric Acid and Its Precursors in Various Materials," *J. Anal. Chem.* 59:965-971 (2004).
Simpma et al., "Microbial CO Conversions with Applications in Synthesis Gas Purification and Bio-Desulfurization," *Crit. Rev. Biotech.* 26:41-65 (2006).
Sinclair et al, "Purification and characterization of the branched chain α-ketoacid dehydrogenase complex from *Saccharomyces cerevisiae*," *Biochem. Mol. Biol. Int.* 31(5):911-922 (1993).
Sivaraman et al., "Codon choice in genes depends on flanking sequence information—implications for theoretical reverse translation," *Nucleic Acids Res.* 36(3):e16 (2008).
Sjostrom et al., "Purfication and characterisation of a plasminogen-binding protein from *Haemophilus influenzae*. Sequence determination reveals identity with aspartase," *Biochim. Biophys. Acta.* 1324:182-190 (1997).
Skarstedt and Silverstein, "*Escherichia coli* Acetate Kinase Mechanism Studied by Net Initial Rate, Equilibriu, and Independent Isotopic Exchange Kinetics," *J. Biol. Chem.* 251:6775-6783 (1976).
Skinner and Cooper, "An *Escherichia coli* mutant defective in the NAD-dependent succinate semialdehyde dehydrogenase," *Arch. Microbiol.* 132(3):270-275 (1982).
Smit et al., "Identification, Cloning, and Characterization of a *Lactococcus lactis* Branched-Chain α-Keto Acid Decarboxylase Involved in Flavor Formation," *Appl. Environ. Microbiol.* 71:303-311 (2005).
Smith et al., "Fumarate metabolism and the microaerophily of *Campylobacter* species," *Int. J. Biochem. Cell Biol.* 31:961-975 (1999).
Smith et al., "Purification and characteristics of a gamma-glutamyl kinase involved in *Escherichia coli* proline biosynthesis," *J.Bacteriol.* 157:545-551 (1984).
Smith et al., "Complete genome sequence of *Methanobacterium thermoautotrophicum* deltaH: functional analysis and comparative genomics," *J. Bacteriol.* 179:7135-7155 (1997).
Snedecor et al., "Selection, expression, and nucleotide sequencing of the glutamate dehydrogenase gene of *Peptostreptococcus asaccharolyticus*," *J. Bacteriol.* 173:6162-6167 (1991).
Soda and Misono, "L-Lysine:alpha-ketoglutarate aminotransferase. II. Purification, crystallization, and properties," *Biochemistry* 7(11):4110-4119 (1968).
Sohling and Gottschalk, "Molecular analysis of the anaerobic succinate degradation pathway in *Clostridium kluyveri.*," *J. Bacteriol.* 178(3):871-880 (1996).
Sohling and Gottschalk, "Purification and characterization of a coenzyme-A-dependent succinate-semialdehyde dehydrogenase from *Clostridium kluyveri*," *Eur. J. Biochem.* 212:121-127 (1993).
Sokatch et al., "Purification of a Branched-Chain Keto Acid Dehydrogenase from *Pseudomonas putida*," *J. Bacteriol.* 647-652 (1981).
Song et al, "Structure, Function, and Mechanism of the Phenylacetate Pathway Hot Dog-fold Thioesterase PaaI," *J. Biol. Chem.* 281(16):11028-11038 (2006).
Song et al., "Construction of recombinant *Escherichia coli* strains producing poly (4-hydroxybutyric acid) homopolyester from glucose," *Wei Sheng Wu Xue Bao*, 45(3):382-386 (2005). (In Chinese, includes English abstract).
Spencer and Guest, "Transcription analysis of the sucAB, aceEF and lpd genes of *Escherichia coli*," *Mol. Gen. Genetics* 200:145-154 (1985).
Spencer et al., "Nucleotide sequence of the sucB gene encoding the dihydrolipoamide succinyltransferase of *Escherichia coli* K12 and homology with the corresponding acetyltransferase," *Eur. J. Biochem.* 141(2):361-374 (1984).

St Maurice et al., "Flavodoxin:quinone reductase (FqrB): a redox partner of pyruvate:ferredoxin oxidoreductase that reversibly couples pyruvate oxidation to NADPH production in *Helicobacter pylori* and *Campylobacter jejuni*," *J. Bacteriol.* 189(13):4764-4773 (2007).
Stadtman, "The enzymatic synthesis of β-alanyl coenzyme A," *J. Am. Chem. Soc.* 77:5765-5766 (1955).
Stanley et al., "Expression and Sterochemical and Isotope Effect Studies of Active 4-Oxalocrotonate Decarboxylase," *Biochem.* 39:(4):718-726 (2000).
Starai et al., "Acetate excretion during rowth of *Salmonella enterica* on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).
Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).
Steffan and McAlister-Henn, "Isolation and Characterization of the Yeast Gene Encoding the MDH3 Isozyme of Malate Dehydrogenase," *J. Biol. Chem.* 267(34):24708-24715 (1992).
Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Steinbuchel and Schlegel, "A multifunctional fermentative alcohol dehydrogenase from the strict aerobe *Alcaligenes eutrophus*: purification and properties," *Eur. J. Biochem.* 141:555-564 (1984).
Steinbuchel and Schlegel, "Physiology and molecular genetics of poly(beta-hydroxy-alkanoic acid) synthesis in *Alcaligenes eutrophus*," *Mol. Microbiol.* 5(3):535-542 (1991).
Steinbuchel and Valentin, "Diversity of bacterial polyhydroxyalkanoic acids," *FEMS Microbiol. Lett.* 128:219-228 (1995).
Steinbuchel et al., "A Pseudomonas strain accumulating polyesters of 3-hydroxybutyric acid and medium-chain-length 3-hydroxyalkanoic acids," *Appl. Microbiol. Biotechnol.* 37:691-697 (1992).
Stemmer, "DNA Shuffling by random fragmentation and reassembly: in vitro recombination for molecular evolution," *Proc. Natl. Acad. Sci. U.S.A.* 91(22):10747-10751 (1994).
Stemmer, "Rapid evolution of a protein in vitro by DNA shuffling," *Nature* 370:389-391 (1994).
Stokell et al., "Probing the roles of key residues in the unique regulatory NADH binding site of type II citrate synthase of *Escherichia coli*," *J. Biol. Chem.* 278(37):35435-35443 (2003).
Stols et al., "New vectors for co-expression of proteins: Structure of *Bacillus subtilis* ScoAB obtained by high-throughput protocols," *Protein Expr. Purif.* 53:396-403 (2007).
Stoyan et al., "Cloning, sequencing and overexpression of the leucine dehydrogenase gene from *Bacillus cereus*," *J. Biotechnol.* 54:77-80 (1997).
Strauss and Fuchs, "Enzymes of a novel autotrophic CO2 fixation pathway in the phototrophic bacterium *Chloroflexus aurantiacus*, the 3-hydroxypropionate cycle," *Eur. J. Biochem.* 215:633-643 (1993).
Suda et al., "Purification and properties of alpha-keoadipate reductase, a newly discovered enzyme from human placenta," *Arch. Biochem. Biophys.* 176(2):610-620 (1976).
Suda et al., "Subcellular Localization and tissue Distribution of α-Ketodaipate Reduction and Oxidation in the Rat," *Biochem. Biophys. Res. Commun.* 77:586-597 (1977).
Suematsu et al., "Molecular cloning and functional expression of rat liver cytosolic acetyl-CoA hydrolase," *Eur. J. Biochem.* 268(9):2700-2709 (2001).
Sulzenbacher et al., "Crystal structure of *E. coli* alcohol dehydrogenase YqhD: evidence of a covalently modified NADP coenzyme," *J. Mol. Biol.* 342(2):489-502 (2004).
Suthers et al., "Metabolic flux elucidation for large-scale models using 13C labeled isotopes," *Metab. Eng.* 9(5-6):387-405 (2007).
Suzuki et al., "GriC and GriD Constitute a carboxylic acid reductase involved in grixazone biosynthesis in *Streptomyces griseus*," *J. Antibiot.* 60(6):380-387 (2007).

(56) References Cited

OTHER PUBLICATIONS

Suzuki, "Phosphotransacetylase of *Escherichia coli* B, activation by pyruvate and inhibition by NADH and certain nucleotides," *Biochim. Biophys. Acta* 191(3):559-569 (1969).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S. A.* 101:446-451 (2004).

Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183:5134-5144 (2001).

Syntichaki et al., "The amino-acid sequence similarity of plant glutamate dehydrogenase to the extremophilic archaeal enzyme conforms to its stress-related function," *Gene.* 168:87-92 (1996).

Takagi and Kisumi, "Isolation of a Versatile *Serratia marcescens* Mutant as a Host and Molecular Cloning of the Aspartase Gene," *J. Bacteriol.* 161(1):1-6 (1985).

Takagi et al., "Purfication, Crystallization, and Molecular Properties of Aspartase from *Pseudomonas fluorescens*," *J. Biochem.* 96:545-552 (1984).

Takahashi et al., "Metabolic Pathways for Cytoxic End Product Formation from Glutamate- and Aspartate-Containing Peptides by *Porphyromonas gingivalis*," *J. Bacteriol.* 182(17):4704-4710 (2000).

Takahashi-Abbe et al., "Biochemical and functional properties of a pyruvate formate-lyase (PFL)-activating system in *Streptococcus mutans*," *Oral Microbiol. Immunol.* 18(5):293-297 (2003).

Takanashi et al., "Characterization of a novel 3-hydroxybutyrate dehydrogenase from *Ralstonia pickettii* T1," *Antonie van Leeuwnhoek* 5(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182(23):6732-6741 (2000).

Takatsuka et al., "Identification of the amino acid residues conferring substrate specificity upon selenomonas ruminantium lysine decarboxylase," *Biosci. Biotechnol. Biochem.* 63(10):1843-1846 (1999).

Takigawa et al., "Probabilistic path ranking based on adjacent pairwise coexpression for metabolic transcripts analysis," *Bioinformatics* 24(2):250-257 (2008).

Tallant and Krzycki, "Coenzyme M methylase activity of the 480-kilodalton corrinoid protein from *Methanosarcina barkeri*," *J. Bacteriol.* 175:1295-1301 (1996).

Tallant and Krzycki, "Methylthiol:coenzyme M methyltransferase from *Methanosarcina barkeri*, an enzyme of methanogenesis from dimethylsulfide and methylmercaptopropionate," *J. Bacteriol.* 179:6902-6911 (1997).

Tallant et al., "The MtsA subunit of the methylthiol:coenzyme M methyltransferase of *Methanosarcina barkeri* catalyses both half-reactions of corrinoid-dependent dimethylsulfide: coenzyme M methyl transfer," *J. Biol. Chem.* 276:4485-4493 (2001).

Tamaki et al., "Purification, Properties, and Sequencing of Aminisobutyrate Aminotransferases from Rat Liver," *Meth. Enzymol.* 324:376-389 (2000).

Tanaka et al., "Cloning and characterization of a human orthologue of testis-specific succinyl CoA:3-oxo acid CoA transferase (Scot-t) cDNA," *Mol. Hum. Reprod.* 8:16-23 (2001).

Tanaka et al., "Lysine decarboxylase of *Vibrio parahaemolyticus*: kinetics of transcription and role in acid resistance," *J. Appl. Microbiol.* 104(5):1283-1293 (2007).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Tani et al., "Thermostable NADP(+)-dependent medium-chain alcohol dehydrogenase from *Acinetobacter* sp strain M-1: Purification and characterization and gene expression in *Escherichia coli*," *Appl. Environ. Microbiol.* 66:5231-5235 (2000).

Teller et al., "The glutamate dehydrogenase gene of *Clostridium symbiosum*, Cloning by polymerase chain reaction sequence analysis and over-expression in *Escherichia coli*," *Eur. J. Biochem.* 206:151-159 (1992).

ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," *Appl. Environ. Microbiol.* 64(4):1303-1307 (1998).

Thakur et al., "Changes in the Electroencephalographic and .gamma.-Aminobutyric Acid Transaminsase and Succinic Semialdehyde Dehydrogenase in the Allergen Induced Rat Brain," *Biochem. Int.* 16:235-243 (1998).

Thauer, "Microbiology. A fifth pathway of carbon fixation," *Science* 318:1732-1733 (2007).

Tian et al., "Variant tricarboxylic acid cycle in *Mycobacterium tuberculosis*: identification of alpha-ketoglutarate decarboxylase," *Proc. Natl. Acad. Sci. U.S.A.* 102(30):10670-10675 (2005).

Tobin et al., "Localization of the lysine epsilon-aminotransferase (lat) and delta-(L-alpha-aminoadipyl)-L-cysteinyl-D-Valine synthetase (pcbAB) genes from *Streptomyces clavuligerus* and production of lysine epsilon-aminotransferase activity in *Escherichia coli*," *J. Bacteriol.* 173(19):6223-6229 (1991).

Tomb et al., "The complete genome sequence of the gastric pathogen *Helicobacter pylori*," *Nature* 388:539 (1997).

Toth et al., "The aid gene, encoding a coenzyme A-acylating aldehyde dehydrogenase, distinguishes *Clostridium beijerinckii* and two other solvent-producing clostridia from *Clostridium acetobutylicum*," *Appl. Environ. Microbiol.* 65(11):4973-4980 (1999).

Tretter and Adam-Vizi, "Alpha-ketoglutarate dehydrogenase: a target and generator of oxidative stress," *Philos. Trans. R. Soc. Lond B. Biol. Sci.* 360:2335-2345 (2005).

Tseng et al., "Metabolic engineering of *Escherichia coli* for enhanced production of (R)- and (S)-3-hydroxybutyrate," *Appl. Environ. Microbiol.* 75(10):3137-3145 (2009).

Tseng et al., "Oxygen- and growth rate-dependent regulation of *Escherichia coli* fumarase (FumA, FumB, and BumC) activity," *J. Bacteriol.* 183(2):461-467 (2001).

Tucci and Martin, "A novel prokaryotic trans-2-enoyl-CoA reductase from the spirochete *Treponema denticola*," *FEBS Lett.* 581:1561-1566 (2007).

Twarog and Wolfe, "Role of Buyryl Phosphate in the Energy Metabolism of *Clostridium etanomorphum*," *J. Bacteriol.* 86:112-117 (1963).

Tzimagiorgis et al., "Molecular cloning, structure and expression analysis of a full-length mouse brain glutamate dehydrogenase cDNA," *Biochem. Biophys. Acta.* 1089:250-253 (1991).

Tzimagiorgis et al., "Structure and expression analysis of a member of the human glutamate dehydrogenase (GLUD) gene gamily mapped to chromosome 10p11.2," *Hum. Genet.* 91:433-438 (1993).

Uchiyama et al., "Identification of the 4-Hydroxycinnamate Decarboxylase (PAD) Gene of *Klebsiella oxytoca*," *Biosci. Biotechnol. Biochem.* 72:116-123 (2008).

Umeda et al., "Cloning and sequence analysis of the poly(3-hydroxyalkanoic acid)-synthesis genes of *Pseudomonas acidophila*," *Appl. Biochem. Biotechnol*, 70-72:341-352 (1998).

Uttaro and Opperdoes, "Purification and characterisation of a novel iso-propanol dehydrogenase from *Phytomonas* sp," *Mol. Biochem. Parasitol.* 85:213-219 (1997).

Valdes-Hevia and Gancedo, "Isolation and characterization of the gene encoding phosphoenolpyruvate carboxykinase from *Saccharomyces cerevisiae*," *FEBS Lett.* 258(2):313-316 (1989).

Valentin et al., "Indentication of 4-hydroxyhexanoic acid as a new constituent of biosynthetic polyhydroxyalkanoic acids from bacteria," *Appl. Microbiol. Biotechnol.* 40:710-716 (1994).

Valentin et al., "Identification of 4-hydroxyvaleric acid as a constituent of biosynthetic polyhydroxyalkanoic acids from bacteria," *Appl. Microbiol. Biotechnol.* 36:507-514 (1992).

Valentin et al., "Identification of 5-hydroxyhexanoic acid, 4-hydroxyheptanoic acid and 4-hydroxyoctanoic acid as new constituents of bacterial polyhydroxyalkanoic acids," *Appl. Microbiol. Biotechnol.* 46:261-267 (1996).

(56) References Cited

OTHER PUBLICATIONS

Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem*. 227:43-60 (1995).
Valentin et al., "Poly(3-hydroxybutyrate-co-4-hydroxybutyrate) formation from gamma-aminobutyrate and glutamate," *Biotechnol Bioeng*. 67(3):291-299 (2000).
Valentin et al., "Production of poly(3-hydroxybutyrate-co-4-hydroxybutyrate) in recombinant *Escherichia coli* grown on glucose," *J. Biotechnol*. 58:33-38 (1997).
Valentine and Wolfe, "Purification and role of phosphotransbutyrylase," *J. Biol. Chem*. 235:1948-1952 (1960).
Valle et al., "Complete nucleotide sequence of the glutamate dehydrogenase gene from *Escherichia coli* K-12," *Gene* 27:193-199 (1984).
Valle et al., "Nucleotide sequence of the promotor and amino-terminal coding region of the glutamate dehydrogenase structural gene of *Escherichia coli*," *Gene* 23:199-209 (1983).
Vamecq et al., "The microsomal dicarboxylyl-CoA synthetase," *Biochem. J*. 230:683-693 (1985).
Van der Rest et al., "Functions of the membrane-associated and cytoplasmic malate dehydrogenases in the citric acid cycle of *Escherichia coli*," *J. Bacteriol*183(24):6892-6899 (2000).
van der Voorhorst et al., "Genetic and biochemcial characterization of a short-chain alcohol dehydrogenase from the hyperthermophilic archaeon *Pyrococcus furiosus*," *Eur. J. Biochem*. 268:3062-3068 (2001).
Van Grinsven et al., "Acetate:Succinate CoA-transferase in the Hydrogenosomes of *Trichomonas vaginalis*," *J. Biol. Chem*. 283:1411-1418 (2008).
Vanderwinkel et al., "Growth of *Escherichia coli* on Fatty Acids: Requirement for Coenzyme a Transferase Activity," *Biochem. Biophys. Res. Commun*. 33:902-908 (1968).
Vanrolleghem et al., "Validation of a Metabolic Network for *Saccharomyces cerevisiae* Using Mixed Substrate Studies," *Biotechnol. Prog*. 12(4):434-448 (1996).
Varma and Palsson, "Metabolic Flux balancing: Basic concepts, Scientific and Practical Use," *Biotechnol*. 12:994-998 (1994).
Varma and Palsson, "Stoichiometric flux balance models quantitatively predict growth and metabolic by-product secretion in wild-type *Escherichia coli* W3110," *Appl. Environ. Microbiol*. 60:3724-3731 (1994).
Vazquez et al., "Phosphotransbutyrylase Expression in *Bacillus megaterium*," *Curr. Microbiol*. 42:345-349 (2001).
Venkitasubramanian et al. Biocatalysis in the Pharmaceutical and Biotechnology Industries, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol Chem*. 282:478-485 (2007).
Vernal et al., "Cloning and heterologous expression of a broad specificity aminotransferase of *Leishmania mexicana* promastigotes1," *FEMS Microbiol. Lett*. 229(2):217-222 (2003).
Vernal et al., "Isolation and partial characterization of a broad specificity aminotransferase from *Leishmania mexicana* promastigotes," *Mol. Biochem. Parasitol*. 96(1-2):83-92 (1998).
Vey et al., "Structural basis for glycyl radical formation by pyruvate formate-lyase activating enzyme," *Proc. Natl. Acad. Sci. U.S.A*. 105(42):16137-16141 (2008).
Viola, "L-aspartase: new tricks from an old enzyme," *Adv. Enzymol. Relat. Areas. Mol. Biol*. 74:295-341 (2000).
Voets et al., "Reduced intracellular ionic strength as the initial trigger for activation of endothelial volume-regulated anion channels," *Proc. Natl. Acad. Sci. USA* 96:5298-5303 (1999).
Volkov et al., "Random chimeragenesis by heteroduplex recombination," *Methods Enzymol*. 3289456-463 (2000).
Volkov et al., "Recombination and chimeragenesis by in vitro heteroduplex formation and in vivo repair," *Nucleic Acids Res*. 27(18):e18 (1999).

Wakil et al., "Studies on the Fatty Acid Oxidizing System of Animal Tissues," *J. Biol. Chem*. 207:631-638 (1954).
Walker et al., "Yeast pyruvate carboxylase: identification of two genes encoding isoenzymes," *Biochem. Biophys. Res. Commun*. 176(3):1210-1217 (2007).
Walter et al., "Sequence and arrangement of two genes of the butyrate-synthesis pathway of *Clostridium acetobutylicum* ATCC 824," *Gene* 134:107-111 (1993).
Walter et al., "Molecular characterization of two *Clostridium acetobutylicum* ATCC 824 butanol dehydrogenase isozyme genes," *J. Bacteriol*. 174(22):7149-7158 (1992).
Wang et al., "Molecular cloning and functional identification of a novel phenylacetyl-CoA ligase gene from *Penicillium chrysogenum*," *Biochem. Biophys. Res. commun*. 360(2):453-458 (2007).
Wang et al., "The primary structure of branched-chain α-oxo acid dehydrogenase from *Bacillus subtilis* and its similarity to other α-oxo acid dehydrogenases," *Eur. J. Biochem*. 213:1091-1099 (1993).
Wang et al., "Isolation of poly-3-hydroxybutyrate metabolism genes from complex microbial communities by phenotypic complementation of bacterial mutants," *Appl. Environ. Microbiol*. 72(1):384-391 (2006).
Wang et al., "Screening microorganisms for utilization of furfural and possible intermediates in its degradative pathway," Biotechnol. Lett. 16(9):977-982 (1994).
Ward et al., "Molecular analysis of the role of two aromatic aminotransferases and abroad-specificity aspartate aminotransferase in the aromatic amino acid metabolism of *Pyrococcus furiosus*," *Archaea* 1:133-141 (2002).
Weaver, "Structure of free fumarase C from *Escherichia coli*," *Acta. Crystallog. D. Biol. Crystallogr*. 61:1395-1401 (2005).
Weidner and Sawers, "Molecular Characterization of the Genes Encoding Pyruvate Formate-Lyase and Its Activating Enzyme of *Clostridium pasteruianum*," *J. Bacteriol*. 178(8):2440-2444 (1996).
Welch et al., "Purification and characterization of the NADH-dependent butanol dehydrogenase from *Clostridium acetobutylicum* (ATCC 824)," *Arch. Biochem. Biophys*. 273(2):309-318 (1989).
Werpy et al., "Top Value Added Chemicals from Biomass. vol. I—Results of Screening for Potential Candidates from Sugars and Synthesis Gas," DOE Report (2004).
Westin et al., "The Identification of Succinyl-CoA Thioesterase Suggests a Novel Pathway for Succinate Production in Peroxisomes," *J. Biol. Chem*. 280(46):38125-38132 (2005).
Wexler et al., "A wide host-range metagenomic library from a waste water treatment plant yields a novel alcohol/aldehyde dehdrogenase," *Environ. Microbiol*. 7:1917-1926 (2005).
Whalen and Berg, "Analysis of an *avtA*::Mu d1(Ap lac) Mutant: Metabolic role of Transaminase C," *J. Bacterial*. 150(2):739-746 (1982).
Whalen and Berg, "Gratuitous Repression of *avtA* in *Escherichia coli* and *Salmonella typhimurium*," *J. Bacteriol*. 158(2):571-574 (1984).
Whitehead and Rabinowitz, "Cloning and expression in *Escherichia coli* of the gene for 10-formyltetrahydrofolate synthetase from *Clostridium acidiurici* ("*Clostridium acidi-urici*")," *J. Bacterial*. 167:205-209 (1986).
Whitehead and Rabinowitz, "Nucleotide sequence of the *Clostridium acidiurici* ("*Clostridium acidi-urici*") gene for 10-formyltetrahydrofolate synthetase shows extensive amino acid homology with the trifunctional enzyme C1-tetrahydrofolate synthase from *Saccharomyces cerevisiae*," *J. Bacteriol*. 170:3255-3261 (1988).
Wiesenborn et al., "Coenzyme A Transferase from *Clostridium acetobutylicum* ATC 824 and Its Role in the Uptake of Acids," *Appl. Environ. Microbiol*. 55:323-329 (1989).
Wilkie and Warren, "Recombinant Expression, Purification, and Characterization of Three Isoenzymes of Aspartate Aminotrannsferase from *Arabidopsis thaliana*," *Protein Expr. Purif*. 12:381-389 (1998).
Wilks et al., "A specific, highly active malate dehydrogenase by redesign of a lactate dehydrogenase framework," *Science* 242(4885):1541-1544 (1988).
Wilks et al., "Design for a broad substrate specificity keto acid dehydrogenase," *Biochemistry* 29(37)8587-8591 (1990).

(56) References Cited

OTHER PUBLICATIONS

Wilks et al., "Design of a specific phenyllactate dehydrogenase by peptide loop exchange on the *Bacillus stearothermophilus* lactate dehydrogenase framework," *Biochemistry* 31(34):7802-7806 (1992).
Willadsen and Buckel, "Assay of 4-hydroxybutyryl-CoA dehydrasate from *Clostridium aminobutyricum*," *FEMS Microbiol. Lett.* 70:187-191 (1990).
Williams et al., "Biodegradable plastics from plants," *CHEMTECH* 26:38-44 (1996).
Willke and Vorlop, "Biotechnological production of itaconic acid," *Appl. Microbiol. Biotechnol.* 56:289-295 (2001).
Winzer et al., "Differential regulation of two thiolase genes from *Clostridium acetobutylicum* DSM 792," *J. Mol. Microbiol. Biotechnol.* 2:531-541 (2000).
Wolff and Kenealy, "Purification and characterization of the oxygen-sensitive 4-hydroxybutanoate dehydrogenase from *Clostridium kluyveri*," *Protein Expr. Purif.* 6:206-212 (1995).
Wolff et al., "Dehydrogenases involved in the conversion of succinate to 4-hydroxybutanoate by *Clostridium kluyven*," *Appl. Environ. Microbio.* 59:1876-1882 (1993).
Wong et al., "Sequence satruation mutagenesis with tunable mutation frequencies," *Anal. Biochem.* 341:187-189 (2005).
Wong et al., "Sequence saturation mutagenesis (SeSaM): a novel method for directed evolution," *Nucleic Acids Res.* 32(3):e26 (2004).
Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).
Woods, "Two biochemically distinct classes of fumarase in *Escherichia coli*," *Biochim. Biophys. Acta* 954(1):14-26 (1988).
Wu et al., "Life in hot carbon monoxide: the complete genome sequence of *Carboxydothermus hydrogenoformans* Z-2901," *PLoS Genetics* 1(5):0563-0574 (2005).
Wynn et al., "Chaperonins GroEL and GroES Promote Assembly of Heterotramers (α2β2) of Mammalian Mitochondrial Branched-chain α-Keto Acid Decarboxylase in *Escherichia coli*," *J. Biol. Chem.* 267(18):12400-12403 (1992).
Wynn et al., "Cloning and Expression in *Escherichia coli* of a Mature E1β Subunit of Bovine Mitochondrial Branched-chain α-Keto Acid Dehydrogenase Complex," *J. Biol Chem.* 267(3):1881-1887 (1992).
Yagi et al., "Aspartate: 2-Oxoglutarate Aminotransferase from Bakers' Yeast: Crystallization and Charactierization," *J. Biochem.* 92:35-43 (1982).
Yagi et al., "Crystallization and Properties of Aspartate Aminotransferase from *Escherichi coli* B," *FEBS Lett.* 100(1)81-84 (1979).
Yagi et al., "Glutamate-Aspartate Transaminase from Microorganisms," *Meth. Enzymol.* 113:83-89 (1985).
Yamamoto et al., "Carboxylation reaction catalyzed by 2-oxoglutarate:ferredoxin oxidoreductases from *Hydrogenobacter thermophilus*," *Extremophiles* 14:79-85 (2010).
Yamamoto et al., "Purification and properties of NADP-dependent formate dehydrogenase from *Clostridium thermoaceticum*, a tungsten-selenium-iron protein," *J. Biol. Chem.* 258:1826-1832 (1983).
Yang et al, "Nucleotide Sequence of the *fadA* Gene. Primary structure of 3-ketoacyl-coenzyme A thiolase from *Escherichia coli* and the structural organization of the *fadAB* operon," *J. Biol. Chem* 265(18):10424-10429 (1990) with correction in *J. Biol. Chem* 266(24):16255 (1991).
Yang et al., "Aspartate Dehydrogenase, a Novel Enszyme Idnetified from Structural and Functional Studies of TM16343," *J. Biol. Chem.* 278:8804-8808 (2003).
Yang et al., "Continuous cultivation of *Lactobacillus rhamnosus* with cell recycling using an acoustic cell settler," *Biotechnol. Bioprocess. Eng.* 7(6):357-361 (2002).
Yang et al., "Nucleotide Sequence of the fadA Gene," *J. Biol. Chem.* 265(18):10424-10429 (1990).

Yang et al., Nucleotide sequence of the promoter and fadB gene of the fadBA operon and primary structure of the multifunctional fatty acid oxidation protein from *Escherichia coli, Biochemistry* 30(27):6788-6795 (1991).
Yano et al., "Directed evolution of an aspartate aminotransferase with new substrate specificities," *Proc. Natl. Acad. Sci. U.S.A.* 95:5511-5515 (1998).
Yarlett et al., "*Trichomonas vaginalis*: characterization of ornithine decarboxylase," *Biochem. J.* 293:487-493 (1993).
Yee et al., "Isolation and characterization of a NADP-dependent glutamate dehydrogenase gene from the primitive eucaryote *Giardia lamblia*," *J. Biol. Chem.* 267:7539-7544 (1992).
Yoshida et al., "The structures of L-rhamnose isomerase from *Pseudomonas stutzeri* in complexs with L-rhamnose and D-allose provide insights into broad substrate specificity," *J. Mol. Biol.* 365(5):1505-1516 (2007).
Youngleson et al., "Homology between hydroxybutyryl and hydroxyacyl coenzyme A dehydrogenase enzymes from *Clostridium acetobutylicum* fermentation and vertebrate fatty acid beta-oxidation pathways," *J. Bacteriol.* 171(12):6800-6807 (1989).
Yu et al., "sucAB and sucCD are mutually essential genes in *Escherichia coli*," *FEMS Microbiol. Lett.* 254(2):245-250 (2006).
Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).
Yun et al., "Omega-Amino acid:pyruvate transaminase from *Alcaligenes denitrificans* Y2k-2: a new catalyst for kinetic resolution of beta-amino acids and amines," *Appl. Environ. Microbiol.* 70(4):2529-2534 (2004).
Zeiher and Randall, "Identification and Characterization of Mitochondrial Acetyl-Coenzyme A Hydrolase from *Pisum sativum* L. seedlings," *Plant Physiol.* 94:20-27 (1990).
Zhang et al., "2-Oxoacid: Ferredoxin Oxidoreductase from the Thermoacidophilic Archaeon, *Sulfolobus* sp. Strain $7^1$," *J. Biochem.* 120:587-599 (1996).
Zhang et al., "A new logic for DNA engineering using recombination in *Escherichia coli*," *Nat. Genet.* 20:123-128 (1998).
Zhang et al., "Directed evolution of a fucosidase from a galactosidase by DNA shuffling and screening," *Proc. Natl. Acad. Sci. U.S.A.* 94:4504-4509 (1997).
Zhang et al., "Isolation and Properties of a levo-lactonase from *Fusarium proliferatum* ECD2002: a robust biocatalyst for production of chiral lactones," *App. Microbiol. Biotechnol.* 75(5):1087-1094 (2007).
Zhang, et al., "Kinetic and mechanistic characterization of the polyhydroxybutyrate synthase from *Ralstonia eutropha*," *Biomacromolecules* 1(2):244-251 (2000).
Zhao et al., "Molecular evolution by staggered extension process (StEP) in vitro recombination," *Nat. Biotechnol.* 16(3):258-261 (1998).
Zhou et al., "Engineering a native homoethanol pathway in *Escherichia coli* B for ethanol production," *Biotechnol. Lett.* 30:335-342 (2008).
Zhou et al., Isolation, crystallization and preliminary X-ray analysis of a methanol-induced corrinoid protein from *Moorella thermoacetica. Acta Cryst.* F61:537-540 (2005).
Zhou et al., "The remarkable structural and functional organization of the eukaryotic pyruvate dehydrogenase complexes," *Proc. Natl. Acad. Sci. USA* 98:14802-14807 (2001).
Zhou et al., "Functional replacement of the *Escherichia coli* D-(−)-lactate dehydrogenase gene (ldhA) with the L-(+)-lactate dehydrogenase gene (ldhL) from *Pediococcus acidilactici*," *Appl. Environ. Micro.* 69:2237-2244 (2003).
Zhuang et al., "The YbgC protein encoded by the ybgC gene of the tol-pal gene cluster of *Haemophilus influenzae* catalyzes acyl-coenzyme A thioester hydrolysis," *FEBS Lett.* 516:161-163 (2002).
Four pages from URL: shigen.nig.ac.jp/ecoli/pec/genes.List. DetailAction.do (Printed Dec. 21, 2009).
One page from URL: expressys.de/. (Printed Dec. 21, 2009).
Two pages from URL: openwetware.org/wiki/Synthetic_Biology:BioBricks, Synthetic Biology:BioBricks, portal for information relating to the Registry of Standard Biological Parts (Printed Dec. 21, 2009).

(56) References Cited

OTHER PUBLICATIONS

Two pages from URL: www.genome.jp/dbget-bin/www_bget?cdf:CD2966 (Printed Dec. 21, 2009).

Two pages from URL: www.genome.jp/dbget-bin/www_bget?cpe:CPE2531 (Printed Dec. 21, 2009).

Two pages from URL: www.genome.jp/dbget-bin/www_bget?ctc:CTC01366 (Printed Dec. 21, 2009).

Two pages from URL: www.genome.jp/dbget-bin/www_bget?cth:Cthe_0423 (Printed Mar. 4, 2010).

Two pages from URL: scientificamerican.com/article.cfm?id=turning-bacteria-into-plastic-factories-replacing-fossil-fuels (Printed Feb. 17, 2011).

Gene Bridges, "Quick & Easy BAC Modification Kit by Red®/ET® Recombination," Technical Protocol, Cat. No. K001, Version 2.6 (2007).

Kakimoto et al., "Beta-aminoisobutyrate-alpha-ketoglutarate transaminase in relation to beta-aminoisobutyric aciduria," *Biochim. Biophys. Acta.* 156(2):374-380 (1968).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Kizer et al., "Application of Functional Genomics to Pathway Optimization for Increased Isoprenoid Production," *Appl. Environ. Microbiol.* 74(10):3229-3241 (2008).

Fishbein and Bessman, "Purfication and properties of an enzyme in human blood and rat liver microsomes catalyzing the formation and hydrolysis of γ-lactones. II. Metal ion effects, kinetics, and equilibra," *J. Biol. Chem.* 241(21):4842-4847 (1966).

Perez-Prior et al., "Reactivity of lactones and GHB formation," *J. Org. Chem.* 70(2):420-426 (2005).

\* cited by examiner

1. Calandria
2. Separator
3. Condensor

PROCESS OF SEPARATING COMPONENTS OF A FERMENTATION BROTH

This application claims the benefit of priority of U.S. Provisional Application Ser. No. 61/184,292, filed Jun. 4, 2009, the entire contents of which are incorporated herein by reference.

BACKGROUND OF THE INVENTION

This invention relates generally to the separation of components of a fermentation broth and, more specifically to the isolation of water miscible compounds having boiling points higher than water from other fermentation broth components.

Environmental and cost reduction incentives exist to design process schemes that have the ability to separate and optionally recycle components in a fermentation including the cell mass, residual media and media salts, residual substrate such as sucrose and/or glucose, and water. Efforts have also been made to recycle cell mass as a means to improve the fermentation productivity. Less effort has been made in the area of recovering the residual media and media salts for reuse in the fermentation. In this regard, most efforts have focused on reducing initial media costs, rather than downstream recovery. The resulting "low cost" media is often not optimal for cell growth and product production. By developing effective methods for the recovery of media components, a more optimal media recipe can be utilized with fewer restrictions on initial raw material costs.

The isolation of compounds on large scale with useful purity is a complex challenge in process chemistry. Differences in scale alone can render isolation procedures developed on laboratory benchtop scale impractical or even not viable at pilot or commercial scales. Isolation of compounds from complex mixtures depends on numerous factors including whether the compound is a solid or liquid at ambient temperatures, the compounds boiling point, density, polarity, the presence or absence of pH sensitive functional groups, and solubility in organic solvents versus water. These factors also apply to all other components of the mixture from which the compound of interest is to be isolated. Another property that factors into isolation of a compound, organic compounds in particular, is how it partitions between two immiscible phases, such as between water and an organic solvent. Compounds that are particularly polar are often more soluble in water than in common organic solvents used in extraction processes. Some compounds are particularly challenging to isolate from water by extractive methods due to their amphiphilic character. Amphiphiles are compounds that possess both a polar portion and a lipophilic portion. These compounds can complicate isolation by extraction by causing intractable emulsions.

Moreover, when a compound is prepared from a fermentation the amount of water can be substantially higher than the compound of interest, requiring isolation of a minor component from a complex mixture. Isolation of compounds that boil at a higher temperature than water further adds to the complexity and cost of the separation since the compound cannot be distilled directly from the fermentation broth as is the case, for example, in an ethanol fermentation process. In this regard, interactions between the compound of interest and water can cause the two entities to co-distill as an azeotrope at a boiling point different from the two purified components. Azeotrope formation is not readily predictable. This can diminish recovery of the compound of interest when trying to separate it from water. When a compound has polar functional groups another concern is how it may interact with other compounds present in the water phase, including any salts and metal ions, for example.

The nature of the functional groups present in a compound of interest can complicate the separation of salts. For example, one or more functional groups of a compound can interact with or chelate cations or anions. Chelation occurs in a size dependent manner with respect to the cation or anion and is also dependent on the disposition of the functional groups on the compound of interest. Chelation and other interactions can render some salts soluble in a liquid compound even in the absence of water, while other salts can be insoluble in the absence of water despite the presence of a compound with functional groups capable of interacting with salts. These types of effects on salt solubility are difficult to predict. Further adding to the complexity of the interaction between a compound and salts, is the nature of any co-solvents. For example, during the isolation of a compound of interest that is water miscible, hydrogen bonding and other interactions with water can disrupt the interaction between the salts and the compound of interest. Thus, in some cases a salt can be separated more readily from a compound in the presence of some amount of water. However, the amount of water that balances salt supersaturation allowing salt separation by crystallization, for example, while maintaining water's ability to disrupt chelation and other interactions between a compound of interest and any salts is difficult to predict.

Yet a further challenge in developing isolation methods is the potential reactivity of biosynthetic byproducts such as organic acids, excess substrate, and the like. Under conditions of heating, excess substrate can degrade and cause undesirable coloration of product. Additionally, some byproducts can react with the product of interest, effectively lowering isolation yields. These byproducts can include those formed during fermentation as well as byproducts formed during steps of the isolation procedure itself, for example due to degradation processes at elevated temperatures during a distillation, water evaporation, and the like.

Thus, there is a need to develop processes that allow for the isolation of water miscible compounds that have boiling points higher than water from microbial fermentations, while bearing in mind the environmental and cost benefit of recycling other fermentation components. The present invention satisfies this need and provides related advantages as well.

SUMMARY OF THE INVENTION

In some aspects, embodiments disclosed herein relate to process of isolating 1,4-butanediol (1,4-BDO) from a fermentation broth that includes separating a liquid fraction enriched in 1,4-BDO from a solid fraction comprising cells, removing water from said liquid fraction, removing salts from said liquid fraction, and purifying 1,4-BDO.

In other aspects, embodiments disclosed herein relate to a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by evaporative crystallization, removing a further portion of salts from the liquid fraction by ion exchange, and distilling 1,4-BDO.

In still other aspects, embodiments disclosed herein relate to a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by nanofiltration, removing a further portion of salts from the liquid fraction by ion exchange, evaporating a portion of water, and distilling 1,4-BDO.

In yet still other aspects, embodiments disclosed herein relate to a process for producing 1,4-BDO that includes culturing a 1,4-BDO-producing microorganism in a fermentor for a sufficient period of time to produce 1,4-BDO. The 1,4-BDO-producing microorganism includes a microorganism having a 1,4-BDO pathway including one or more exogenous genes encoding a 1,4-BDO pathway enzyme and/or one or more gene disruptions. The process further includes isolating 1,4-BDO according to the described isolation processes.

DETAILED DESCRIPTION OF THE INVENTION

Figure 1:
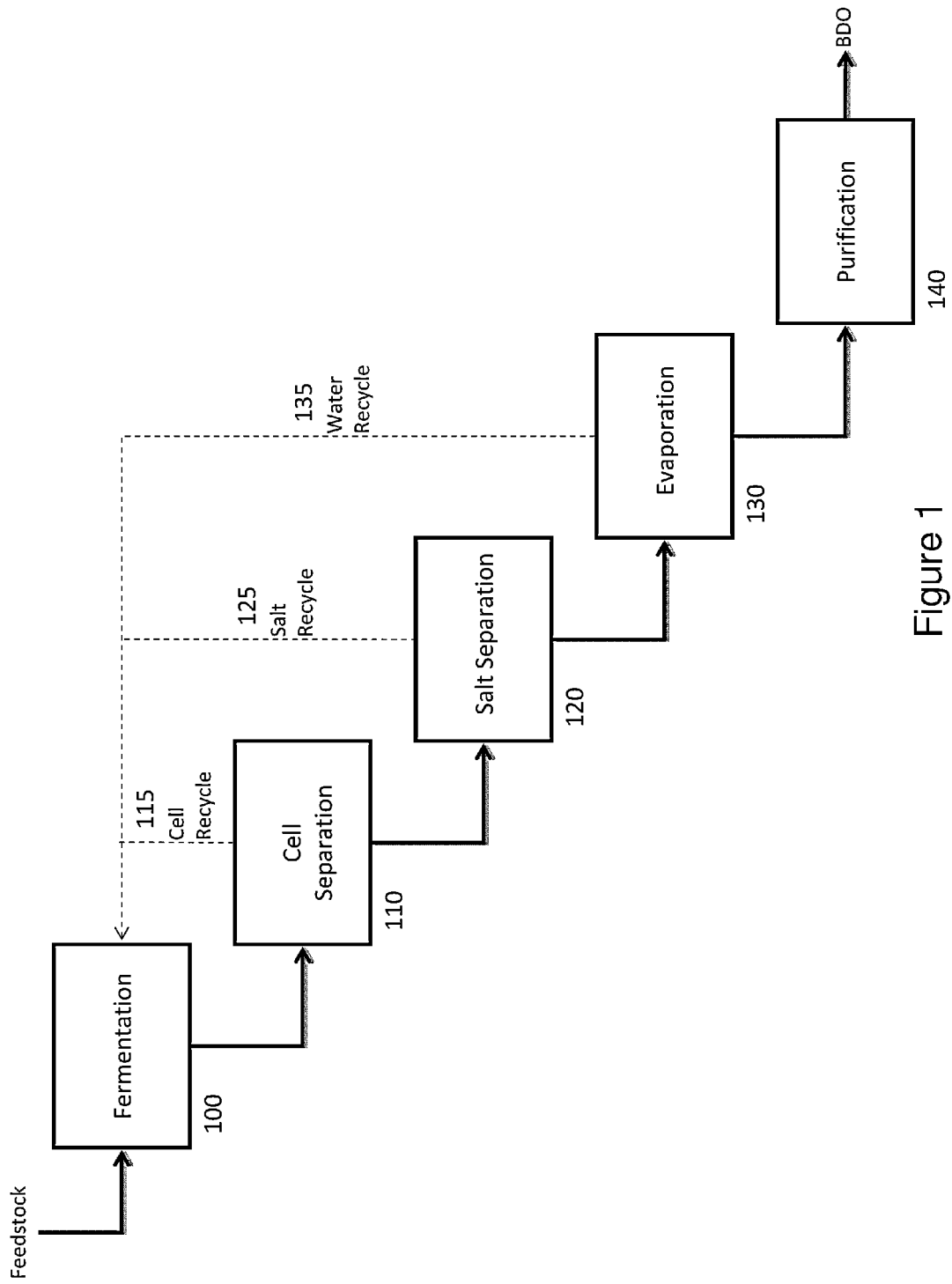
FIG. 1 shows a block diagram of steps in the process of purifying 1,4-BDO from a fermentation broth.

Fermentation production of commodity chemicals is a useful alternative to traditional production using nonrenewable fossil fuel feedstocks. With the ability to utilize renewable feedstocks such as recycled biomass and the like, the process can prove more economical and environmentally sound than fossil fuel based production. Products generated from fermentation can be useful in many applications. In specific embodiments, the present invention provides methods for the production of 1,4-BDO. 1,4-Butanediol (BDO) is a polymer intermediate and industrial solvent. Downstream, butanediol can be further transformed; for example, by oxidation to gamma-butyrolactone, which can be further converted to pyrrolidone and N-methyl-pyrrolidone, or it can undergo hydrogenolysis to tetrahydrofuran. These compounds have varied uses as polymer intermediates, solvents, and additives.

This invention is directed, in part, to processes for isolating water miscible compounds having boiling points higher than water from a fermentation while optionally allowing recycle of other components of the fermentation broth. The process separates out cell mass, which can include microbial organisms that have been engineered with gene insertions, gene disruptions or a combination of insertions and disruptions to produce compounds in useful yields from a suitable feedstock.

The cell-free broth, or liquid fraction, can be further processed by removal of salts. This can be achieved by several methods before or after removal of some or substantially all of the water from the fermentation broth. As described above, salts are not often recovered for recycle in a fermentation process. Usually any salt recovery involves a salt form of a desired biosynthetic product such as lactate, citrate or other carboxylate product or ammonium salts of amine-containing products, rather than media salts and the like. The process described herein allows for recovery of media salts and optional recycle back into fermentation. The isolation process also involves removal of water, which can be reintroduced into the fermentation system. In the final purification, the compound produced by fermentation can be distilled, or recrystallized if solid, from the remaining liquid fraction after removal of cells, salts, and water. In the case of a liquid, the final purification can be accomplished by fractional distillation, for example.

In some embodiments, the invention is directed to a process of isolating a water miscible compound of interest having a boiling point higher than water from a fermentation broth. The process includes (1) separating a liquid fraction enriched in the compound from a solid fraction that includes cells; (2) removing water from the liquid fraction; (3) removing salts from the liquid fraction, and (4) purifying the compound of interest by distillation or recrystallization. Steps (2) and (3) above may be performed in either order, or together.

Compounds of interest with boiling points higher than water that are accessible via fermentation, can have boiling points 10° C., 20° C., 30° C., 40° C., 50° C., 60° C., 70° C., 80° C., 90° C., 100° C., 150° C., 200° C. and 300° C. higher than water and more, including all values in between. Compounds of interest having higher boiling points than water can include, for example, 1,4-BDO, 1,3-BDO, 2,3-BDO, 1,3-PDO, 1,2-PDO (methyl ethyl glycol), 1,2-ethandiol (ethylene glycol), gamma-butyrolactone (GBL), 1,5-pentanediol, 1,6-hexanediol. Furthermore, compounds of interest include those that are water miscible. In some embodiments, such water miscible compounds can be recalcitrant to conventional extraction procedures. Additionally, compounds of interest include those that are neutral. As used herein, a neutral compound refers to a compound that does not possess functional groups capable of carrying charge, such as amines, carboxylic acids, sulfonic acids, boronic acids and the like. Finally, compounds of interest can be sufficiently small so as to be permeable to a nanofiltration membrane, as described further below. Exemplary compound classes include alcohols, diols, triols, such as glycerin, tetraols, polyols and the like.

In one specific embodiment, the compound of interest is 1,4-BDO. 1,4-BDO has a boiling point of about 230° C. and is completely miscible with water. Moreover, there are no solvents that have been identified that can economically extract 1,4-BDO from the water. As a neutral molecule, isolation by crystallization of a salt form is precluded. 1,4-BDO has a molecular weight sufficiently low to pass through a nanofiltration membrane as described in Example III below. Furthermore, the solubility of various fermentation media salts in pure 1,4-BDO is relatively low, as described in Example VI below.

In some embodiments, the present invention provides a process of isolating 1,4-butanediol (1,4-BDO) from a fermentation broth that includes (1) separating a liquid fraction enriched in 1,4-BDO from a solid fraction that includes cells;

(2) removing water from the liquid fraction; (3) removing salts from the liquid fraction, and (4) purifying 1,4-BDO.

One skilled in the art will recognize that given the guidance of the teachings disclosed herein with respect to the exemplary compound 1,4-BDO, other water miscible compounds of interest having boiling points higher than water can be isolated using the same procedures. For example, the methods disclosed herein are readily modified to enable the isolation of 1,3-butanediol. Therefore, although many embodiments are exemplified by 1,4-BDO, it is understood that the methods are readily adaptable to other water miscible compounds of interest having boiling points higher than water.

In some embodiments, the invention is directed to a process of isolating 1,4-butanediol (1,4-BDO) from a fermentation broth. The process includes separating a liquid fraction enriched in 1,4-BDO from a solid fraction that includes cells. Water is evaporated from the liquid fraction before or after separating salts from the liquid fraction. In some embodiments 1,4-BDO is separated from salts that have crystallized after water removal as described further below. The salts have a low solubility in 1,4-BDO such that the separated 1,4-BDO is about 98% salt-free. In some embodiments, salts are separated by special filtration methods and/or ion exchange, or chromatographic methods prior to water removal as described further below.

As used herein, "isolating" refers to a process that includes purification steps to obtain a substantially purified compound of interest. In particular embodiments, a compound of interest includes 1,4-BDO. A substantially purified compound includes those that are at least 98% salt free, in some embodiments, at least 99% salt free in other embodiments, and at least 99.5% salt free in still other embodiments. A substantially purified compound also includes those that are also free of other impurities in addition to salts such that the compound of interest is at least 98% pure in some embodiments, at least 99% pure in other embodiments, and at least 99.5% pure in still further embodiments.

As used herein, the term "liquid fraction" refers to a centrate or supernatant liquid obtained upon removal of solid mass from the fermentation broth. Solid mass removal includes, some, substantially all, or all of a solid mass. For example, in centrifugation, the liquid fraction is the centrate or supernatant which is separated from the solids. The liquid fraction is also the portion that is the permeate or supernatant obtained after filtration through a membrane. The liquid fraction is also the portion that is the filtrate or supernatant obtained after one or more filtration methods have been applied.

As used herein, the term "solid fraction" refers to a portion of the fermentation broth containing insoluble materials. Such insoluble materials include, for example, cells, cell debris, precipitated proteins, fines, and the like. Fines refer to small, usually amorphous solids. Fines can also be created during crystallization or during removal of water from the fermentation broth. Fines can be made up of a compound of interest which can be dissolved and recrystallized out. Fines can include portions of the solid fraction that are too small to be captured in a membrane filtration.

As used herein, the term "salts," used interchangeably with media salts and fermentation media salts, refers to the dissolved ionic compounds used in a fermentation broth. Salts in a fermentation broth can include, for example, sodium chloride, potassium chloride, calcium chloride, ammonium chloride, magnesium sulfate, ammonium sulfate, and buffers such as sodium and/or potassium and/or ammonium salts of phosphate, citrate, acetate, and borate.

As used herein, the term "substantially all" when used in reference to removal of water or salts refers to the removal of at least 95% of water or salts. "Substantially all" can also include at least 96%, 97%, 98%, 99%, or 99.9% removal or any value in between.

As used herein, the term "gene disruption" or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation strategies that inactivate the encoded gene product. One particularly useful method of gene disruption is complete gene deletion because it reduces or eliminates the occurrence of genetic reversions in the non-naturally occurring microorganisms of the invention.

As used herein, the term "microorganism" is intended to mean a prokaryotic or eukaryotic cell or organism having a microscopic size. The term is intended to include bacteria of all species and eukaryotic organisms such as yeast and fungi. The term also includes cell cultures of any species that can be cultured for the production of a biochemical.

As used herein, the term "1,4-BDO-producing microorganism" is intended to mean a microorganism engineered to biosynthesize 1,4-BDO in useful amounts. The engineered organism can include gene insertions, which includes plasmid inserts and/or chromosomal insertions. The engineered organism can also include gene disruptions to further optimize carbon flux through the desired pathways for production of 1,4-BDO. 1,4-BDO-producing organisms can include combination of insertions and deletions.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

In some embodiments, the invention provides a process of purifying a compound of interest from a fermentation broth. Applicable compounds include those having a boiling point higher than water and a low salt solubility. Compounds of interest also include those that are water miscible. An exemplary compound of interest is 1,4-BDO. The process includes separating a liquid fraction which contains the product of interest, from a solid fraction which includes the cells mass. The product of interest can be any compound having a higher boiling point than water. The cell mass includes the microbial organisms used in the production of the compound of interest. The solid fraction also includes cell debris, fines, proteins, and other insoluble materials from the fermentation.

The isolation process also includes removing the salts and water from the liquid fraction. The order in which they are removed is inconsequential. In some embodiments, there can be partial removal of salts, followed by removal of substantially all the water, and then the remaining salts. In other embodiments, there can be partial removal of water, followed by removal of substantially all of the salts, and then the remaining water. In other embodiments, water can be partially removed prior to separation of the solid fraction from the fermentation broth. In still other embodiments, final removal of substantially all the water can be done as part of the purification steps, for example by distillation. As disclosed below in Example VI, neat 1,4-BDO does not appreciably solubilize typical fermentation media salts. Thus, 1,4-BDO can be separated from salts by evaporation of the water from the liquid fraction. As shown in Example V below, salts begin to crystallize out when 1,4-BDO concentrations are about 30% by weight. In some embodiments, 1,4-BDO is a least 98% salt free upon separation of 1,4-BDO from salts crystallized or precipitated by water removal. As can be seen from Example VI, closely related homologues ethanediol and propane diol still appreciably solubilize fermentation salts. Thus, other methods can be employed to remove salts even after removal of substantially all the water.

Eventually when the salts and water have been removed, the remaining liquid or solid can undergo final purification. When the product of interest is a liquid, purification can be accomplished by distillation including by fractional distillation or multiple distillation, for example. When the product of interest is a solid, purification can be accomplished by recrystallization.

The overall process for producing and isolating a compound of interest and recycling various components of the fermentation broth are summarized in the block flow diagram of FIG. 1. Step 100 is fermentation utilizing carbon feedstock, such as sucrose, to produce the compound of interest. Step 110 is the separation of cells from the fermentation broth providing a liquid fraction, with Step 115 as an optional recycle of the cells. Step 110 has been exemplified in Examples I and II in which cells and solids are separated form fermentation broth by centrifugation and ultrafiltration. In Step 120, salts are separated from the liquid fraction, with Step 125 as an optional recycle of the salts. Step 120 has been exemplified in Examples III-V, which describe nanofiltration (Example III) and ion exchange (Example IV), in which water is still present in the liquid fraction. Example V shows the separation of salts through crystallization during water evaporation. Step 130 is the removal of water via evaporation, with Step 135 as an optional recycle of the water. Step 130 is exemplified by Example V, which show the evaporation of water which facilitates salt separation by precipitation. The order of Steps 120 and 130 are interchangeable as described further below. Finally in step 140 the compound of interest undergoes final purification.

In some embodiments, a process of isolating a compound of interest, including 1,4-BDO, from a fermentation broth involves separating a liquid fraction enriched in the compound of interest from a solid fraction that includes cells. In separating a liquid fraction enriched in the compound of interest, any amount of the fermentation broth can be processed including 1%, 5%, 10%, 20%, 30%, 40%, 50%, 60%, 70%, 80%, 90%, including up to the entirety of the volume of the fermentation broth and all values in between, and further including volumes less than 1% of the total volume of the fermentation broth. One skilled in the art will recognize that the amount of fermentation broth processed can depend on the type of fermentation process, such as batch, fed batch, or continuous, as detailed below. Separation of solids which includes cells and other solid byproducts and impurities from the fermentation broth can be accomplished by centrifugation, filtration, or a combination of these methods.

Figure 2:
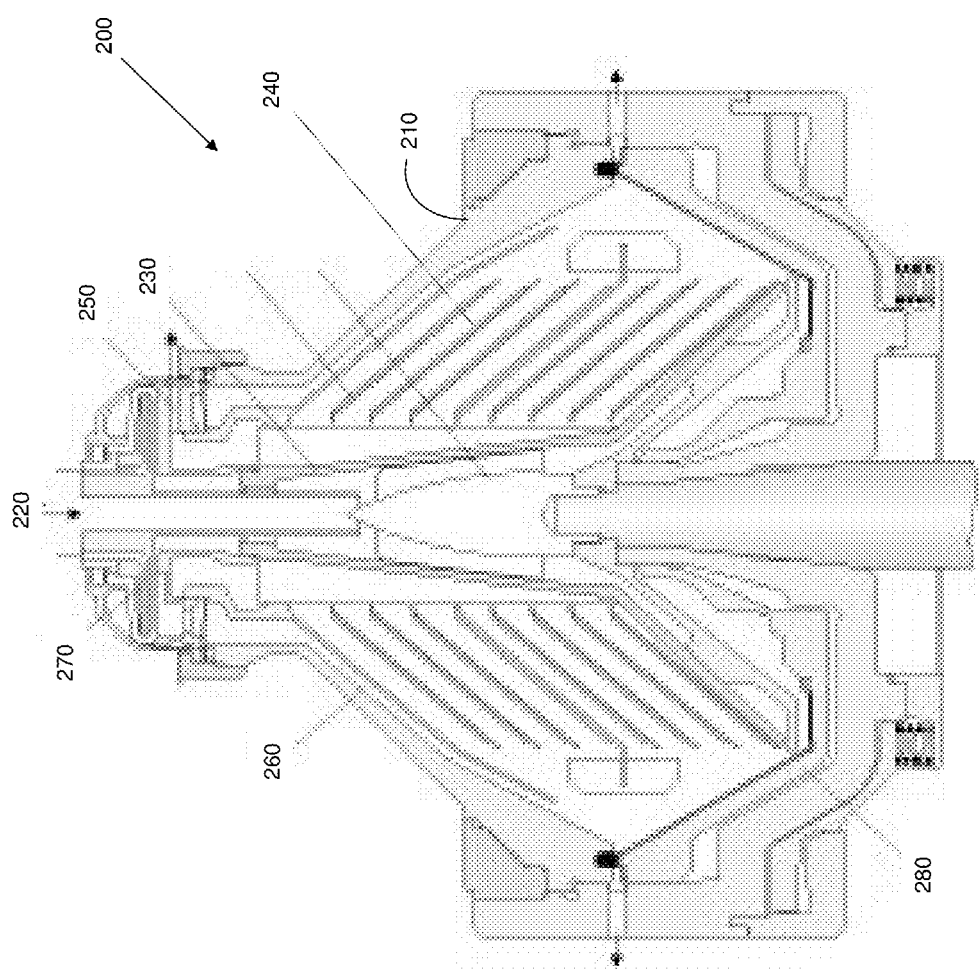
FIG. 2 shows a cross-section view of disc-stack centrifuge.

In some embodiments, centrifugation can be used to provide a liquid fraction comprising the compound of interest, such as 1,4-BDO, substantially free of solids including the cell mass. Depending on the centrifuge configuration and size, operating speeds can vary between 500 to 12,000 rpm which produce a centrifugal force of up to 15,000 times the force of gravity. Many centrifuge configurations for removal of cells and solids from a fermentation broth are known in the art. One such configuration, for example, is the disc-stack centrifuge 200 shown in FIG. 2.

Separation in a disc-stack centrifuge takes place inside a rotating bowl 210. The feed is introduced to the rotating bowl from the top via a stationary inlet pipe 220, and is accelerated in the distributor 230, before entering the disc stack 240. The distributor is designed accelerate the feed liquid.

The separation of liquid-solids or liquid-liquid-solids takes place between the discs. In a two phase system, such as with immiscible oil and water phase, the oil phase moving through the disc stack to the centre and can be discharged through pipes 250 and sprayed out into a collecting frame. The water and solids separated from the oil move to the periphery, the water is led via channels in the top disc 260 to the paring chamber, where it is pumped out of the rotor with means of a built-in paring disc 270.

The solids are collected in the periphery, from where it can be discharged intermittently via a centrifuge cyclone. The solids discharge can be achieved by a hydraulic system which at preset suitable intervals forces the sliding bowl bottom 280 to drop down opening the solids port at the bowl periphery.

A disc stack centrifuge separates solids and one or two liquid phases from each other, typically in a continuous process. The denser solids are forced outwards by centrifugal forces while the less dense liquid phases form inner concentric layers. By inserting special plates (disc stack) separation efficiency is increased. The solids can be removed manually, intermittently or continuously. In accordance with some embodiments, the cell mass can be introduced back into the fermentation. In a typical disc-stack centrifuge apparatus, the liquid phase overflows in an outlet area on top of a bowl into a separate chamber.

During operation of a disc-stack centrifuge, feed is introduced at the axis of the bowl, accelerated to speed, often by a radial vane assembly, and flows through a stack of closely spaced conical disks. Disk spacing is often between 0.5 to 3 mm in order to reduce the distance needed for separating settling particles from the fluid. The disc angle is often between 40 and 50 degrees to facilitate solids transport down the disk surface into the solids holding space.

The separating mechanism is based on the settling of solids under the influence of centrifugal force against the underside of the disks and slide down the disk into the solids hold space. Concurrently the clarified fluid moves up the channel between the disks and leaves the centrifuge via a centripetal pump. The settled solids are discharged either continuously though nozzles or intermittently through ports at the bowl periphery.

The disc-stack centrifuge can be used at low concentration and particle size of cells in a fermentation broth. A disc-stack centrifuge can be employed when the cell and other solid mass includes as little as about 0.2% to about 3% by weight of the fermentation broth. The disc-stack centrifuge can also be used when the cell and other solid mass is less than about 0.2% by weight, for example, 0.01%, 0.05%, and 0.1% by weight, including all values in between. The disc-stack centrifuge can also be used when the cell and other solid mass is more than 3% by weight, for example, 4%, 5%, 6%, 7%, 8%, 9%, 10%, and 15% by weight, including all values in between. When the combined cell mass and other solids is higher than about 3% to about 15% by weight other centrifugation configurations can be used, such as a decanter centrifuge.

Cells and other solid particles that are soft, plastic, and not abrasive, ranging from about 0.5 microns to about 500 microns are generally well-suited for disc-centrifugation. For particulate matter less than about 0.5 microns, ultrafiltration is useful. Likewise, above about 500 microns, a decanter-type centrifuge can be useful. The size of a typical prokaryotic cell that can be cultured to produce a compound of interest, including 1,4-BDO, can range in size from about 0.5 microns to about 10 microns, making disc-stack centrifugation a well-suited method.

Following batch, or during fed-batch or continuous fermentation, cells and insoluble solids can be removed from the fermentation broth by a disc-stack centrifuge. Outputs from a disc-stack centrifuge are a clarified (cell-free) centrate and an underflow stream containing about 5% to about 50% solids. The underflow solids stream from the disc stack centrifuge can contain a significant amount of the product of interest which can be recovered. One way to recover additional compound of interest from the solids is to include further centrifugation steps. In addition to providing greater recovery of the compound of interest, multiple centrifugation also serves to further concentrate the cells and solids. The concentrated cells can be recycled back to the fermentation. Cell recycle is particularly useful when valuable engineered organisms are being used.

In some embodiments, a decanter centrifuge can be employed to separate out the cells and solids. Good performance with a decanter centrifuge is normally realized with solids having particle sizes with a lower limit approaching about 10 microns, although smaller particles can be processed depending on their settling speed as described further below. This centrifuge configuration can be used when the cells of a culture are at the larger size range of a typical prokaryotic organism. One skilled in the art will appreciate that eukaryotic cells are often much larger than prokaryotic cells, with an average eukaryotic cell ranging in size from about 10 microns to about 100 microns or larger. Although a disc-stack centrifuge can operate well in this size range, a decanter centrifuge is useful because it is able to handle larger amounts of solids. Thus, when the cell mass plus other solids is more than about 3 to about 50% of the mass by weight, a decanter centrifuge can be used. This concentration applies to the underflow of the disc stack centrifuge described above, making a decanter centrifuge a well suited method to further concentrate the cell mass and recover additional product.

Figure 3:
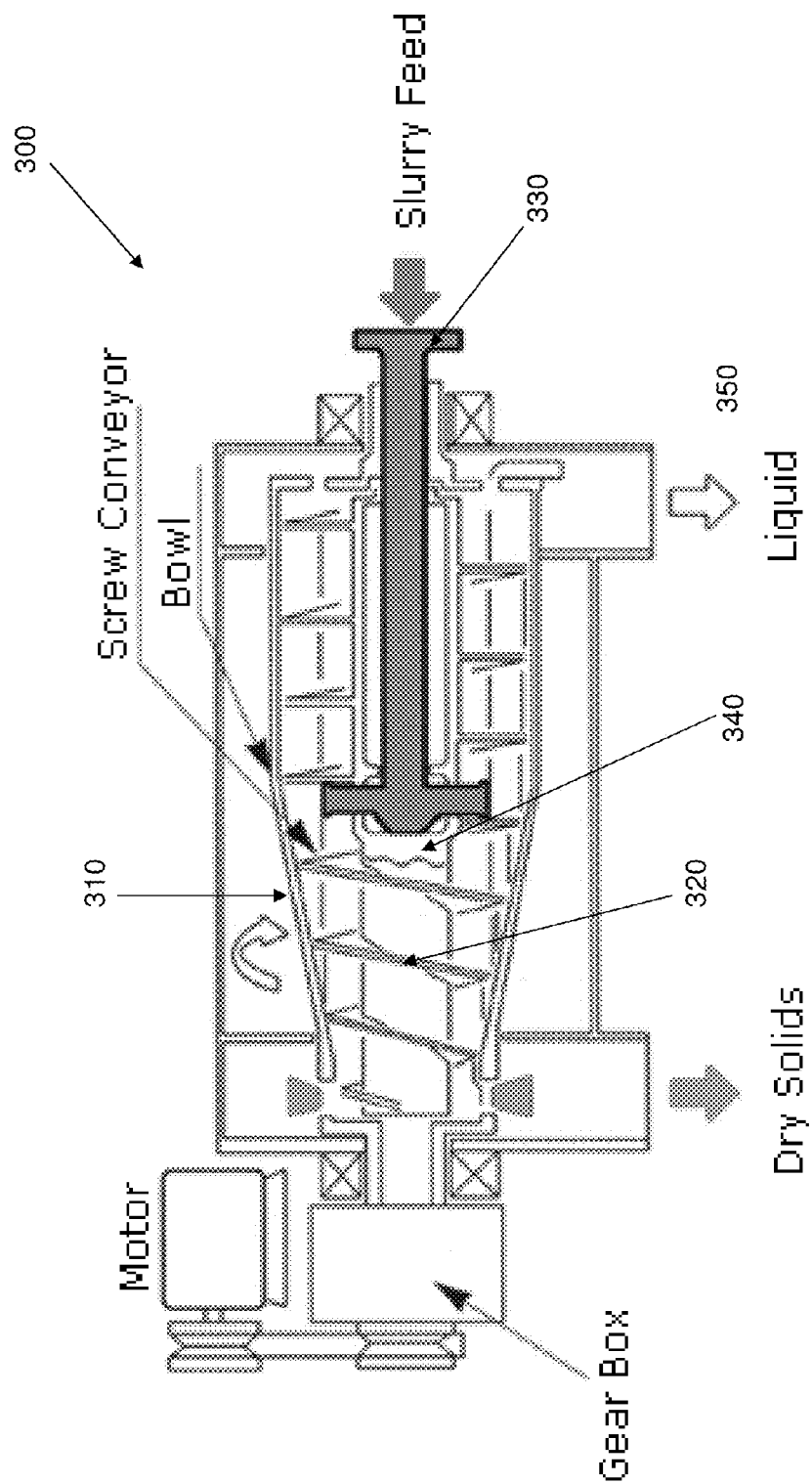
FIG. 3 shows a cross-section view of a decanter centrifuge.
Figure 4:
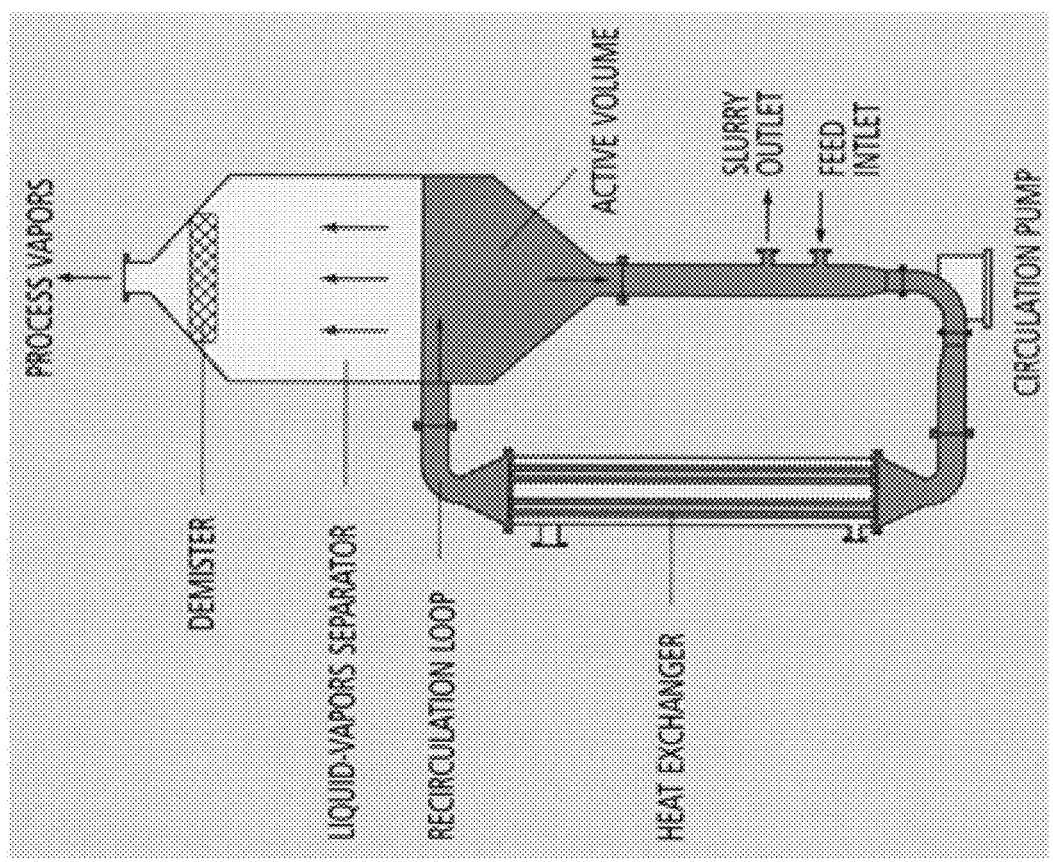
FIG. 4 shows a diagram of a forced circulation crystallizer.

The decanter, or solid bowl, centrifuge operates on the principle of sedimentation. Exemplary apparatus are described in U.S. Pat. Nos. 4,228,949 and 4,240,578, which are incorporated herein by reference in their entirety. In such an apparatus 300, as shown in FIG. 3, the central part of the machine is a rotating drum 310, which contains an independently rotating screw, 320. The fermentation broth or solids-containing feed, such as the underflow from the disc stack centrifuge, is fed via the inlet pipe 330 to the mixing chamber 340 in the core of the first part of the screw. The broth then passes through ports in the mixing chamber out towards the outer walls of the drum. The dewatered broth is transported out through the machine by the screw. The centrate 350, or supernatant, is decanted from the inner surface of the pond through centrate pipes. The water level in the drum can be adjusted in accordance with the characteristics of the material to be processed.

The drum and the screw rotate independently of one another at speeds up to about 3,600 rpm, depending on the type and size of machine. The dewatering principles used are known in the art as the "concurrent" or "counter-current" method. The concurrent method permits very low differential speeds. The differential speed is the difference between the speed of the drum and the speed of the screw. Low differential speeds mean longer residence times in the centrifuge, which result in drier sludge and considerably less wear. The counter-current principle can be more suitable for a feed that is easy to dewater and when a high capacity is desired.

Solids can be separated in solid bowl centrifuges provided their sedimentation speed in the liquid phase portion of the feed is sufficient. Factors that influence sedimentation speed include, for example, particle size, shape, differences in density between the cells/solids and the fermentation broth liquid phase, and viscosity. The geometry of the bowl, especially the relation between the length and diameter, are adaptable to suit the particular conditions. In some embodiments, good results can be obtained at length diameter ratio ranging from about 2:1 to about 3:1.

In operation, separation takes place in a horizontal conical cylindrical bowl equipped with a screw conveyor. The fermentation broth is fed into the bowl through a stationery inlet tube and accelerated by an inlet distributor. Centrifugal force provides the means for sedimentation of the solids on the wall of bowl. A conveyor, rotating in the same direction as bowl with differential speed, conveys the solids to the conical end. The solids are then lifted clear of the liquid phase and centrifugally dewatered before being discharged into a collecting channel. The remaining liquid phase then flows into a housing through an opening in cylindrical end of the bowl.

As described above, the cells and solids can be separated by multiple centrifugation to increase the isolated yield of the compound of interest. Multiple centrifugation can include centrifugation twice, three times, four times, and five times, for example. Intermediate underflow streams can be diluted with water to further increase recovery of the liquid product. Any combination of centrifugation configurations can also be used to perform multiple centrifugations, such as combinations of the disc-stack and decanter centrifugations described above. Further solids that are not separable by centrifugation can be removed through a filtration process, such as ultrafiltration.

Ultrafiltration is a selective separation process through a membrane using pressures up to about 145 psi (10 bar). Useful configurations include cross-flow filtration using spiral-wound, hollow fiber, or flat sheet (cartridge) ultrafiltration elements. These elements consist of polymeric or ceramic membranes with a molecular weight cut-off of less than about 200,000 Daltons, for example Hydranautics 5K PES membrane as used in Example I below. Ceramic ultrafiltration membranes are also useful since they have long operating lifetimes of up to or over 10 years. Ceramics have the disadvantage of being much more expensive than polymeric membranes. Ultrafiltration concentrates suspended solids and solutes of molecular weight greater than about 1,000 Daltons. Ultrafiltration includes filtering through a membrane having nominal molecular weight cut-offs (MWCO) from about 1,000 Daltons to about 200,000 Daltons (pore sizes of about 0.005 to 0.1 microns). The term molecular weight cut-off is used to define the size of protein that will be approximately 90% retained by the membrane. Using ultrafiltration the permeate liquid will contain low-molecular-weight organic solutes, such as 1,4-BDO, media salts, and water. The captured solids can include, for example, residual cell debris, DNA, and proteins.

In addition to the use ultrafiltration downstream of centrifugation, ultrafiltration can also be used downstream of microfiltration. Microfiltration provides an alternate means to centrifugation for separating cells. Microfiltration usually involves a low-pressure cross-flow membrane process for separating colloidal and suspended particles in the range of about 0.05-10 microns. Microfiltration includes filtering through a membrane having pore sizes from about 0.05 microns to about 5.0 microns. Polymeric, ceramic, or steel microfiltration membranes can be used to separate cells. Ceramic or steel microfiltration membranes have long operating lifetimes including up to or over 10 years. Microfiltration can be used in the clarification of fermentation broth. Unlike ultrafiltration, microfiltration will generally not capture residual cell debris, DNA, and proteins. However, it is useful to use a series of filtration steps with gradually decreasing pore size in order to avoid fouling of the filter membranes. This is useful for optimizing reuse of the filter membrane. In some embodiments, a single ultrafiltration step can be used to remove both cell mass (in place of centrifugation or microfiltration) and residual cell debris, DNA, proteins, etc. Ceramic ultrafiltration elements are useful for this application due to their ability to tolerate the frequent cleaning cycles used in this mode of operation.

In some embodiments, a further filtration method called nanofiltration can be used to separate out certain salts. This process step can allow the recovery of certain media salts without prior evaporation of water, for example. Nanofiltration can separate salts, remove color, and provide desalination. In nanofiltration, the permeate liquid generally contains monovalent ions and low-molecular-weight organic compounds as exemplified by 1,4-BDO. Nanofiltration includes filtering through a membrane having nominal molecular weight cut-offs (MWCO) from about 100 Daltons to about 2,000 Daltons (pore sizes of about 0.0005 to 0.005 microns). One method for nanofiltration is cross-flow filtration using a spiral-wound element. There are several nanofiltration membranes available, for example the thin film composite nanofiltration membrane GE DK used in Example III below. The mass transfer mechanism in nanofiltration is diffusion. The nanofiltration membrane allows the partial diffusion of certain ionic solutes (such as sodium and chloride), predominantly monovalent ions, as well as water. Larger ionic species, including divalent and multivalent ions, and more complex molecules are substantially retained.

Since monovalent ions are partially diffusing through the nanofiltration membrane along with the water, the osmotic pressure difference between the solutions on each side of the membrane is not as great and this typically results in somewhat lower operating pressure with nanofiltration compared with, for example, reverse osmosis.

Nanofiltration not only removes a portion of the inorganic salts but can also remove salts of organic acids. The removal of organic acid byproducts can be important in the isolation process because such acids can catalyze or serve as a reactant in undesirable side reactions with a product of interest. In the context of specific embodiments related to the isolation of 1,4-BDO, for example, the removal of organic acids is particularly useful because it can prevent reactions such as esterification of the hydroxyl groups during the elevated temperatures of any downstream evaporation or distillation steps. These ester byproducts typically have higher boiling points than BDO resulting in yield losses to the heavies stream in distillation.

Nanofiltration can also separate the glucose or sucrose substrate from the product of interest, preventing degradation reactions during evaporation and distillation. These degradation reactions can produce coloration of the compound of interest. The salt and substrate rich nanofiltration retentate can be better suited for recycle to fermentation compared to a recovered salt stream from evaporative crystallization. For example, the use of filtration methods in lieu of methods involving application of heat can result in fewer degradation products. Such degradation products can be toxic to the fermentation organism.

Both nanofiltration and ion exchange can remove color forming compounds and UV absorbing compounds. This can be useful in the context of some compounds of interest. For example, color removal is useful in the production of polymer grade 1,4-BDO.

Multiple filtration membranes can be used serially with gradually increasing refinement of the size of the solids that are retained. This can be useful to reduce fouling of membranes and aid in recovering individual components of the fermentation broth for recycle. For example, a series of filtrations can utilize microfiltration, followed by ultrafiltration, followed by nanofiltration. Thus, microfiltration aids in recovery of cell mass, ultrafiltration removes large components such as cell debris, DNA, and proteins, and nanofiltration aids in recovery of salts.

Those skilled in the art will recognize that any of the various filtration types can be integrated within the context of a variety of fermentation bioreactor configurations given the teachings and guidance provide herein. In some embodiments the filtration occurs external to the bioreactor. In this mode, any amount of the fermentation broth can be removed from the bioreactor and filtered separately. Filtration can be aided by use of vacuum methods, or the use of positive pressure. In some embodiments, cell filtration can be accomplished by means of a filtration element internal to the bioreactor. Such configurations include those found in membrane cell-recycle bioreactors (MCRBs). Chang et al. U.S. Pat. No. 6,596,521 have described a two-stage cell-recycle continuous reactor.

In some embodiments, the cells can be separated and recycled into the fermentation mixture by means of an acoustic cell settler as described by Yang et al. (*Biotechnol. Bioprocess. Eng.*, 7:357-361(2002)). Acoustic cell settling utilizes ultrasound to concentrate the suspension of cells in a fermentation broth. This method allows for facile return of the cells to the bioreactor and avoids the issue of membrane fouling that sometimes complicates filtration-type cell recycle systems.

With respect to isolation of salts prior to water evaporation, other methods can be used alone, or in combination with the above exemplary filtration processes. Such other methods include, for example, ion exchange. For example, Gong et al. (*Desalination* 191:1-3, 193-199 (2006)) have described the effects of transport properties of ion-exchange membranes on desalination of 1,3-propanediol fermentation broth by electrodialysis.

Ion exchange elements can take the form of resin beads as well as membranes. Frequently, the resins are cast in the form of porous beads. The resins can be cross-linked polymers having active groups in the form of electrically charged sites. At these sites, ions of opposite charge are attracted but may be replaced by other ions depending on their relative concentrations and affinities for the sites. Ion exchangers can be cationic or anionic, for example. Factors that determine the efficiency of a given ion exchange resin include the favorability for a given ion, and the number of active sites available. To maximize the active sites, large surface areas are generally useful. Thus, small particles are useful because of their large surface area.

The resin polymer can include cross-linking on the order of about 0.5 to about 15 percent, for example. Temperature and pH also affect the efficiency of ion exchange. For example, pH can affect the number of ions available for exchange, and temperature affects the kinetics of the process. In some embodiments, salt removal by ion exchange includes removal of organic acids and salts of organic acids. The anionic form of organic acids can bind to an anion exchange active site. In some embodiments, the pH for binding an organic acid is below the pKa for that acid. The pKa of lactic acid, for example, is about 3.1. An effective method for removing salts of organic acids is cation exchange followed by anion exchange. The cation resin first removes the organic acid counter-ion (calcium, sodium, ammonium, and the like), lowering the pH of the solution. The anion resin then binds the free acid.

A useful aspect of ion exchange is the facility with which the resin can be regenerated. The resin can be flushed free of the exchanged ions and contacted with a solution of desirable ions to replace them. With regeneration, the same resin beads can be used over and over again, and the isolated ions can be concentrated in a waste effluent. As with the many filtration methods, serial ion exchange can be performed, as exemplified in Example IV. Thus, a feed can be passed through both any number of anionic and cationic exchangers, or mixed-bed exchangers, and in any order.

In some embodiments, water removal via evaporation is used to facilitate salt recovery. In some embodiments, the salts have been removed prior to water removal. In either case, evaporated water can be recycled as makeup water to the fermentation, minimizing the overall water requirements for the process. In the case where the salts have not been removed, their solubility in the 1,4-BDO enriched liquid phase is sufficiently low that they can crystallize after water removal. In some embodiments the salts have a sufficiently low solubility in 1,4-BDO that the separated 1,4-BDO is about 98% salt-free.

An evaporative crystallizer can be used to generate precipitated salts which can be removed by centrifugation, filtration or other mechanical means. In the context of 1,4-BDO isolation, an evaporative crystallizer serves to remove water from the fermentation broth creating a liquid phase that has removed enough water to cause supersaturation of the fermentation media salts and subsequent crystallization in the remaining liquid phase or mother liquor. As demonstrated in Example V below, crystallization of salts begins at a 1,4-BDO concentration of about 30% by weight.

The mother liquor refers to the bulk solvent in a crystallization. Frequently, the mother liquor is a combination of solvents with different capacity to solublize or dissolve various solutes. In the context of the purification of 1,4-BDO from a fermentation broth, for example, the mother liquor includes the liquid fraction obtained after removing cells and other solids from the fermentation broth. In the context of isolating a compound of interest from a fermentation broth, the primary solute includes the fermentation media salts and organic acids.

Supersaturation in crystallization refers to a condition in which a solute is more concentrated in a bulk solvent than is normally possible under given conditions of temperature and pressure. The bulk solvent of the fermentation broth is water containing relatively smaller amounts of 1,4-BDO, for example, and dissolved salts and other media.

Figure 5:
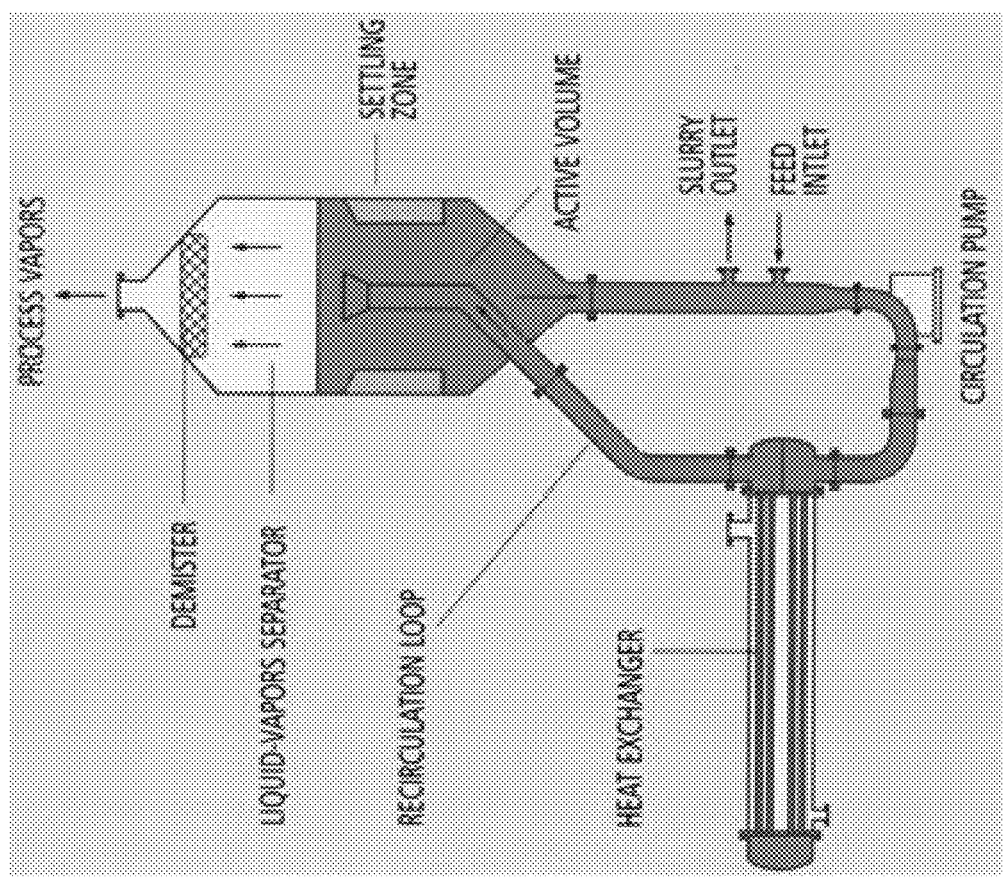
FIG. 5 shows a diagram of a forced circulation crystallizer with a horizontal heat exchanger and baffles in the active volume.
Figure 6:
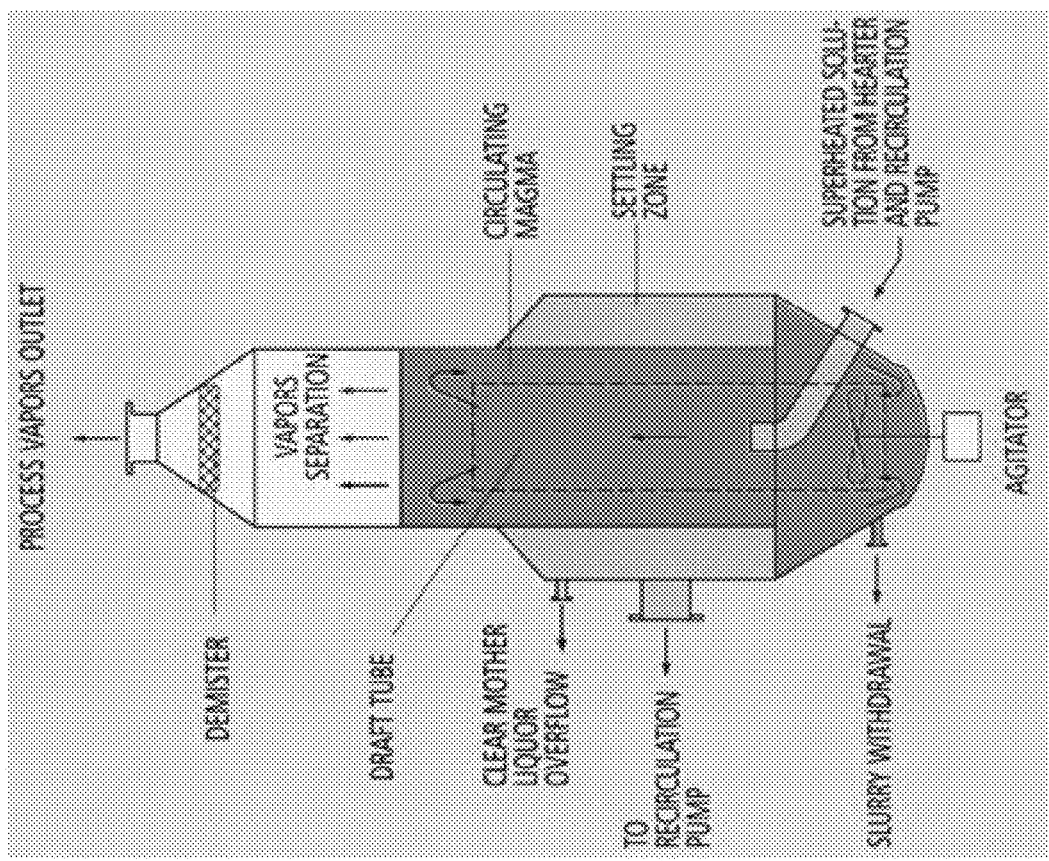
FIG. 6 shows a diagram of a draft tube and baffle crystallizer.

An exemplary evaporative crystallizer is the forced circulation (FC) crystallizer as shown in FIGS. 5 and 6. An FC crystallizer has been described, for example, in U.S. Pat. No. 3,976,430 which is incorporated by reference herein in its entirety. The FC crystallizer evaporates water resulting in an increased supersaturation of the salts in the compound-enriched (such as 1,4-BDO) liquid fraction thus causing the salts to crystallize. The FC crystallizer is useful for achieving high evaporation rates. The FC crystallizer consists of four basic components: a crystallizer vessel with a conical bottom portion, a circulating pump, a heat exchanger, and vacuum equipment which handles the vapors generated in the crystallizer. Slurry from the crystallizer vessel is circulated through the heat exchanger, and returned to the crystallizer vessel again, where supersaturation is relieved by deposition of salts on the crystals present in the slurry. The evaporated water is conducted to the vacuum system, where it is condensed and recycled to the fermentation broth as desired. Although in some embodiments, there is a low vacuum, it is also possible to use the FC crystallizer at about atmospheric pressure as well. In some embodiments, the FC crystallizer utilizes adiabatic evaporative cooling to generate salt supersaturation. In such embodiments, the FC crystallizer need not be equipped with a heat exchanger.

In some embodiments, the FC crystallizer can be further equipped with internal baffles, as shown in FIG. 6, to handle overflow of the liquid phase and to reduce fines which can inhibit crystal growth. The salts generated in the FC crystallizer can also be size selected with the aid of an optional elutriation leg. This portion of the FC crystallizer appears at the bottom of the conical section of the crystallizer vessel. Size selection is achieved by providing a flow of fermentation fluid up the leg allowing only particles with a particular settling rate to move against this flow. The settling speed is related to the size and shape of the crystals as well as fluid viscosity. In further embodiments, the FC crystallizer can also be equipped with an internal scrubber to reduce product losses. This can assist in the recovery of volatile products.

Figure 7:
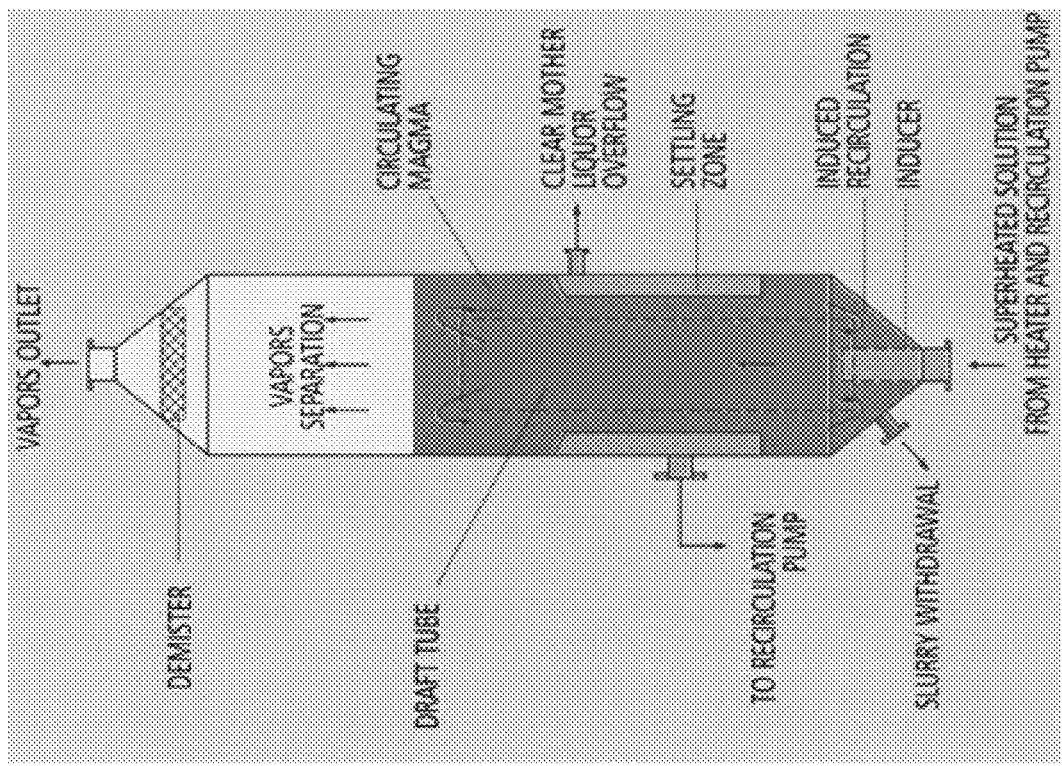
FIG. 7 shows a diagram of an induced circulation crystallizer.

The turbulence or draft tube and baffle "DTB" crystallizer, shown in FIG. 7, provides two discharge streams, one of a slurry that contains crystals, and another that is the liquid phase with a small amount of fines. The configuration of the DTB crystallizer is such that it promotes crystal growth, and can generate crystals of a larger average size than those obtained with the FC crystallizer. In some embodiments, the DTB crystallizer operates under vacuum, or at slight superatmospheric pressure. In some embodiments, the DTB crystallizer uses vacuum for cooling.

In some embodiments, a DTB crystallizer operates at a low supersaturation. One skilled in the art will appreciate that large crystals can be obtained under this regime. The system can be optionally configured to dissolve fines to further increase crystal size. When the DTB crystallizer is used in fermentation media salt recovery, crystal size is not necessarily a priority.

The DTB crystallizer has been studied widely in crystallization, and can be modeled with accuracy. Its distinct zones of growth and clarified liquid phase facilitate defining kinetic parameters, and thus, the growth and nucleation rate can be readily calculated. These features make the DTB crystallizer suitable to mathematical description, and thus, subject to good operating control. The DTB crystallizer is an example of a mixed suspension mixed product removal (MSMPR) design, like the FC crystallizer.

The DTB crystallizer includes a baffled area, serving as a settling zone, which is peripheral to the active volume. This zone is used to further process the liquid phase and fines. In some embodiments, the baffled area is not present, as can be the case where further processing of fines is less important. Such a configuration is known in the art as a draft-tube crystallizer. A DTB crystallizer can be equipped with an agitator, usually at the bottom of the apparatus in the vicinity of the entry of the feed solution. Like the FC crystallizer, the DTB crystallizer is optionally equipped with an elutriation leg. In some embodiments, an optional external heating loop can be used to increase evaporation rates.

Figure 8:
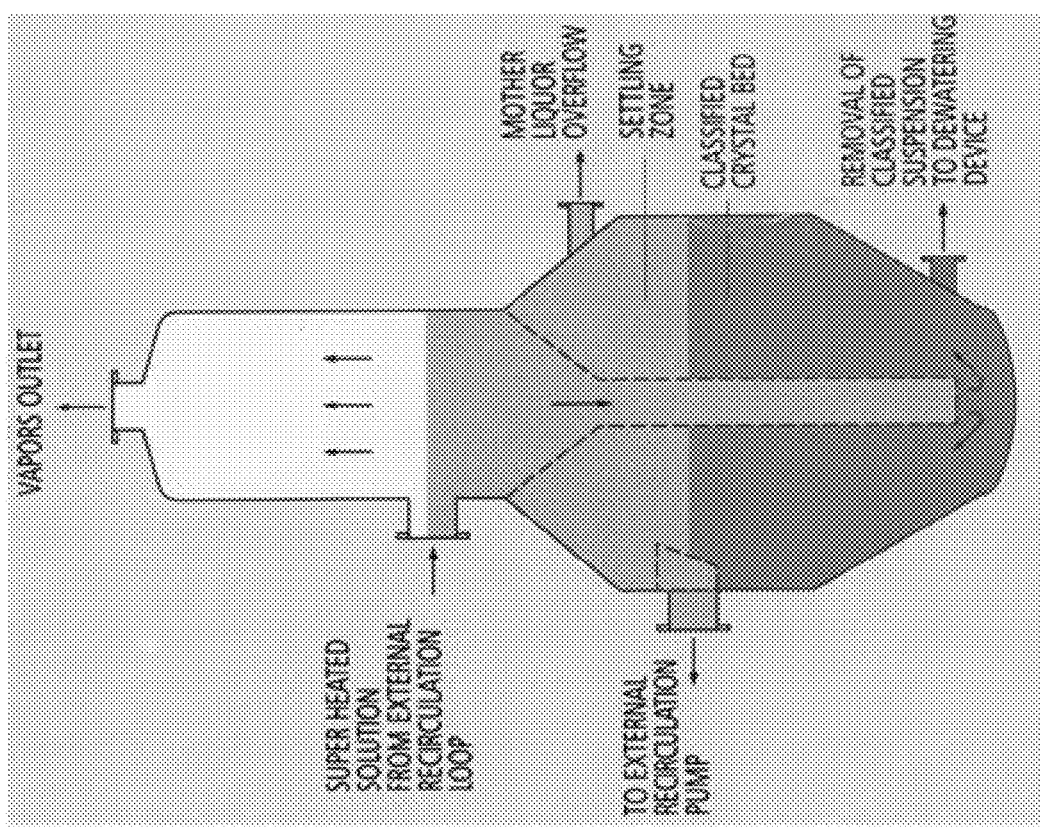
FIG. 8 shows a diagram of a close-type Oslo crystallizer.

Yet another crystallizer configuration is the induced circulation crystallizer as shown in FIG. 8. This configuration provides additional agitation means for the active volume. The apparatus is similar to the DTB crystallizer with respect to the use of a draft tube. Unlike the DTB apparatus, there is no internal agitator. Instead, an inducer in the conical portion of the vessel introduces heated solution from a recirculation pump. As with other crystallization apparatus configurations, the induced circulation crystallizer is optionally equipped with an elutriation leg. Baffles can also be optionally employed with this type of crystallizer.

Figure 9:
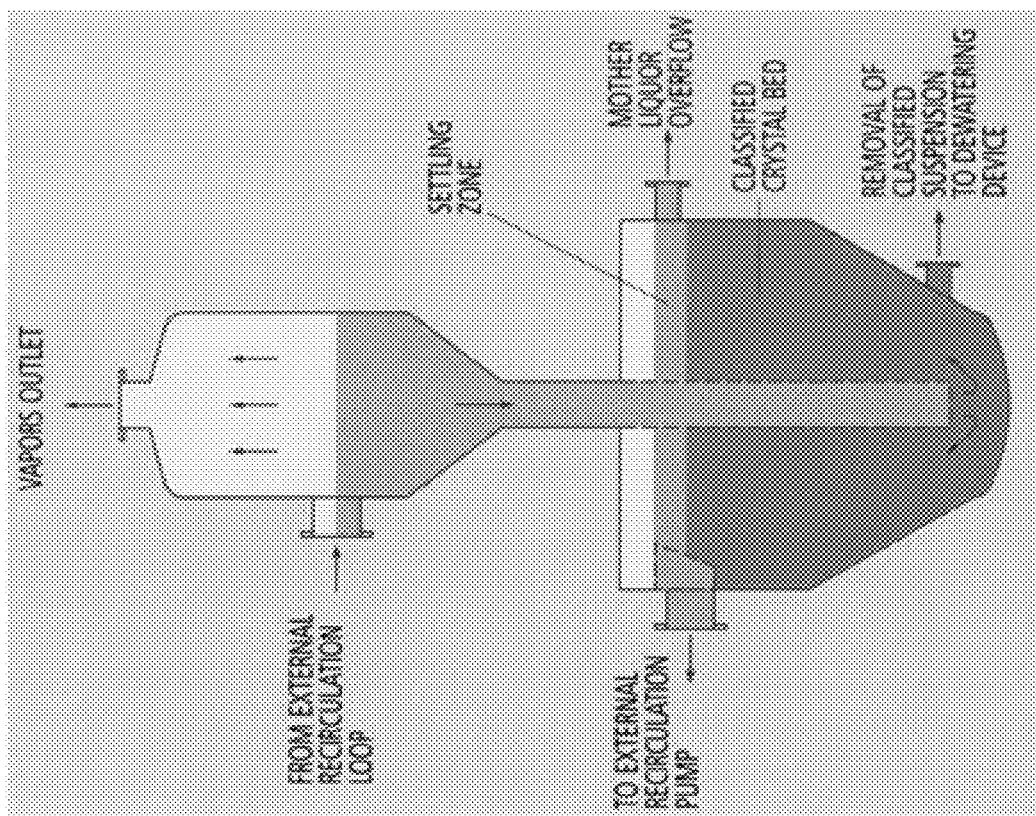
FIG. 9 shows a diagram of an open-type Oslo crystallizer.
Figure 10:
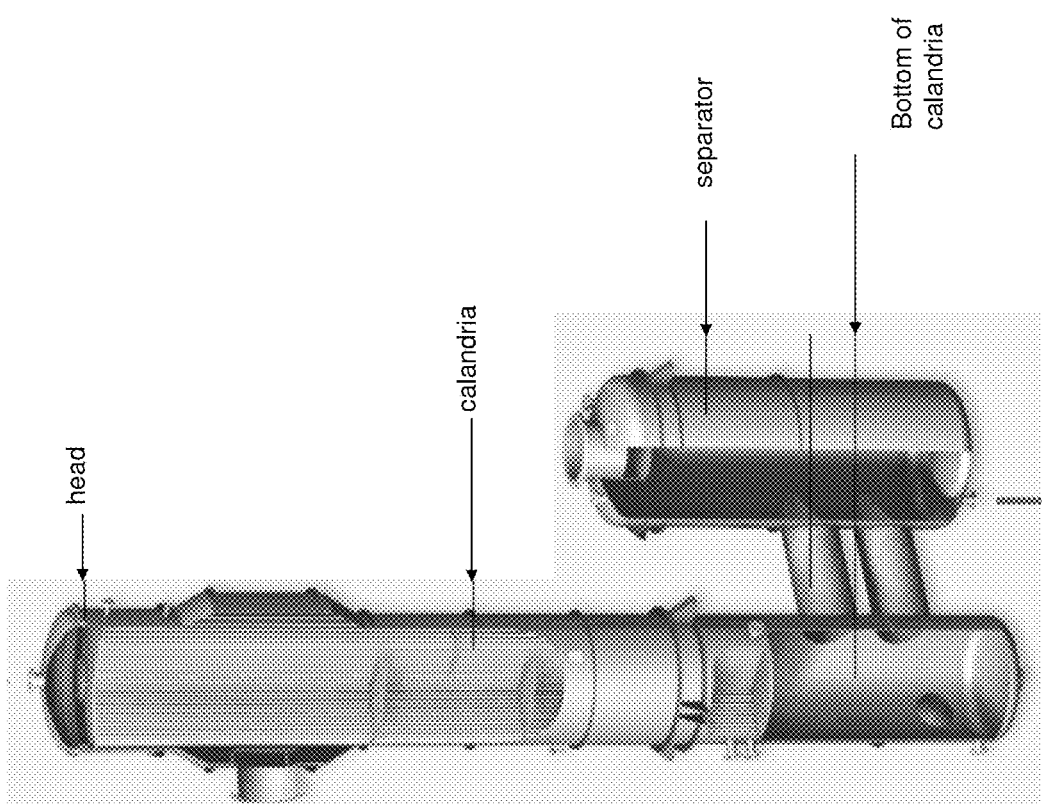
FIG. 10 shows a partial cross-section view of a falling film evaporator.

In still further embodiments, the crystallizer can be an Oslo-type crystallizer, as shown in FIGS. 9 and 10. This type of crystallizer is also referred to as "growth-", "fluid-bed-", or "Krystal-" type crystallizer. The Oslo crystallizer allows the growth of crystals in a fluidized bed, which is not subject to mechanical circulation. A crystal in an Oslo unit will grow to a size proportional to its residence time in the fluid bed. The result is that an Oslo crystallizer can grow crystals larger than most other crystallizer types. The slurry can be removed from the crystallizer's fluidized bed and sent to, for example, a centrifugation section. Clear liquid phase containing 1,4-BDO can be purged from the crystallizer's clarification zone.

The classifying crystallization chamber is the lower part of the unit. The upper part is the liquor-vapor separation area where supersaturation is developed by the removal of water. The slightly supersaturated liquid phase flows down through a central pipe and the supersaturation is relieved by contact with the fluidized bed of crystals. The desupersaturation occurs progressively as the circulating liquid phase moves upwards through the classifying bed before being collected in the top part of the chamber. The remaining liquid leaves via a circulating pipe and after addition of the fresh feed, it passes through the heat exchanger where heat make-up is provided. It is then recycled to the upper part.

In some embodiments, the Oslo type crystallizer can also be optionally equipped with baffles, an elutriation leg, and scrubber as described above. Since the growing crystals are not in contact with any agitation device, the amount of fines to be destroyed is generally lower. The Oslo type crystallizer allows long cycles of production between periods for crystal removal.

The Oslo-type crystallizer is useful for the separation-crystallization of several chemical species as would be found in fermentation media salts. In one embodiment, the Oslo type crystallization unit is of the "closed" type, as shown in FIG. 9. In other embodiments the Oslo-type crystallizer is the "open" type as shown in FIG. 10. The latter configuration is useful when large settling areas are needed, for example.

Many of the foregoing evaporative crystallization apparatus allow for controlled crystal growth. In the recovery of fermentation media salts from the liquid portion after cell removal, the exact crystal morphology, size, and the like are generally inconsequential. Indeed, recovery of amorphous media salts can be sufficient in the purification of any compound of interest, including 1,4-BDO. Thus, in some embodiments, other evaporation methods can be utilized that do not control crystal growth per se.

When salts are removed by nanofiltration and/or ion exchange, a reverse osmosis (RO) membrane filtration can be used to remove a portion of the water prior to evaporation. Water permeates the RO membrane while 1,4-BDO is retained. In some embodiments, an RO membrane can concentrate a product, such as 1,4-BDO to about 20%. One skilled in the art will recognize that the osmotic pressure from the product 1,4-BDO increases to a point where further concentration using an RO membrane is no longer viable. Nonetheless, the use of an RO membrane is a useful low energy input method for concentrating the product of interest prior to the more energy intensive water evaporation process. Thus, on large scale, employing a RO membrane is particularly useful.

In some embodiments, substantially all of the salts are removed prior to removal of water. In other embodiments, substantially all of the salts are removed after removal of a portion of water. The portion of water removed can be any amount including 5%, 10%, 15%, 20%, 25%, 30%, 35%, 40%, 50%, 60%, 70%, 80%, and all values in between. In some embodiments, salts are removed after removal of substantially all of the water. Substantially all the water includes 95%, 96%, 97%, 98%, 99%, 99.9% and all values in between and including all the water.

There are many types and configurations of evaporators available for water removal. One consideration for designing an evaporation system is minimizing energy requirements. Evaporation configurations such as multiple effects or mechanical vapor recompression allow for reduced energy consumption. In some embodiments, removing water is accomplished by evaporation with an evaporator system which includes one or more effects. In some embodiments, a double- or triple-effect evaporator system can be used to separate water from a product of interest, such as 1,4-BDO. Any number of multiple-effect evaporator systems can be used in the removal of water. These apparatus can also be applied to any fermentation product that having a boiling point higher than water. A triple effect evaporator, or other evaporative apparatus configuration, can include dedicated effects that are evaporative crystallizers for salt recovery, for example the final effect of a triple effect configuration.

An evaporator is a heat exchanger in which a liquid is boiled to give a vapor that is also a low pressure steam generator. This steam can be used for further heating in another evaporator called another "effect." Thus, for example, two evaporators can be connected so that the vapor line from one is connected to the steam chest of the other providing a two, or double-effect evaporator. This configuration can be propagated to a third evaporator to create a triple-effect evaporator, for example.

Evaporators can therefore be classified by the number of effects. In a single-effect evaporator, steam provides energy for vaporization and the vapor product is condensed and removed from the system. In a double-effect evaporator, the vapor product off the first effect is used to provide energy for a second vaporization unit. The cascading of effects can continue for any number of stages. Multiple-effect evaporators can remove large amounts of solvent more efficiently relative to a single effect evaporator.

In a multiple effect arrangement, the latent heat of the vapor product off of an effect is used to heat the following effect. Effects are numbered beginning with the one heated by steam, Effect I. The first effect operates under the highest pressure. Vapor from Effect I is used to heat Effect II, which consequently operates at lower pressure. This continues through each addition effect, so that pressure drops through the sequence and the hot vapor will travel from one effect to the next.

In some embodiments, all effects in an evaporator can be physically similar in size, construction, and heat transfer area. Unless thermal losses are significant, they can also have the same capacity as well. Evaporator trains, the serially connected effects, can receive feed in several different ways. Forward Feed arrangements follow the pattern I, II, and III. These use a single feed pump. In this configuration the feed is raised to the highest operating temperature as used in Effect I. The lowest operating temperature is in the final effect, where the product is also most concentrated. Therefore, this configuration is useful for products that are heat sensitive or to reduce side reactions.

In other embodiments, Backward Feed arrangements, III, II, I can be used. In such a configuration multiple pumps are used to work against the pressure drop of the system, however, since the feed is gradually heated they can be more efficient than a forward feed configuration. This arrangement also reduces the viscosity differences through the system and is thus useful for viscous fermentation broths. In some embodiments, Mixed Feed arrangements can be utilized, with the feed entering in the middle of the system, or effects II, III, and I. The final evaporation is performed at the highest temperature. Additionally, fewer pumps are required than in a backward feed arrangement. In still further embodiments, a Parallel Feed system is used to split the feed stream and feed a portion to each effect. This configuration is common in crystallizing evaporators where the product is expected to be a slurry.

Figure 11:
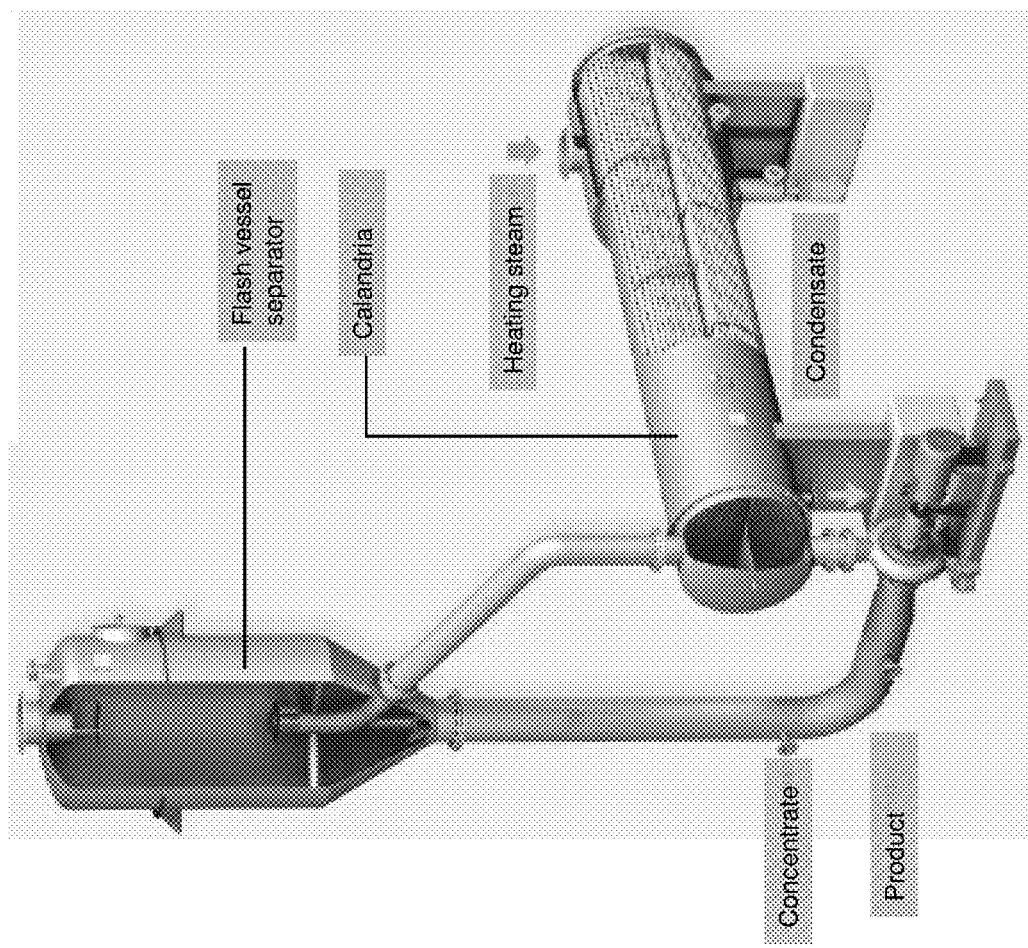
FIG. 11 shows a partial cross-section view of a forced circulation evaporator.

There are numerous evaporator designs. Any combination of designs can be used as an effect as described above. One evaporator design is the falling film evaporator. This apparatus includes a vertical shell-and-tube heat exchanger, with a laterally or concentrically arranged centrifugal separator as shown in FIG. 11.

The liquid to be evaporated is evenly distributed on the inner surface of a tube. The liquid flows downwards forming a thin film, from which evaporation takes place because of the heat applied by the steam. The steam condenses and flows downwards on the outer surface of the tube. A number of tubes are built together side by side. At each end the tubes are fixed to tube plates, and finally the tube bundle is enclosed by a jacket.

The steam is introduced through the jacket. The space between the tubes forms the heating section. The inner side of the tubes is called the boiling section. Together they form the calandria. The concentrated liquid and the vapor leave the calandria at the bottom part, from where the main proportion of the concentrated liquid is discharged. The remaining part enters the subsequent separator tangentially together with the vapor. The separated concentrate is discharged, usually be means of the same pump as for the major part of the concentrate from the calandria, and the vapor leaves the separator from the top. The heating steam, which condenses on the outer surface of the tubes, is collected as condensate at the bottom part of the heating section, from where it is discharged.

Falling film evaporators can be operated with very low temperature differences between the heating media and the boiling liquid, and they also have very short product contact times, typically just a few seconds per pass. These characteristics make the falling film evaporator particularly suitable for heat-sensitive products. Operation of falling film evaporators with small temperature differences facilitates their use in multiple effect configurations or in conjunction with mechanical vapor compression systems.

Sufficient wetting of the heating surface in tubes of the calandria helps avoid dry patches and incrustations which can clog the tubes. In some embodiments, the wetting rate can be increased by extending or dividing the evaporator effects. Falling film evaporators are highly responsive to alterations of parameters such as energy supply, vacuum, feed rate, and concentrations, for example. In some embodiments, a single, double, triple, or other multiple-effect falling film evaporator configuration can utilize fermentation feed that has been filtered through a nanofiltration process as detailed above. Reducing the salts prior to water evaporation can further help prevent incrustation in the tubes of the calandria.

In some embodiments, the falling film evaporator is a short path evaporator. In operation the liquid fraction is evenly distributed over the heating tubes of the calandria by means of a distribution system. The liquid fraction flows down in a thin film on the inside walls in a manner similar to the conventional falling film evaporator. The vapors formed in the in the calandria tubes are condensed as a distillate on external walls of condensate tubes and then flows downward. Water distillate and the enriched liquid fraction are separately discharged from the lower part of the evaporator.

Figure 12:
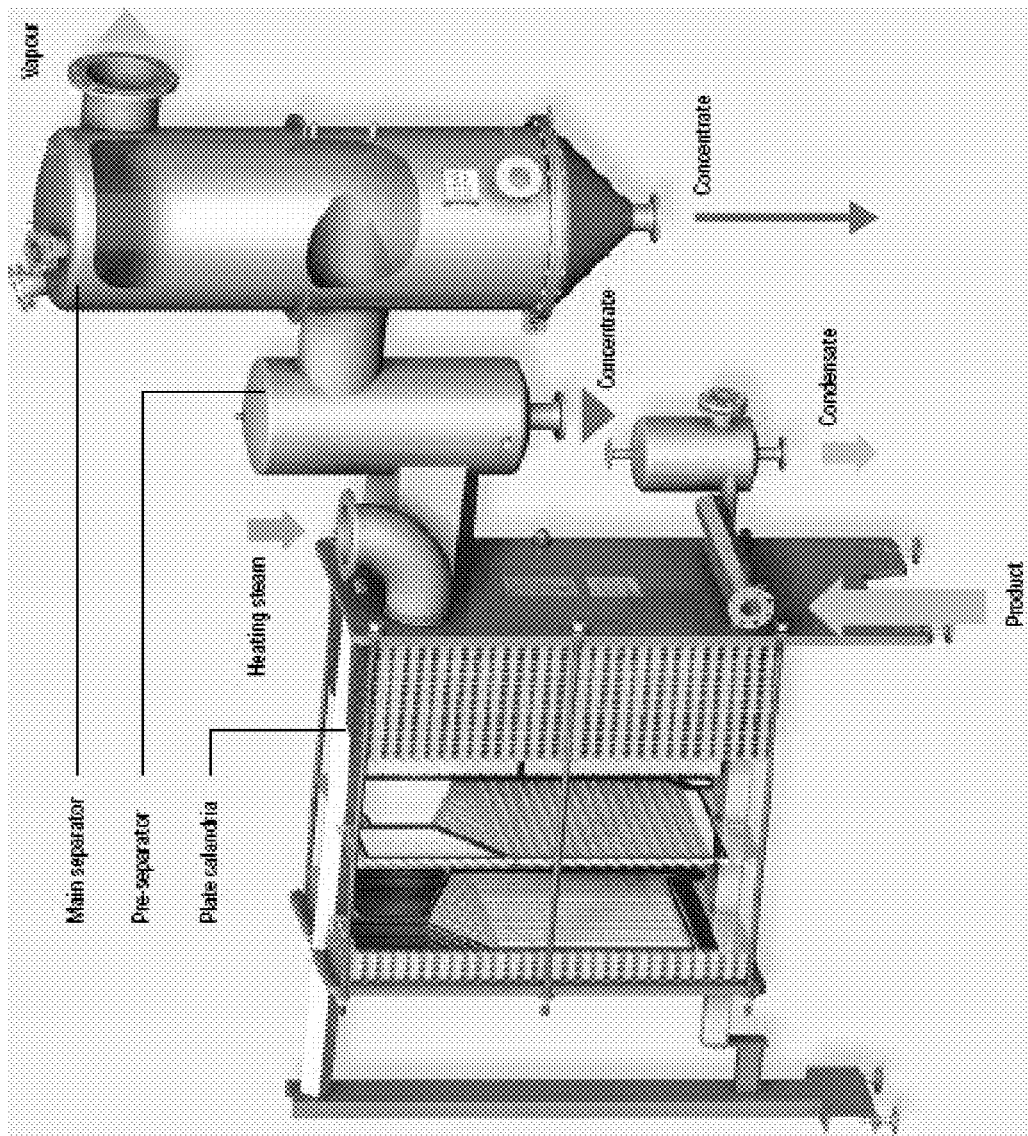
FIG. 12 shows a partial cross-section view of a plate evaporator.

Another evaporator configuration is the forced circulation evaporator. In this design a flash vessel or separator is disposed above a calandria and circulation pump as shown in FIG. 12. In operation, the liquid fraction is circulated through the calandria by means of a circulation pump. The liquid is superheated within the calandria at an elevated pressure higher than the normal boiling pressure. Upon entering the separator, the pressure is rapidly reduced resulting in flashing or rapid boiling of the liquid. The flow velocity, controlled by the circulation pump, and temperatures can be used to control the water removal process. This configuration is useful for avoiding fouling of the calandria tubes.

In some embodiments, multiple forced circulation evaporator effects can be used as described above. For example, in addition to a single effect forced circulation evaporator, double, triple, and multiple effect forced circulation evaporators can be used in the separation of water from the liquid fraction of the fermentation liquid. In some embodiments, one or more forced circulation evaporators can be used in conjunction with one or more falling film evaporators.

Figure 13:
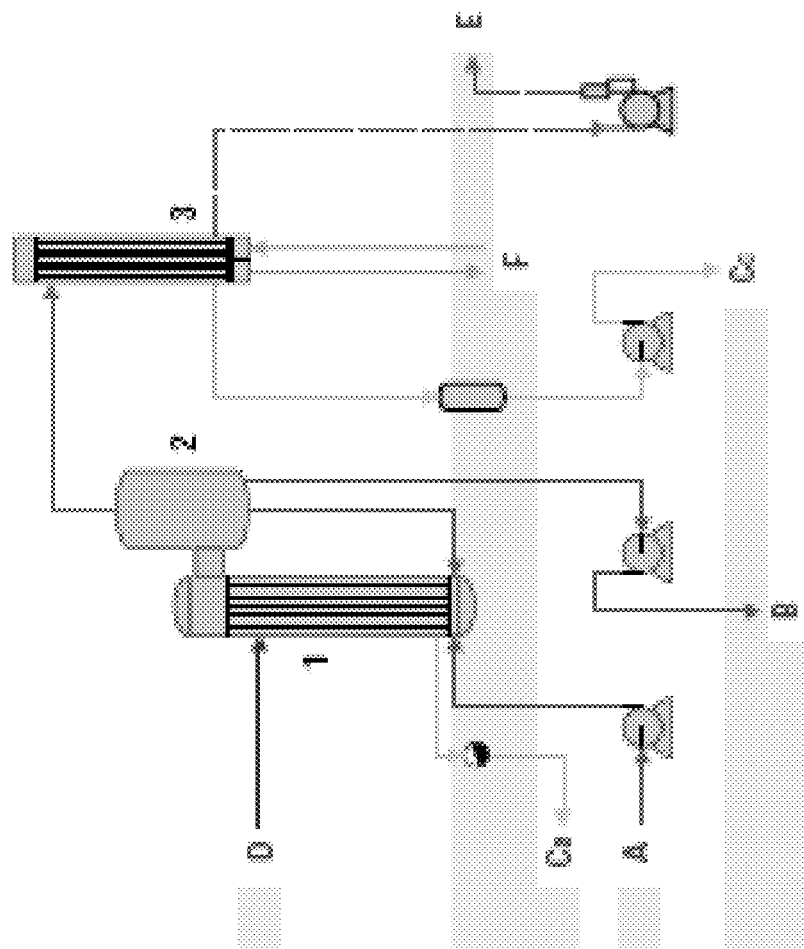
FIG. 13 shows a diagram of a circulation evaporator.

In still further embodiments, the evaporator can be a plate evaporator, as shown in FIG. 13. This evaporator uses a plate heat exchanger and one or more separators. A plate-and-frame configuration uses plates with alternating channels to carry heating media and the liquid fraction of the fermentation broth. In operation, the liquid phase and heating media are passed through their respective channels in counterflow. Defined plate distances and shapes generate turbulence resulting in efficient heat transfer. The heat transfer to the channels with the liquid fraction causes water to boil. The vapor thus formed drives the residual liquid as a rising film into a vapor duct of the plate assembly. Residual liquid and vapors are separated in the downstream centrifugal separator. The wide inlet duct and the upward movement assist in good distribution over the cross-section of the heat exchanger. A plate evaporator can be usefully operated with a pre-filtration through a nanofiltration membrane to avoid fouling. Thus, similar considerations as the falling film evaporator with respect to incrustation are warranted.

In some embodiments, multiple-effect plate evaporation can be utilized in much the same manner as described above for falling film and forced circulation evaporators. When used in multiple effect configurations, one skilled in the art will recognize the benefit of using a forced circulation evaporator and/or a nanofiltration step prior to introduction of the liquid fraction to a plate evaporator. Thus, a separation scheme can include, for example, nanofiltration, followed by a multiple-effect evaporation configuration of one or more forced circulation evaporators, followed by one or more of a plate and/or falling film evaporator. In still further embodiments, any of the evaporative crystallizers described above can also be used in conjunction with a multiple-effect configuration.

Figure 14:
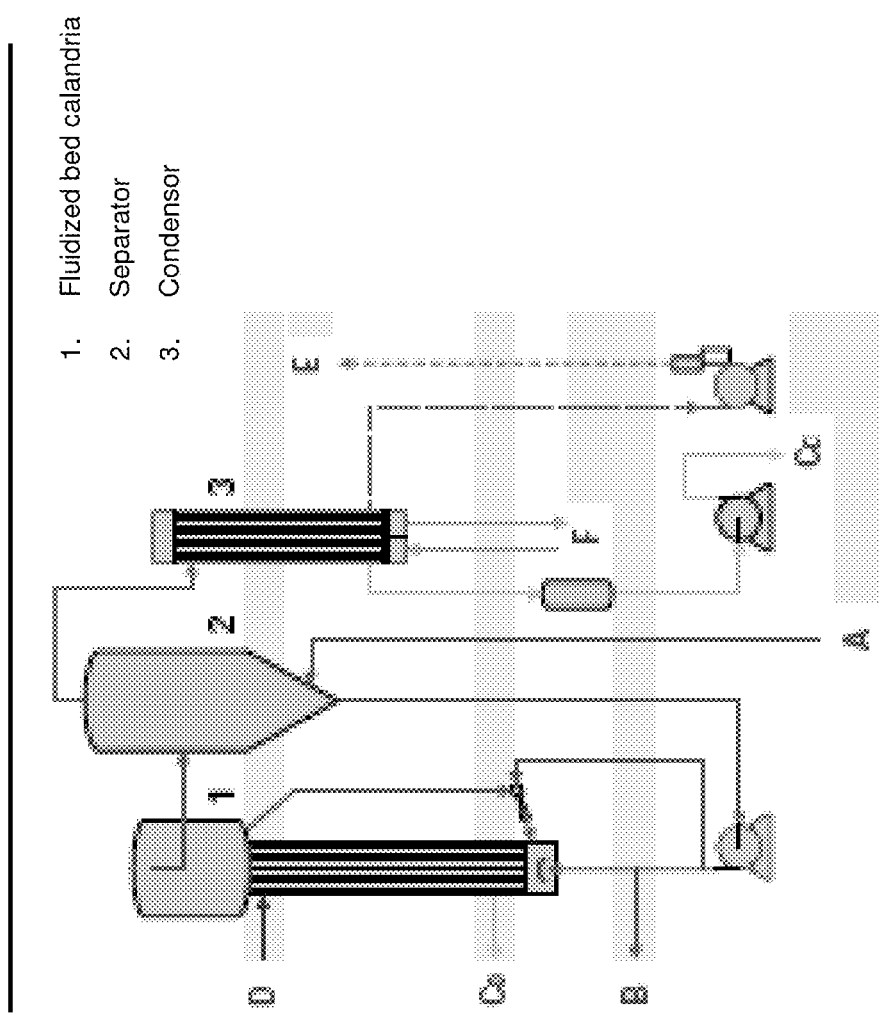
FIG. 14 shows a diagram of a fluidized bed evaporator.

In some embodiments, a circulation evaporator can be used to remove water from the liquid fraction as shown in FIG. 14. The circulation evaporator utilizes a vertical calandria with short tube length with a lateral separator disposed at the top of the heat exchanger. In operation the liquid fraction is supplied at the bottom of the calandria and rises to the top. During heating in the tubes of the calandria, the water begins to boil releasing vapor. The liquid is carried to the top of the calandria entrained by the upward moving vapors. The liquid is separated from the vapors as it enters the separator. The liquid flows back into the evaporator via a circulation pipe to allow continued circulation. The larger the temperature difference between the heating elements of the calandria and the separator chamber results in larger degree of water evaporation from the liquid fraction. When the liquid portion is sufficiently enriched in 1,4-BDO, the salts will begin to precipitate from the liquid fraction.

In some embodiments, the separator of the circulation evaporator can be partitioned into several separation chambers each equipped with its own liquid circulation system. This can reduce the heating surface needed to remove water from the liquid fraction.

Figure 15:
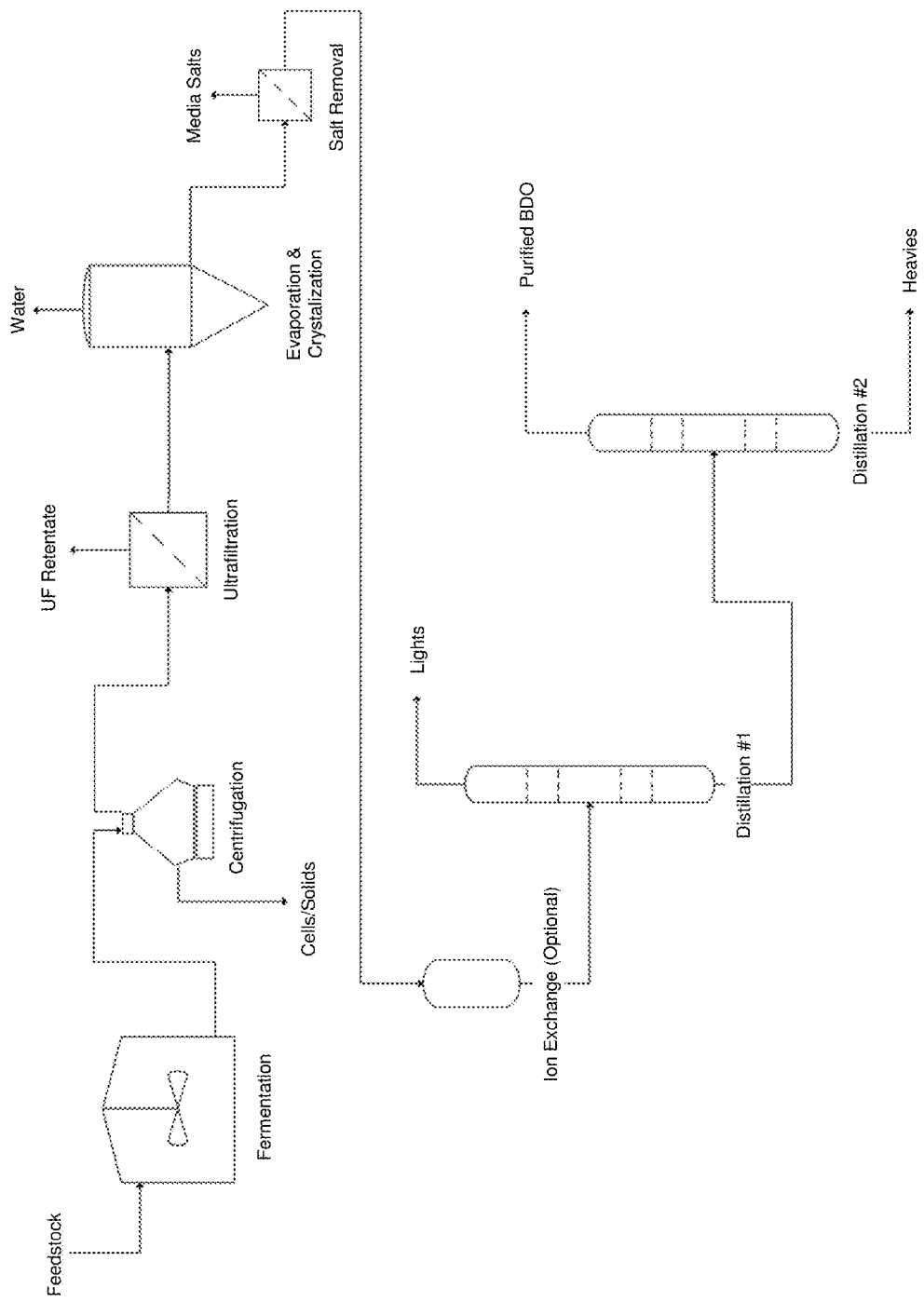
FIG. 15 shows a flow diagram of a complete scheme for the production and isolation of 1,4-BDO.

The fluidized bed evaporator is yet another configuration that can be used for water removal from the liquid fraction. Such a system, shown in FIG. 15, is equipped with a vertical fluidized bed heat exchanger. On the tube side of the heat exchanger are solid particles such as glass or ceramic beads, or steel wire particles.

The fluidized bed evaporator operates in a similar manner to the forced circulation evaporator. The upward movement of the liquid entrains the solid particles which provides a scouring or cleaning action. Together with the liquid fraction they are transferred through the calandria tubes. At the head of the calandria, the solid particles are separated from the liquid and are recycled to the calandria inlet chamber. The superheated fluid is flashed to boiling temperature in the separator allowing removal of water through evaporation. The scouring action of the solids in the tubes of the calandria allow for prolonged operation times and further retard fouling of the tubes. This can be useful when the creation of fouling solids limits the use of conventional forced circulation evaporator systems.

The rising film evaporator is yet another type of evaporator useful in the removal of water from the liquid fraction collected from the fermentation broth. This system configuration has a top-mounted vapor separator on a vertical shell-and-tube heat exchanger (calandria). In operation, the liquid fraction at the bottom of the calandria rises to the top to the vapor separator. External heating causes the water in the liquid fraction to boil in the inside walls of the calandria tubes. The upward movement of the steam causes the liquid fraction to be carried to the top of the calandria. During ascent though the tube further vapor is formed. Upon entry into the separator vapors and liquid phases are separated. The rising film evaporator is particularly useful when used with viscous liquids and/or when large amounts of fouling solids are expected.

The counterflow-trickle evaporator is yet another evaporator that can be used for water removal from the liquid fraction of the fermentation broth. This apparatus has a shell-and-tube heat exchanger (calandria) with the lower part of the calandria larger than that of a rising film evaporator. Disposed on top of the calandria, like the rising film evaporator is a separator. In this evaporator the separator is further equipped with a liquid distribution system.

In operation, liquid is provided at the top of the evaporator like a falling film evaporator. The liquid is distributed over the evaporator tubes, but vapor flows to the top in counterflow to the liquid. In some embodiments, the process can also include a stream of an inert gas, for example, to enhance entrainment. This gas can be introduced in the lower portion of the calandria.

A stirrer evaporator is yet another type of evaporator that can be used for water removal from the liquid fraction of the fermentation broth. This apparatus includes an external, jacket-heated vessel equipped with a stirrer. In operation, the liquid fraction is placed in the vessel, optionally in batches. The water is evaporated off by boiling with continuous stirring to a desired concentration. This apparatus can increase its evaporation rate by increasing the heating surface by use of optional immersion heating coils. This type of evaporator is particularly useful when the fermentation is highly viscous.

Finally, the spiral tube evaporator is another type of evaporator that can be used for water removal from the liquid fraction of the fermentation broth. The design includes a heat exchanger equipped with spiral heating tubes and a bottom-mounted centrifugal separator. In operation, the liquid fraction flows a boiling film from top to bottom in parallel flow to the vapor. The expanding vapors produce a shear, or pushing effect on the liquid film. The curvature of the path of flow induces a secondary flow which interferes with the movement along the tube axis. This turbulence improves heat transfer and is particularly useful with viscous liquids. The spiral configuration of the heating tubes usefully provides a large heating surface area to height ratio relative to a non-spiral, straight tube design. This apparatus provides large evaporation ratios allowing single pass operation.

As described above, the use of multiple evaporators of any type described above in double, triple, and multi-effect configurations can increase the efficiency of evaporation. Other methods to improve efficiency of operation include, for example, thermal and mechanical vapor recompression. In some embodiments, any combination of multiple-effect configurations, thermal recompression, and mechanical recompression can be used to increase evaporation efficiency.

Thermal vapor recompression involves recompressing the vapor from a boiling chamber (or separator) to a higher pressure. The saturated steam temperature corresponding to the heating chamber pressure is higher so that vapor can be reused for heating. This is accomplished with a steam jet vapor recompressor which operates on the steam jet pump principle. Briefly, the steam jet principle utilizes the energy of steam to create vacuum and handle process gases. Steam under pressure enters a nozzle and produces a high velocity jet. This jet action creates a vacuum that draws in and entrains gas. The mixture of steam and gas is discharged at atmospheric pressure. A quantity of steam, called motive steam, is used to operate the thermal recompressor. The motive steam is transferred to the next effect or to a condenser. The energy of the excess vapor is approximately that of the motive steam quantity used.

In multiple-effect evaporators equipped with thermal vapor recompressors, the heating medium in the first calandria is the product vapor from one of the associated effects, compressed to a higher temperature level by means of a steam ejector. The heating medium in any subsequent effect is the vapor generated in the previous calandria. Vapor from the final effect is condensed with incoming product, optionally supplemented by cooling water as necessary. All recovered water is readily recycled to a fermentation broth.

Mechanical recompressors utilize all vapor leaving one evaporator. The vapor is recompressed to the pressure of the corresponding heating steam temperature of the evaporator. The operating principle is similar to a heat pump. The energy of the vapor condensate can be optionally used to pre-heat further portions of the liquid fraction of the fermentation broth. The mechanical recompression is supplied by use of a high pressure fans or turbocompressors. These fans operate a high velocity and are suited for large flow rates at vapor compression ratios of about 1:1.2 to about 1:2. Rational speeds can be between about 3,000 to about 18,000 rpm. In some embodiments, when particularly high pressures are useful, multiple stage compressors can be used.

In evaporators with equipped with mechanical vapor recompressors, the heating medium in the first effect is vapor developed in the same effect, compressed to a higher temperature by means of a high-pressure fan. Any excess vapor from the high heat section is optionally condensed or can be utilized in a high concentrator.

As described above there are many possible evaporation types that can be arranged in various energy efficient configurations including multiple effect, thermal vapor recompression, mechanical vapor recompression, or combinations of these. Optimal configurations depend on many factors, including, for example, whether media salts are removed prior to evaporation or via crystallization during the evaporation. For the case where salts are removed prior to evaporation, low cost configurations are useful. Exemplary configurations include a falling film triple effect evaporator system or mechanical vapor recompression system. The case where salts are crystallized during the evaporation is more complex due to the possibility of scaling of the heat exchanger surfaces by precipitation of the salts. An exemplary configuration for this case includes triple effect where the first two effects are falling film evaporators (before the onset of crystallization) and the final stage is a forced circulation evaporative crystallizer, for example.

1,4-BDO purification, in particular, can occur in a series of two distillation columns, although more can be used. A first column is used to separate water and other light components from 1,4-BDO, while a second column is used to distill the 1,4-BDO from any residual heavy components. The distillation columns can be operated under vacuum to reduce the required temperatures and reduce unwanted reactions, product degradation, and color formation. Pressure drop across the columns can be minimized to maintain low temperatures in the bottom reboiler. Residence time in the reboiler can be minimized to also prevent unwanted reactions, product degradation, and color formation, by using, for example, a falling film reboiler.

Those skilled in the art will recognize that various configurations of the enumerated centrifugation, filtration, ion exchange, evaporator crystallizer, evaporator, and distillation apparatus are useful in the purification of a compound of interest, including 1,4-BDO. One exemplary configuration includes, for example, disc stack centrifugation, ultrafiltration, evaporative crystallization, ion exchange, and distillation as shown in the flow scheme diagram of FIG. 16. Thus, in some embodiments, the present invention provides a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by evaporative crystallization, removing a further portion of salts from the liquid fraction by ion exchange, and distilling 1,4-BDO.

Figure 16:
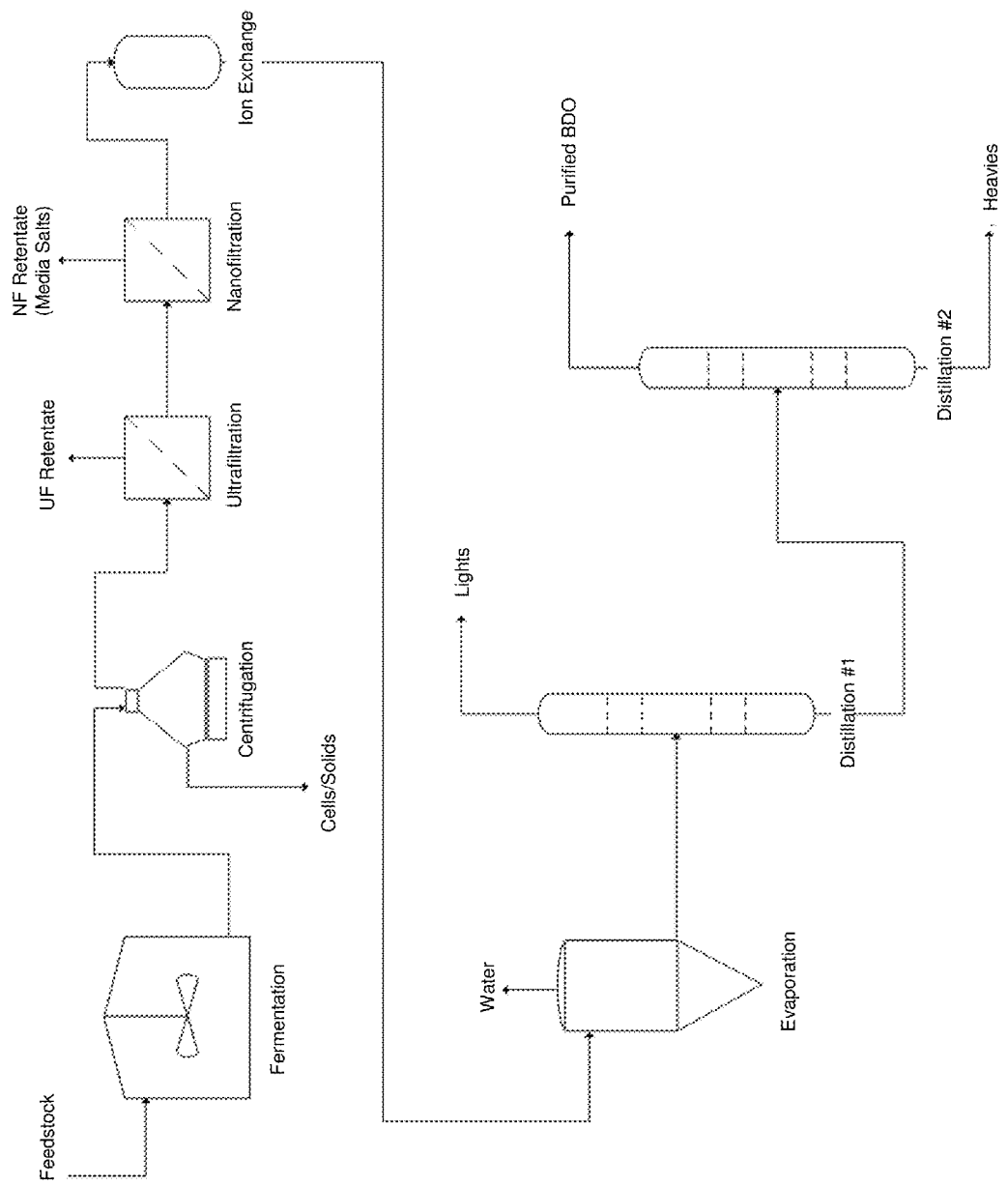
FIG. 16 shows a flow diagram of another complete scheme for the production and isolation of 1,4-BDO.

As shown in FIG. 16, cells and solids are first removed by disc stack centrifugation. The cells can be optionally recycled back into fermentation. Ultrafiltration removes cell debris, DNA, and precipitated proteins. Evaporative crystallization removes a portion of the media salts and water, either of which can be optionally recycled back into fermentation. Following evaporative crystallization, the remaining liquid phase is passed through an ion exchange column to remove further salts. After ion exchange, a portion of the water can be evaporated in an evaporator system, as described above. Distillation of the light fraction, is followed by distillation of 1,4-BDO to provide substantially pure 1,4-BDO.

Another exemplary configuration includes disc stack centrifugation, ultrafiltration, nanofiltration, ion exchange, evaporation, and distillation as shown in FIG. 17. Thus, in some embodiments, the present invention provides a process of isolating 1,4-BDO from a fermentation broth that includes removing a portion of solids by disc stack centrifugation to provide a liquid fraction, removing a further portion of solids from the liquid fraction by ultrafiltration, removing a portion of salts from the liquid fraction by nanofiltration, removing a further portion of salts from the liquid fraction by ion exchange, evaporating a portion of water, and distilling 1,4-BDO.

As shown in FIG. 17, cells and solids are first removed by disc stack centrifugation. The cells can be optionally recycled back into fermentation. Ultrafiltration removes cell debris, DNA, and precipitated proteins. Nanofiltration removes a portion of the media salts, which can be optionally recycled back into fermentation. Following nanofiltration, the permeate is passed through an ion exchange column to remove further salts. After ion exchange, a portion of the water can be evaporated in an evaporator system, as described above. Distillation of the light fraction, is followed by distillation of 1,4-BDO to provide substantially pure 1,4-BDO.

The compound of interest can be any compound for which the product can be engineered for biosynthesis in a microorganism. The processes disclosed herein are applicable to compounds of interest that have boiling points higher than water. Specifically, compounds of interest can have a boiling point between about 120° C. and 400° C. Other properties include high solubility or miscibility in water and the inability to appreciably solubilize salts (when employing evaporative crystallization), and neutral compounds with molecular weights below about 100-150 Daltons (for suitability with nanofiltration).

The processes and principles described herein can be applied to isolate a compound of interest from a fermentation broth, where the compound of interest has the general properties described above. Such a process includes separating a liquid fraction enriched in the compound of interest from a solid fraction that includes the cell mass, followed by water and salt removal, followed by purification.

In some embodiments, the invention also provides a process for recycling components of a fermentation broth. The fermentation broth can include 1,4-BDO or any compound of interest having a boiling point higher than water, cells capable of producing 1,4-BDO or the compound of interest, media salts, and water. The process includes separating a liquid fraction enriched in 1,4-BDO or the compound of interest from a solid fraction that includes the cells. The cells are then recycled into the fermentation broth. Water can be removed before or after separation of salts from the liquid fraction. Evaporated water from the liquid fraction is recycled into the fermentation broth. Salts from the liquid fraction can be removed and recycled into the fermentation broth either by removal of water from the liquid fraction, causing the salts to crystallize, or by nanofiltration and/or ion exchange. The separated salts from nanofiltration are then recycled into the fermentation broth. The process provides 1,4-BDO or other compounds of interest which can be further purified by, for example, by distillation.

In some embodiments, a process for producing a compound of interest, such as 1,4-BDO, includes culturing a compound-producing microorganism in a fermentor for a sufficient period of time to produce the compound of interest. The organism includes a microorganism having a compound pathway comprising one or more exogenous genes encoding a compound pathway enzyme and/or one or more gene disruptions. The process for producing the compound also includes isolating the compound by a process that includes separating a liquid fraction enriched in compound of interest from a solid fraction comprising cells, removing water from the liquid fraction, removing salts from the liquid fraction, and purifying the compound of interest. The compound of interest has a boiling point higher than water.

In a specific embodiment, a process for producing 1,4-BDO includes culturing a 1,4-BDO-producing microorganism in a fermentor for a sufficient period of time to produce 1,4-BDO. The organism includes a microorganism having a 1,4-BDO pathway including one or more exogenous genes encoding a compound pathway enzyme and/or one or more gene disruptions. The process for producing 1,4-BDO also includes isolating the compound by a process that includes separating a liquid fraction enriched in compound of interest from a solid fraction comprising cells, removing water from the liquid fraction, removing salts from the liquid fraction, and purifying the compound of interest.

In particular embodiments where the product of interest is 1,4-BDO, production begins with the culturing of a microbial organism capable of producing 1,4-BDO via a set of 1,4-BDO pathway enzymes. Exemplary microbial organisms include, without limitation, those described in U.S. 2009/0075351 and U.S. 2009/0047719, both of which are incorporated herein by reference in their entirety.

Organisms can be provided that incorporate one or more exogenous nucleic acids that encode enzymes in a 1,4-BDO pathway. Such organisms include, for example, non-naturally occurring microbial organisms engineered to have a complete 1,4-BDO biosynthetic pathway. Such pathways can include enzymes encoded by both endogenous and exogenous nucleic acids. Enzymes not normally present in a microbial host can add in functionality to complete a pathways by including one or more exogenous nucleic acids, for example. One such 1,4-BDO pathway includes enyzmes encoding a 4-hydroxybutanoate dehydrogenase, a succinyl-CoA synthetase, a CoA-dependent succinic semialdehyde dehydrogenase, a 4-hydroxybutyrate:CoA transferase, a 4-butyrate kinase, a phosphotransbutyrylase, an α-ketoglutarate decarboxylase, an aldehyde dehydrogenase, an alcohol dehydrogenase or an aldehyde/alcohol dehydrogenase.

Another pathway can include one or more exogenous nucleic acids encoding a 4-aminobutyrate CoA transferase, a 4-aminobutyryl-CoA hydrolase, a 4-aminobutyrate-CoA ligase, a 4-aminobutyryl-CoA oxidoreductase (deaminating), a 4-aminobutyryl-CoA transaminase, or a 4-hydroxybutyryl-CoA dehydrogenase. Such a pathway can further include a 4-hydroxybutyryl-CoA reductase (alcohol forming), a 4-hydroxybutyryl-CoA reductase, or 1,4-butanediol dehydrogenase Still another pathway can include one or more exogenous nucleic acids encoding a 4-aminobutyrate CoA transferase, a 4-aminobutyryl-CoA hydrolase, a 4-aminobutyrate-CoA ligase, a 4-aminobutyryl-CoA reductase (alcohol forming), a 4-aminobutyryl-CoA reductase, a 4-aminobutan-1-ol dehydrogenase, a 4-aminobutan-1-ol oxidoreductase (deaminating) or a 4-aminobutan-1-ol transaminase. Such a pathway can further include a 1,4-butanediol dehydrogenase.

A further pathway can include one ore more exogenous nucleic acids encoding a 4-aminobutyrate kinase, a 4-aminobutyraldehyde dehydrogenase (phosphorylating), a 4-aminobutan-1-ol dehydrogenase, a 4-aminobutan-1-ol oxidoreductase (deaminating), a 4-aminobutan-1-ol transaminase, a [(4-aminobutanolyl)oxy]phosphonic acid oxidoreductase (deaminating), a [(4-aminobutanolyl)oxy] phosphonic acid transaminase, a 4-hydroxybutyryl-phosphate dehydrogenase, or a 4-hydroxybutyraldehyde dehydrogenase (phosphorylating). Such a pathway can further include a 1,4-butanediol dehydrogenase.

Yet a further pathway can include one or more exogenous nucleic acids encoding an alpha-ketoglutarate 5-kinase, a 2,5-dioxopentanoic semialdehyde dehydrogenase (phosphorylating), a 2,5-dioxopentanoic acid reductase, an alpha-ketoglutarate CoA transferase, an alpha-ketoglutaryl-CoA hydrolase, an alpha-ketoglutaryl-CoA ligase, an alpha-ketoglutaryl-CoA reductase, a 5-hydroxy-2-oxopentanoic acid dehydrogenase, an alpha-ketoglutaryl-CoA reductase (alcohol forming), a 5-hydroxy-2-oxopentanoic acid decarboxylase, or a 5-hydroxy-2-oxopentanoic acid dehydrogenase (decarboxylation). Such a pathway can further include a 4-hydroxybutyryl-CoA reductase (alcohol forming), a 4-hydroxybutyryl-CoA reductase, or a 1,4-butanediol dehydrogenase.

Yet a further pathway can include one or more exogenous nucleic acids encoding a glutamate CoA transferase, a glutamyl-CoA hydrolase, a glutamyl-CoA ligase, a glutamate 5-kinase, a glutamate-5-semialdehyde dehydrogenase (phosphorylating), a glutamyl-CoA reductase, a glutamate-5-semialdehyde reductase, a glutamyl-CoA reductase (alcohol forming), a 2-amino-5-hydroxypentanoic acid oxidoreductase (deaminating), a 2-amino-5-hydroxypentanoic acid transaminase, a 5-hydroxy-2-oxopentanoic acid decarboxylase, or a 5-hydroxy-2-oxopentanoic acid dehydrogenase (decarboxylation). Such a pathway can further include a 4-hydroxybutyryl-CoA reductase (alcohol forming), a 4-hydroxybutyryl-CoA reductase, or a 1,4-butanediol dehydrogenase.

Yet a further pathway can include one or more exogenous nucleic acids encoding a 3-hydroxybutyryl-CoA dehydrogenase, a 3-hydroxybutyryl-CoA dehydratase, a vinylacetyl-CoA Δ-isomerase, or a 4-hydroxybutyryl-CoA dehydratase. Such a pathway can further include a 4-hydroxybutyryl-CoA reductase (alcohol forming), a 4-hydroxybutyryl-CoA reductase, or a 1,4-butanediol dehydrogenase.

Yet a further pathway can include one ore more exogenous nucleic acids encoding a homoserine deaminase, a homoserine CoA transferase, a homoserine-CoA hydrolase, a homoserine-CoA ligase, a homoserine-CoA deaminase, a 4-hydroxybut-2-enoyl-CoA transferase, a 4-hydroxybut-2-enoyl-CoA hydrolase, a 4-hydroxybut-2-enoyl-CoA ligase, a 4-hydroxybut-2-enoate reductase, a 4-hydroxybutyryl-CoA transferase, a 4-hydroxybutyryl-CoA hydrolase, a 4-hydroxybutyryl-CoA ligase, or a 4-hydroxybut-2-enoyl-CoA reductase. Such a pathway can further include a 4-hydroxybutyryl-CoA reductase (alcohol forming), a 4-hydroxybutyryl-CoA reductase, or a 1,4-butanediol dehydrogenase.

Yet a further pathway can include one or more exogenous nucleic acids encoding a succinyl-CoA reductase (alcohol forming), a 4-hydroxybutyryl-CoA hydrolase, a 4-hydroxybutyryl-CoA ligase, or a 4-hydroxybutanal dehydrogenase (phosphorylating). Such a pathway can further include a succinyl-CoA reductase, a 4-hydroxybutyrate dehydrogenase, a 4-hydroxybutyryl-CoA transferase, a 4-hydroxybutyrate kinase, a phosphotrans-4-hydroxybutyrylase, a 4-hydroxybutyryl-CoA reductase, a 4-hydroxybutyryl-CoA reductase (alcohol forming), or a 1,4-butanediol dehydrogenase.

Yet a further pathway can include one or more exogenous nucleic acid encoding a glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, or 4-hydroxybutanal dehydrogenase (phosphorylating). Such a pathway can further include an alpha-ketoglutarate decarboxylase, a 4-hydroxybutyrate dehydrogenase, a 4-hydroxybutyryl-CoA transferase, a 4-hydroxybutyrate kinase, a phosphotrans-4-hydroxybutyrylase, a 4-hydroxybutyryl-CoA reductase, a 4-hydroxybutyryl-CoA reductase (alcohol forming), or a 1,4-butanediol dehydrogenase.

In addition to, or in lieu of, gene insertions, an organism can include gene disruptions to direct the carbon flux toward the direction of synthesizing 1,4-BDO. Such organisms include for example, non-naturally occurring microorganism having a set of metabolic modifications that couple 1,4-butanediol production to growth. In some embodiments, 1,4-butanediol production is not coupled to growth. The set of metabolic modifications can include disruption of one or more genes, or an ortholog thereof. Disruption can include complete gene deletion in some embodiments. Disruption can also include modification via removal of a promoter sequence and the like. For 1,4-BDO production a set of metabolic modifications can include disruption of adhE and ldhA, for example. Other disruption can include the gene mdh. Still other disruptions can include one or more genes selected from the set of genes including mqo, aspA, sfcA, maeB, pntAB, and gdhA. Still other disruptions can include one or more genes selected from the set of genes including pykA, pykF, dhaKLM, deoC, edd, yiaE, ycdW, prpC, and gsk. Still other disruptions can include disruption of pflAB. An exemplary set of disruptions can include one or more genes selected from the set of genes comprising adhE, ldhA, pflAB, mdh, and aspA, including disruption of each of the genes adhE, ldhA, pflAB, mdh, and aspA.

Further exemplary sets of disruptions include adher, nadh6; adher, ppck; adher, sucd4; adher, atps4r; adher, fum; adher, mdh; adher, pfli, ppck; adher, pfli, sucd4; adher, ackr, nadh6; adher, nadh6, pfli; adher, aspt, mdh; adher, nadh6, ppck; adher, ppck, thd2; adher, atps4r, ppck; adher, mdh, thd2; adher, fum, pfli; adher, ppck, sucd4; adher, glcpts, ppck; adher, gludy, mdh; adher, gludy, ppck; adher, fum, ppck; adher, mdh, ppck; adher, fum, gludy; adher, fum, hex1; adher, hex1, pfli; adher, hex1, thd2; adher, frd2, ldh_d, mdh; adher, frd2, ldh_d, me2; adher, mdh, pgl, thd2; adher, g6pdhy, mdh, thd2; adher, pfli, ppck, thd2; adher, ackr, akgd, atps4r; adher, glcpts, pfli, ppck; adher, ackr, atps4r, sucoas; adher, gludy, pfli, ppck; adher, me2, pfli, sucd4; adher, gludy, pfli, sucd4; adher, atps4r, ldh_d, sucd4; adher, fum, hex1, pfli; adher, mdh, nadh6, thd2; adher, atps4r, mdh, nadh6; adher, atps4r, fum, nadh6; adher, aspt, mdh, nadh6; adher, aspt, mdh, thd2; adher, atps4r, glcpts, sucd4; adher, atps4r, gludy, mdh; adher, atps4r, mdh, ppck; adher, atps4r, fum, ppck; adher, aspt, glcpts, mdh; adher, aspt, gludy, mdh; adher, me2, sucd4, thd2; adher, fum, ppck, thd2; adher, mdh, ppck, thd2; adher, gludy, mdh, thd2; adher, hex1, pfli, thd2; adher, atps4r, g6pdhy, mdh; adher, atps4r, mdh, pgl; adher, ackr, frd2, ldh_d; adher, ackr, ldh_d, sucd4; adher, atps4r, fum, gludy; adher, atps4r, fum, hex1; adher, atps4r, mdh, thd2; adher, atps4r, frd2, ldh_d; adher, atps4r, mdh, pgdh; adher, glcpts, ppck, thd2; adher, gludy, ppck, thd2; adher, fum, hex1, thd2; adher, atps4r, me2, thd2; adher, fum, me2, thd2; adher, glcpts, gludy, ppck; adher, me2, pgl, thd2; adher, g6pdhy, me2, thd2; adher, atps4r, frd2, ldh_d, me2; adher, atps4r, frd2, ldh_d, mdh; adher, aspt, ldh_d, mdh, pfli; adher, atps4r, glcpts, nadh6, pfli; adher, atps4r, mdh, nadh6, pgl; adher, atps4r, g6pdhy, mdh, nadh6; adher, ackr, fum, gludy, ldh_d; adher, ackr, gludy, ldh_d, sucd4; adher, atps4r, g6pdhy, mdh, thd2; adher, atps4r, mdh, pgl, thd2; adher, aspt, g6pdhy, mdh, pyk; adher, aspt, mdh, pgl, pyk; adher, aspt, ldh_d, mdh, sucoas; adher, aspt, fum, ldh_d, mdh; adher, aspt, ldh_d, mals, mdh; adher, aspt, icl, ldh_d, mdh; adher, frd2, gludy, ldh_d, ppck; adher, frd2, ldh_d, ppck, thd2; adher, ackr, atps4r, ldh_d, sucd4; adher, ackr, acs, ppc, ppck; adher, gludy, ldh_d, ppc, ppck; adher, ldh_d, ppc, ppck, thd2; adher, aspt, atps4r, glcpts, mdh; adher, g6pdhy, mdh, nadh6, thd2; adher, mdh, nadh6, pgl, thd2; adher, atps4r, g6pdhy, glcpts, mdh; adher, atps4r, glcpts, mdh, pgl; and adher, ackr, ldh_d, mdh, sucd4. The aforementioned genes are included in a broader list of knockout candidates, along with the reactions that these genes catalyze, in Table 1a below.

TABLE 1a

Gene Knockout Candidates in E. coli.

| Reaction Abbreviation | Reaction Stoichiometry* | Genes Encoding the Enzyme(s) Catalyzing Each Reaction& |
|---|---|---|
| ACKr | [c]: ac + atp <==> actp + adp | (b3115 or b2296 or b1849) |
| ACS | [c]: ac + atp + coa --> accoa + amp + ppi | b4069 |
| ACt6 | ac[p] + h[p] <==> ac[c] + h[c] | Non-gene associated |
| ADHEr | [c]: etoh + nad <==> acald + h + nadh | (b0356 or b1478 or b1241) |
|  | [c]: acald + coa + nad <==> accoa + h + nadh | (b1241 or b0351) |
| AKGD | [c]: akg + coa + nad --> co2 + nadh + succoa | (b0116 and b0726 and b0727) |
| ASNS2 | [c]: asp-L + atp + nh4 --> amp + asn-L + h + ppi | b3744 |
| ASPT | [c]: asp-L --> fum + nh4 | b4139 |

TABLE 1a-continued

Gene Knockout Candidates in *E. coli*.

| Reaction Abbreviation | Reaction Stoichiometry* | Genes Encoding the Enzyme(s) Catalyzing Each Reaction& |
|---|---|---|
| ATPS4r | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | [c]: atp + co2 + nh4 <==> adp + cbp + (2) h | (b0521 or b0323 or b2874) |
| EDA | [c]: 2ddg6p --> g3p + pyr | b1850 |
| ENO | [c]: 2pg <==> h2o + pep | b2779 |
| FBA | [c]: fdp <==> dhap + g3p | (b2097 or b2925 or b1773) |
| FBP | [c]: fdp + h2o --> f6p + pi | (b4232 or b3925) |
| FDH2 | for[p] + (2) h[c] + q8[c] --> co2[c] + h[p] + q8h2[c]<br>for[p] + (2) h[c] + mqn8[c] --> co2[c] + h[p] + mql8[c] | ((b3892 and b3893 and b3894) or (b1474 and b1475 and b1476)) |
| FRD2 | [c]: fum + mql8 --> mqn8 + succ<br>[c]: 2dmmql8 + fum --> 2dmmq8 + succ | (b4151 and b4152 and b4153 and b4154) |
| FTHFD | [c]: 10fthf + h2o --> for + h + thf | b1232 |
| FUM | [c]: fum + h2o <==> mal-L | (b1612 or b4122 or b1611) |
| G5SD | [c]: glu5p + h + nadph --> glu5sa + nadp + pi | b0243 |
| G6PDHy | [c]: g6p + nadp <==> 6pgl + h + nadph | b1852 |
| GLCpts | glc-D[p] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | [c]: atp + glu-L --> adp + glu5p | b0242 |
| GLUDy | [c]: glu-L + h2o + nadp <==> akg + h + nadph + nh4 | b1761 |
| GLYCL | [c]: gly + nad + thf --> co2 + mlthf + nadh + nh4 | (b2904 and b2903 and b2905 and b0116) |
| HEX1 | [c]: atp + glc-D --> adp + g6p + h | b2388 |
| ICL | [c]: icit --> glx + succ | b4015 |
| LDH_D | [c]: lac-D + nad <==> h + nadh + pyr | (b2133 or b1380) |
| MALS | [c]: accoa + glx + h2o --> coa + h + mal-L | (b4014 or b2976) |
| MDH | [c]: mal-L + nad <==> h + nadh + oaa | b3236 |
| ME2 | [c]: mal-L + nadp --> co2 + nadph + pyr | b2463 |
| MTHFC | [c]: h2o + methf <==> 10fthf + h | b0529 |
| NADH12 | [c]: h + mqn8 + nadh --> mql8 + nad<br>[c]: h + nadh + q8 --> nad + q8h2<br>[c]: 2dmmq8 + h + nadh --> 2dmmql8 + nad | b1109 |
| NADH6 | (4) h[c] + nadh[c] + q8[c] --> (3) h[p] + nad[c] + q8h2[c]<br>(4) h[c] + mqn8[c] + nadh[c] --> (3) h[p] + mql8[c] + nad[c]<br>2dmmq8[c] + (4) h[c] + nadh[c] --> 2dmmql8[c] + (3) h[p] + nad[c] | (b2276 and b2277 and b2278 and b2279 and b2280 and b2281 and b2282 and b2283 and b2284 and b2285 and b2286 and b2287 and b2288) |
| PFK | [c]: atp + f6p --> adp + fdp + h | (b3916 or b1723) |
| PFLi | [c]: coa + pyr --> accoa + for | (((b0902 and b0903) and b2579) or (b0902 and b0903) or (b0902 and b3114) or (b3951 and b3952)) |
| PGDH | [c]: 6pgc + nadp --> co2 + nadph + ru5p-D | b2029 |
| PGI | [c]: g6p <==> f6p | b4025 |
| PGL | [c]: 6pgl + h2o --> 6pgc + h | b0767 |
| PGM | [c]: 2pg <==> 3pg | (b3612 or b4395 or b0755) |
| PPC | [c]: co2 + h2o + pep --> h + oaa + pi | b3956 |
| PPCK | [c]: atp + oaa --> adp + co2 + pep | b3403 |
| PRO1z | [c]: fad + pro-L --> 1pyr5c + fadh2 + h | b1014 |
| PYK | [c]: adp + h + pep --> atp + pyr | b1854 or b1676) |
| PYRt2 | h[p] + pyr[p] <==> h[c] + pyr[c] | Non-gene associated |
| RPE | [c]: ru5p-D <==> xu5p-D | (b4301 or b3386) |
| SO4t2 | so4[e] <==> so4[p] | (b0241 or b0929 or b1377 or b2215) |
| SUCD4 | [c]: q8 + succ --> fum + q8h2 | (b0721 and b0722 and b0723 and b0724) |
| SUCOAS | [c]: atp + coa + succ <==> adp + pi + succoa | (b0728 and b0729) |
| SULabc | atp[c] + h2o[c] + so4[p] --> adp[c] + h[c] + pi[c] + so4[c] | ((b2422 and b2425 and b2424 and b2423) or (b0763 and b0764 and b0765) or (b2422 and b2424 and b2423 and b3917)) |
| TAL | [c]: g3p + s7p <==> e4p + f6p | (b2464 or b0008) |
| THD2 | (2) h[p] + nadh[c] + nadp[c] --> (2) h[c] + nad[c] + nadph[c] | (b1602 and b1603) |
| THD5 | [c]: nad + nadph --> nadh + nadp | (b3962 or (b1602 and b1603)) |
| TPI | [c]: dhap <==> g3p | b3919 |

The abbreviations for the metabolites in Table 1a are shown below in Table 1b.

TABLE 1b

Metabolite names corresponding to abbreviations used in Table 1a.

| Metabolite Abbreviation | Metabolite Name |
|---|---|
| 10fthf | 10-Formyltetrahydrofolate |
| 1pyr5c | 1-Pyrroline-5-carboxylate |
| 2ddg6p | 2-Dehydro-3-deoxy-D-gluconate 6-phosphate |
| 2dmmq8 | 2-Demethylmenaquinone 8 |
| 2dmmql8 | 2-Demethylmenaquinol 8 |
| 2pg | D-Glycerate 2-phosphate |
| 3pg | 3-Phospho-D-glycerate |
| 6pgc | 6-Phospho-D-gluconate |
| 6pgl | 6-phospho-D-glucono-1,5-lactone |
| ac | Acetate |
| acald | Acetaldehyde |
| accoa | Acetyl-CoA |
| actp | Acetyl phosphate |
| adp | ADP |
| akg | 2-Oxoglutarate |
| amp | AMP |
| asn-L | L-Asparagine |
| asp-L | L-Aspartate |
| atp | ATP |
| cbp | Carbamoyl phosphate |
| co2 | CO2 |
| coa | Coenzyme A |
| dhap | Dihydroxyacetone phosphate |
| e4p | D-Erythrose 4-phosphate |
| etoh | Ethanol |
| f6p | D-Fructose 6-phosphate |
| fad | Flavin adenine dinucleotide oxidized |
| fadh2 | Flavin adenine dinucleotide reduced |
| fdp | D-Fructose 1,6-bisphosphate |
| for | Formate |
| fum | Fumarate |
| g3p | Glyceraldehyde 3-phosphate |
| g6p | D-Glucose 6-phosphate |
| glc-D | D-Glucose |
| glu5p | L-Glutamate 5-phosphate |
| glu5sa | L-Glutamate 5-semialdehyde |
| glu-L | L-Glutamate |
| glx | Glyoxylate |
| gly | Glycine |
| h | H+ |
| h2o | H2O |
| icit | Isocitrate |
| lac-D | D-Lactate |
| mal-L | L-Malate |
| methf | 5,10-Methenyltetrahydrofolate |

TABLE 1b-continued

Metabolite names corresponding to abbreviations used in Table 1a.

| Metabolite Abbreviation | Metabolite Name |
|---|---|
| mlthf | 5,10-Methylenetetrahydrofolate |
| mql8 | Menaquinol 8 |
| mqn8 | Menaquinone 8 |
| nad | Nicotinamide adenine dinucleotide |
| nadh | Nicotinamide adenine dinucleotide - reduced |
| nadp | Nicotinamide adenine dinucleotide phosphate |
| nadph | Nicotinamide adenine dinucleotide phosphate - reduced |
| nh4 | Ammonium |
| oaa | Oxaloacetate |
| pep | Phosphoenolpyruvate |
| pi | Phosphate |
| ppi | Diphosphate |
| pro-L | L-Proline |
| pyr | Pyruvate |
| q8 | Ubiquinone-8 |
| q8h2 | Ubiquinol-8 |
| ru5p-D | D-Ribulose 5-phosphate |
| s7p | Sedoheptulose 7-phosphate |
| so4 | Sulfate |
| succ | Succinate |
| succoa | Succinyl-CoA |
| thf | 5,6,7,8-Tetrahydrofolate |
| xu5p-D | D-Xylulose 5-phosphate |

Any non-naturally occurring microorganism incorporating any combination of the above gene disruptions can also include a gene insertion of at least one exogenous nucleic acid. Any of the gene insertion pathways described above can be integrated with gene disruptions. For example, a pathway including disruptions of the genes adhE, ldhA, pflAB, mdh, and aspA can also include insertion of a 4-hydroxybutanoate dehydrogenase, a CoA-independent succinic semialdehyde dehydrogenase, a succinyl-CoA synthetase, a CoA-dependent succinic semialdehyde dehydrogenase, a 4-hydroxybutyrate:CoA transferase, a glutamate:succinic semialdehyde transaminase, a glutamate decarboxylase, a CoA-independent aldehyde dehydrogenase, a CoA-dependent aldehyde dehydrogenase or an alcohol dehydrogenase. Table 2 below summarizes exemplary engineered organisms for the production of 1,4-BDO that incorporate combinations of gene disruption and gene insertion. Note that gene insertion can be in the form of chromosomal insertion or providing a plasmid.

TABLE 2

Combination Disruption-Insertion Designs for 1,4-BDO Production

| Strain # | Host chromosome | Host Description | Plasmid-based |
|---|---|---|---|
| 1 | ΔldhA | Single deletion derivative of E. coli MG1655 | E. coli sucCD, P. gingivalis sucD, P. gingivalis 4hbd, P. gingivalis Cat2, C. acetobutylicum AdhE2 |
| 2 | ΔadhE ΔldhA ΔpflB | Succinate producing strain; derivative of E. coli MG1655 | E. coli sucCD, P. gingivalis sucD, P. gingivalis 4hbd, P. gingivalis Cat2, C. acetobutylicum AdhE2 |
| 3 | ΔadhE ΔldhA ΔpflB ΔlpdA::K.p.lpdA322 | Improvement of lpdA to increase pyruvate dehydrogenase flux | E. coli sucCD, P. gingivalis sucD, P. gingivalis 4hbd, P. gingivalis Cat2, C. acetobutylicum AdhE2 |
| 4 | ΔadhE ΔldhA ΔpflB ΔlpdA::K.p.lpdA322 | | E. coli sucCD, P. gingivalis sucD, P. gingivalis 4hbd, C. acetobutylicum buk1, C. acetobutylicum ptb, C. acetobutylicum AdhE2 |
| 5 | ΔadhE ΔldhA ΔpflB ΔlpdA::K.p.lpdA322 Δmdh ΔarcA | Deletions in mdh and arcA to direct flux through oxidative TCA cycle | E. coli sucCD, P. gingivalis sucD, P. gingivalis 4hbd, P. gingivalis Cat2, C. acetobutylicum AdhE2 |

TABLE 2-continued

Combination Disruption-Insertion Designs for 1,4-BDO Production

| Strain # | Host chromosome | Host Description | Plasmid-based |
|---|---|---|---|
| 6 | ΔadhE ΔldhA ΔpflB ΔlpdA::K.p.lpdA322 Δmdh ΔarcA | | *M. bovis* sucA, *E. coli* sucCD, *P. gingivalis* sucD, *P. gingivalis* 4hbd, *P. gingivalis* Cat2, *C. acetobutylicum* AdhE2 |
| 7 | ΔadhE ΔldhA ΔpflB ΔlpdA::K.p.lpdA322 Δmdh ΔarcA gltAR163L | Mutation in citrate synthase to improve anaerobic activity | *E. coli* sucCD, *P. gingivalis* sucD, *P. gingivalis* 4hbd, *P. gingivalis* Cat2, *C. acetobutylicum* AdhE2 |
| 8 | ΔadhE ΔldhA ΔpflB ΔlpdA::K.p.lpdA322 Δmdh ΔarcA gltAR163L | | *M. bovis* sucA, *E. coli* sucCD, *P. gingivalis* sucD, *P. gingivalis* 4hbd, *P. gingivalis* Cat2, *C. acetobutylicum* AdhE2 |
| 9 | ΔadhE ΔldhA ΔpflB ΔlpdA::K.p.lpdA322 Δmdh ΔarcA gltAR163L | | *M. bovis* sucA, *E. coli* sucCD, *P. gingivalis* sucD, *P. gingivalis* 4hbd, *P. gingivalis* Cat2, *C. beijerinckii* Ald |
| 10 | ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd | Succinate branch of upstream pathway integrated into ECKh-422 | *P. gingivalis* Cat2, *C. beijerinckii* Ald |
| 11 | ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd | Succinate and alpha-ketoglutarate upstream pathway branches integrated into ECKh-422 | *P. gingivalis* Cat2, *C. beijerinckii* Ald |
| 12 | ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd | | *C. acetobutylicum* buk1, *C. acetobutylicum* ptb, *C. beijerinckii* Ald |
| 13 | ΔadhE ΔldhA ΔpflB ΔlpdA::K.p.lpdA322 Δmdh ΔarcA gltAR163L ΔackA fimD:: *E. coli* sucCD, *P. gingivalis* sucD, *P. gingivalis* 4hbd fimD:: *M. bovis* sucA, *C. kluyveri* 4hbd | Acetate kinase deletion of ECKh-432 | *P. gingivalis* Cat2, *C. beijerinckii* Ald |
| 14 | ΔadhE ΔldhA ΔpflB ΔlpdA::K.p.lpdA322 Δmdh ΔarcA gltAR163L ΔackA Δppc::H.i.ppck fimD:: *E. coli* sucCD, *P. gingivalis* sucD, *P. gingivalis* 4hbd fimD:: *M. bovis* sucA, *C. kluyveri* 4hbd | Acetate kinase deletion and PPC/PEPCK replacement of ECKh-432 | *P. gingivalis* Cat2, *C. beijerinckii* Ald |
| 15 | ΔadhE ΔldhA ΔpflB ΔlpdA::fnr-pflB6-K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd | Replacement of lpdA promoter with anaerobic promoter in ECKh-432 | *P. gingivalis* Cat2, *C. beijerinckii* Ald |
| 16 | ΔadhE ΔldhA ΔpflB ΔlpdA:: K.p.lpdA322 ΔpdhR:: fnr-pflB6 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd | Replacement of pdhR and aceEF promoter with anaerobic promoter in ECKh-432 | *P. gingivalis* Cat2, *C. beijerinckii* Ald |
| 17 | ΔadhE ΔldhA ΔpflB ΔlpdA:: K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd fimD:: *C. acetobutylicum* buk1, *C. acetobutylicum* ptb | Integration of BK/PTB into ECKh-432 | *C. beijerinckii* Ald |
| 18 | ΔadhE ΔldhA ΔpflB ΔlpdA:: K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd fimD:: *C. acetobutylicum* buk1, *C. acetobutylicum* ptb | | *C. beijerinckii* Ald, *G. thermoglucosidasius* adh1 |
| 19 | ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd rrnC::cscAKB | Non-PTS sucrose genes inserted into ECKh-432 | *P. gingivalis* Cat2, *C. beijerinckii* Ald |
| 20 | ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd rrnC::cscAKB | | *C. acetobutylicum* buk1, *C. acetobutylicum* ptb, *C. beijerinckii* Ald |

*The delta symbol (Δ) indicates gene deletion.

The strains summarized in Table 2 are as follows: Strain 1: Single deletion derivative of *E. coli* MG1655, with deletion of endogenous ldhA; plasmid expression of *E. coli* sucCD, *P. gingivalis* sucD, *P. gingivalis* 4hbd, *P. gingivalis* Cat2, *C. acetobutylicum* AdhE2. Strain 2: Host strain AB3, a succinate producing strain, derivative of *E. coli* MG1655, with deletions of endogenous adhE ldhA pflB; plasmid expression of *E. coli* sucCD, *P. gingivalis* sucD, *P. gingivalis* 4hbd, *P. gingivalis* Cat2, *C. acetobutylicum* AdhE2.

Strain 3: Host strain ECKh-138, deletion of endogenous adhE, ldhA, pflB, deletion of endogenous lpdA and chromosomal insertion of *Klebsiella pneumoniae* lpdA with a Glu354Lys mutation at the lpdA locus; plasmid expression of *E. coli* sucCD, *P. gingivalis* sucD, *P. gingivalis* 4hbd, *P. gingivalis* Cat2, *C. acetobutylicum* AdhE2; strain provides improvement of lpdA to increase pyruvate dehydrogenase flux. Strain 4: Host strain ECKh-138, deletion of endogenous adhE, ldhA, pflB, and lpdA, chromosomal insertion of *Klebsiella pneumoniae* lpdA with a Glu354Lys mutation; plasmid expression *E. coli* sucCD, *P. gingivalis* sucD, *P. gingivalis* 4hbd, *C. acetobutylicum* buk1, *C. acetobutylicum* ptb, *C. acetobutylicum* AdhE2.

Strain 5: Host strain ECKh-401, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA; plasmid expression of *E. coli* sucCD, *P. gingivalis* sucD, *P. gingivalis* 4hbd, *P. gingivalis* Cat2, *C. acetobutylicum* AdhE2; strain has deletions in mdh and arcA to direct flux through oxidative TCA cycle. Strain 6: host strain ECKh-401, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA; plasmid expression of *M. bovis* sucA, *E. coli* sucCD, *P. gingivalis* sucD, *P. gingivalis* 4hbd, *P. gingivalis* Cat2, *C. acetobutylicum* AdhE2.

Strain 7: Host strain ECKh-422, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant; plasmid expression of *E. coli* sucCD, *P. gingivalis* sucD, *P. gingivalis* 4hbd, *P. gingivalis* Cat2, *C. acetobutylicum* AdhE2; strain has mutation in citrate synthase to improve anaerobic activity. Strain 8: strain ECKh-422, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant; plasmid expression of *M. bovis* sucA, *E. coli* sucCD, *P. gingivalis* sucD, *P. gingivalis* 4hbd, *P. gingivalis* Cat2, *C. acetobutylicum* AdhE2. Strain 9: host strain ECKh-422, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant; plasmid expression of *M. bovis* sucA, *E. coli* sucCD, *P. gingivalis* sucD, *P. gingivalis* 4hbd, *P. gingivalis* Cat2, *C. beijerinckii* Ald.

Strain 10: host strain ECKh-426, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd; plasmid expression of *P. gingivalis* Cat2, *C. beijerinckii* Ald; strain has succinate branch of upstream pathway integrated into strain ECKh-422 at the fimD locus. Strain 11: host strain ECKh-432, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has succinate and alpha-ketoglutarate upstream pathway branches integrated into ECKh-422. Strain 12: host strain ECKh-432, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *C. acetobutylicum* buk1, *C. acetobutylicum* ptb, *C. beijerinckii* Ald.

Strain 13: host strain ECKh-439, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, deletion of endogenous ackA, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion in strain ECKh-432. Strain 14: host strain ECKh-453, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, deletion of endogenous ackA, deletion of endogenous ppc and insertion of *Haemophilus influenza* ppck at the ppc locus, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion and PPC/PEPCK replacement in strain ECKh-432.

Strain 15: host strain ECKh-456, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, replacement of lpdA promoter with fnr binding site, pflB-p6 promoter and RBS of pflB; plasmid expression of *P. gingivalis* Cat2, *C. beijerinckii* Ald; strain has replacement of lpdA promoter with anaerobic promoter in strain ECKh-432. Strain 16: host strain ECKh-455, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbdl, replacement of pdhR and aceEF promoter with fnr binding site, pflB-p6 promoter and RBS of pflB; plasmid expression of *P. gingivalis* Cat2, *C. beijerinckii* Ald; strain has replacement of pdhR and aceEF promoter with anaerobic promoter in ECKh-432.

Strain 17: host strain ECKh-459, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald; strain has integration of BK/PTB into strain ECKh-432. Strain 18: host strain ECKh-459, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald, *G. thermoglucosidasius* adhI.

Strain 19: host strain ECKh-463, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon genes sucrose permease (cscB), D-fructokinase (cscK), sucrose hydrolase (cscA), and a LacI-related sucrose-specific repressor (cscR); plasmid expression of *P. gingivalis* Cat2, *C. beijerinckii* Ald; strain has non-PTS sucrose genes inserted into strain ECKh-432. Strain 20: host strain ECKh-463 deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon; plasmid expression of *C. acetobutylicum* buk1, *C. acetobutylicum* ptb, *C. beijerinckii* Ald.

Strains engineered for the utilization of sucrose via a phosphotransferase (PTS) system produce significant amounts of pyruvate as a byproduct. Therefore, the use of a non-PTS sucrose system can be used to decrease pyruvate formation because the import of sucrose would not be accompanied by the conversion of phosphoenolpyruvate (PEP) to pyruvate. This will increase the PEP pool and the flux to oxaloacetate through PPC or PEPCK.

Insertion of a non-PTS sucrose operon into the rrnC region can be performed. To generate a PCR product containing the non-PTS sucrose genes flanked by regions of homology to the rrnC region, two oligos are used to PCR amplify the csc genes from Mach1™ (Invitrogen, Carlsbad, Calif.). This strain is a descendent of W strain which is an *E. coli* strain known to be able to catabolize sucrose (Orencio-Trejo et al., *Biotechnology Biofuels* 1:8 (2008)). The sequence was derived from *E. coli* W strain KO11 (accession AY314757) (Shukla et al., *Biotechnol. Lett.* 26:689-693 (2004)) and includes genes encoding a sucrose permease (cscB), D-fructokinase (cscK), sucrose hydrolase (cscA), and a LacI-related sucrose-specific repressor (cscR). The first 53 amino acids of cscR was effectively removed by the placement of the primer. After purification, the PCR product is electroporated into MG1655 electrocompetent cells which had been transformed with pRedET (tet) and prepared according to the manufacturer's instructions (www.genebridges.com/gb/pdf/K001%20Q%20E%20 BAC%20Modification%20Kit-version2.6-2007-screen.pdf). The PCR product is designed so that it integrates into the genome into the rrnC region of the chromosome. It effectively deletes 191 nucleotides upstream of rrlC (23S rRNA), all of the rrlC rRNA gene and 3 nucleotides downstream of rrlC and replaces it with the sucrose operon. The entire rrnC::crcAKB region is transferred into the BDO host strain ECKh-432 by P1 transduction (Sambrook et al., *Molecular Cloning: A Laboratory Manual*, Third Ed., Cold Spring Harbor Laboratory, New York (2001), resulting in ECKh-463 (ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd rrnC::cscAKB). Recombinants are selected by growth on sucrose and verified by diagnostic PCR.

Prior to culturing the compound-producing or 1,4-BDO-producing organisms, the raw materials feedstock such as sucrose syrup and media components can be treated, for example, by heat sterilization prior to addition to the production bioreactor to eliminate any biological contaminants. In accordance with some embodiments, the feedstock can include, for example, sucrose or glucose for the fermentation of BDO. In some embodiments, the feedstock can include syngas. Additional media components used to support growth of the microorganisms include, for example, salts, nitrogen sources, buffers, trace metals, and a base for pH control. The major components of an exemplary media package, expressed in g/L of fermentation broth, are shown below in Table 3.

TABLE 3

| Category | Concentration |
| --- | --- |
| N-Source | 3 g/L |
| Buffer | 5 g/L |
| Salts | 0.65 g/L |
| Base | 1.4 g/L |
| | 10.1 g/L |

The type of carbon source can vary considerably and can include glucose, fructose, lactose, sucrose, maltodextrins, starch, inulin, glycerol, vegetable oils such as soybean oil, hydrocarbons, alcohols such as methanol and ethanol, organic acids such as acetate, syngas, and similar combinations of CO, $CO_2$, and $H_2$. The term "glucose" includes glucose syrups, i.e. glucose compositions comprising glucose oligomers. Plant and plant-derived biomass material can be a source of low cost feedstock. Such feedstock can include, for example, corn, soybeans, cotton, flaxseed, rapeseed, sugar cane and palm oil. Biomass can undergo enzyme or chemical mediated hydrolysis to liberate substrates which can be further processed via biocatalysis to produce chemical products of interest. These substrates include mixtures of carbohydrates, as well as aromatic compounds and other products that are collectively derived from the cellulosic, hemicellulosic, and lignin portions of the biomass. The carbohydrates generated from the biomass are a rich mixture of 5 and 6 carbon sugars that include, for example, sucrose, glucose, xylose, arabinose, galactose, mannose, and fructose.

The carbon source can be added to the culture as a solid, liquid, or gas. The carbon source can be added in a controlled manner to avoid stress on the cells due to overfeeding. In this respect, fed-batch and continuous culturing are useful culturing modes as further discussed below.

The type of nitrogen source can vary considerably and can include urea, ammonium hydroxide, ammonium salts, such as ammonium sulphate, ammonium phosphate, ammonium chloride and ammonium nitrate, other nitrates, amino acids such as glutamate and lysine, yeast extract, yeast autolysates, yeast nitrogen base, protein hydrolysates (including, but not limited to, peptones, casein hydrolysates such as tryptone and casamino acids), soybean meal, Hy-Soy, tryptic soy broth, cotton seed meal, malt extract, corn steep liquor and molasses.

The pH of the culture can be controlled by the addition of acid or alkali. Because pH can drop during culture, alkali can be added as necessary. Examples of suitable alkalis include NaOH and $NH_4OH$.

Exemplary cell growth procedures used in the production of a compound of interest, such as 1,4-BDO, include, batch fermentation, fed-batch fermentation with batch separation; fed-batch fermentation with continuous separation, and continuous fermentation with continuous separation. All of these processes are well known in the art. Depending on the organism design, the fermentations can be carried out under aerobic or anaerobic conditions. In some embodiments, the temperature of the cultures kept between about 30 and about 45° C., including 31, 32, 33, 34, 35, 36, 37, 38, 39, 40, 41, 42, 43, and 44° C.

In batch fermentation, a tank fermenter (or bioreactor) is filled with the prepared media to support growth. The temperature and pH for microbial fermentation is properly adjusted, and any additional supplements are added. An inoculum of a 1,4-BDO-producing organism is added to the fermenter. In batch fermentation the fermentation will generally run for a fixed period and then the products from the fermentation are isolated. The process can be repeated in batch runs.

In fed-batch fermentation fresh media is continuously or periodically added to the fermentation bioreactor. Fixed-volume fed-batch fermentation is a type of fed-batch fermentation in which a carbon source is fed without diluting the culture. The culture volume can also be maintained nearly constant by feeding the growth carbon source as a concentrated liquid or gas. In another type of fixed-volume fed-batch culture, sometimes called a cyclic fed-batch culture, a portion of the culture is periodically withdrawn and used as the starting point for a further fed-batch process. Once the fermentation reaches a certain stage, the culture is removed and the biomass is diluted to the original volume with sterile water or medium containing the carbon feed substrate. The dilution decreases the biomass concentration and results in an increase in the specific growth rate. Subsequently, as feeding continues, the growth rate will decline gradually as biomass increases and approaches the maximum sustainable in the vessel once more, at which point the culture can be diluted again. Alternatively, a fed-batch fermentation can be variable volume. In variable-volume mode the volume of the fermentation broth changes with the fermentation time as nutrient and media are continually added to the culture without removal of a portion of the fermentation broth.

In a continuous fermentation, fresh media is generally continually added with continuous separation of spent medium, which can include the product of interest, such as 1,4-BDO, when the product is secreted. One feature of the continuous culture is that a time-independent steady-state can be obtained which enables one to determine the relations between microbial behavior and the environmental conditions. Achieving this steady-state is accomplished by means of a chemostat, or similar bioreactor. A chemostat allows for the continual addition of fresh medium while culture liquid is continuously removed to keep the culture volume constant. By altering the rate at which medium is added to the chemostat, the growth rate of the microorganism can be controlled.

The continuous and/or near-continuous production of a compound of interesting, such as 1,4-BDO can include culturing a compound-producing organism in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms that produce a compound of interest can be cultured for hours, if suitable for a particular application. It is to be understood that the continuous and/or near-continuous culture conditions also can include all time intervals in between these exemplary periods. It is further understood that the time of culturing the compound-producing microbial organism is for a sufficient period of time to produce a sufficient amount of product for a desired purpose.

In some embodiments, the culture can be conducted under aerobic conditions. An oxygen feed to the culture can be controlled. Oxygen can be supplied as air, enriched oxygen, pure oxygen or any combination thereof. Methods of monitoring oxygen concentration are known in the art. Oxygen can be delivered at a certain feed rate or can be delivered on demand by measuring the dissolved oxygen content of the culture and feeding accordingly with the intention of maintaining a constant dissolved oxygen content. In other embodiments, the culture can be conducted under substantially anaerobic conditions. Substantially anaerobic means that the amount of oxygen is less than about 10% of saturation for dissolved oxygen in liquid media. Anaerobic conditions include sealed chambers of liquid or solid medium maintained with an atmosphere of less than about 1% oxygen.

Fermentations can be performed under anaerobic conditions. For example, the culture can be rendered substantially free of oxygen by first sparging the medium with nitrogen and then sealing culture vessel (e.g., flasks can be sealed with a septum and crimp-cap). Microaerobic conditions also can be utilized by providing a small hole for limited aeration. On a commercial scale, microaerobic conditions are achieved by sparging a fermentor with air or oxygen as in the aerobic case, but at a much lower rate and with tightly controlled agitation.

In some embodiments, the compound of interest, including 1,4-BDO, can be produced in an anaerobic batch fermentation using genetically modified E. Coli. In fermentation, a portion of the feedstock substrate is used for cell growth and additional substrate is converted to other fermentation byproducts. Media components such as salts, buffer, nitrogen, etc can be added in excess to the fermentation to support cell growth. The fermentation broth is thus a complex mixture of water, the compound of interest, byproducts, residual media, residual substrate, and feedstock/media impurities. It is from this fermentation broth that the compound of interest is isolated and purified. An exemplary fermentation broth composition is shown below in Table 4.

TABLE 4*

| Quantity | Component |
|---|---|
| ~100 g/L | 1,4-BDO |
| ~5 g/L | cell mass |
| ~10 g/L | byproducts (ethanol, acetic acid, 4-hydroxybutyric acid, GBL, proteins) |
| <10 g/L | residual media/salts |
| <1 g/L | residual sucrose/glucose |
| <2 g/L | "unfermentables" (feedstock/impurities) |

*Balance water

A product concentration of about 5-15% by weight of 1,4-BDO can be achieved through fermentation based biosynthetic production processes.

It is understood that modifications which do not substantially affect the activity of the various embodiments of this invention are also included within the definition of the invention provided herein. Accordingly, the following examples are intended to illustrate but not limit the present invention.

EXAMPLE I

Centrifugation of Fermentation Broth

This example shows the use of a disc-stack centrifuge to remove cell mass and other solids from a fermentation broth.

1,4-Butanediol fermentation broth produced by a genetically modified *E. coli* was clarified via centrifugation. A GEA-Westfalia disc stack centrifuge was used for this step. The lab-scale centrifuge, model CTC 1 Whispefuge, has a bowl capacity of 1.0 liters and a solids holding space of 0.55 liters. The bowl hood, distributor, disc stacks, and all process wetted parts are constructed with high tensile strength stainless steel. The feed to centrifuge unit was controlled using a peristaltic pump, with the flow rate held constant at approximately 0.25 liters per minute. A back pressure of about 15 psi was maintained in the system by throttling a regulating valve on the outlet centrate flow. The centrifuge was operated at 12,000 rpm and the feed was at ambient room temperature. The centrifugation removes cellular biomass and insoluble materials from the fermentation broth. The concentration of cellular biomass and insoluble material is indicated by the turbidity, as measured by optical density (OD) at 600 nm. The turbidity data for feed fermentation broth and clarified centrate is shown in Table 5. The feed was visibly hazy and had a measured OD of 13.3. The clarified centrate was visually much clearer and had a measured OD of 0.18. Overall the turbidity was decreased by approximately 99%, showing excellent clarification by the disc stack centrifuge.

TABLE 5

Turbidity measured by optical density (OD) at 600 nm

|  | OD at 600 nm |
|---|---|
| Feed, Fermentation Broth | 13.3 |
| Clarified Centrate | 0.18 |

EXAMPLE II

Ultrafiltration of Fermentation Broth

This example shows the ultrafiltration of the fermentation broth following removal of cell mass and other solids by centrifugation conducted in Example I.

A GEA lab scale filtration unit, Model L, was used to further clarify the product produced in Example 1. The Model L filtration unit was equipped with Hydranautics 5K PES flat sheet membranes. Total installed membrane area was 0.144 $m^2$. The transmembrane pressure was maintained at approximately 36 psi by adjusting inlet flow and back pressure regulating valve. The temperature of the feed was maintained at approximately 27° C. using an inlet heat exchanger. The permeate flow rate was measured throughout the course of the experiment to determine the flux. Table 6 shows the permeate flux in liters/$m^2$/h as a function of the volumetric concentration factor (VCF).

TABLE 6

Ultrafiltration flux versus VCF

| VCF | Flux liters/$m^2$/h |
|---|---|
| 1.18 | 15.02 |
| 1.44 | 15.37 |
| 1.86 | 15.29 |
| 2.60 | 15.34 |
| 4.33 | 15.06 |
| 6.50 | 14.79 |

Samples were also drawn throughout the experiment to determine the permeate quality. Protein concentration in the feed and permeate was measured using Bradford Assay. Table 7 shows the protein concentration in the feed, permeate and retentate. The protein concentration decreased by approximately 68% in the permeate compared to the feed.

TABLE 7

Protein concentration measured using Bradford Assay

|  | Protein Concentration, mg/L |
|---|---|
| Feed, Centrifuged Broth | 84.09 |
| UF Permeate | 27.11 |
| UF Retentate | 248.90 |

EXAMPLE III

Nanofiltration of Fermentation Broth

This example shows the nanofiltration of the fermentation broth following ultrafiltration conducted in Example II.

A GEA lab scale filtration unit, Model L, was equipped with GE DK nanofiltration flat sheet membranes. Total installed membrane area was 0.072 $m^2$. This set up was used to filter the UF permeate obtained from Example 2. The transmembrane pressure was maintained at approximately 270 psi by adjusting inlet flow and back pressure regulating valve. The temperature of the feed was maintained at 38° C. using an inlet heat exchanger. The permeate flow was measured throughout the course of the experiment to determine the flux. Table 8 shows the flux in liters/$m^2$/h as a function of the volumetric concentration factor (VCF).

TABLE 8

Nanofiltration flux

| VCF | Flux liters/m2/h |
|---|---|
| 1.33 | 14.69 |
| 1.74 | 13.41 |
| 2.50 | 10.42 |

Samples were also drawn throughout the experiment to determine the permeate quality. Organic acids where measured using LC-MS, salt ions where analyzed using Chromatography (IC), and glucose was measured using an Analox G6 analyzer. Table 9 shows the percent rejection for glucose, ions, and organic acids. At the pH of the feed it is expected that the organic acids are present in their salt form. The nanofiltration permeate also had a visual reduction in color from a distinct yellow in the feed to a very faint yellow in the permeate product.

TABLE 9

Percent rejection of glucose, ions and organic acids by nanofiltration

| Glucose | Monovalent Cations | Divalent Cations | Anions | Organic Acids |
|---|---|---|---|---|
| 88.57% | 72.80% | 100.00% | 82.45% | 64.39% |

EXAMPLE IV

Ion Exchange of Fermentation Broth

This example shows the ion exchange chromatographic purification of the fermentation broth following nanofiltration conducted in Example III.

Nanofiltration permeate obtained from Example III was processed through an ion exchange step to remove the remaining ions and further clarify the product. Amberlite IR 120H, a strong acid cation exchange resin, and Amberlite IRA 67, a weak base anion exchange resin, were used for this step. Individual cation and anion exchange columns, 2 ft high×1 inch diameter, were loaded with $5.3 \times 10^{-3}$ ft$^3$ of cation and anion exchange resins, respectively. The nanofiltration permeate was first fed to cation exchange column, and then to anion exchange column at 10 mL/min and 40° C. The ion exchange was analyzed for ion content via IC. All the remaining ions were removed to a concentration of less than 0.1 mEq/L. All the remaining organic acids were also removed in this step. The product was very clear with no visible yellow color.

EXAMPLE V

Evaporative Crystallization of a Synthetic Feed

This example shows the removal of salts from a synthetic feed by evaporative crystallization on laboratory scale with the aid of a rotary evaporator.

Evaporation was performed using a Buchi Rotavap R-205 at bath temperature of 50° C. and a vacuum of ~100 mm of Hg. A synthetic feed material was prepared with about 8% BDO in water containing approximately 92 mEq/L monovalent cations, 5 mEq/L divalent cations and 125 mEq/L anions. The water was evaporated off from this mixture while the salt ions where simultaneously allowed to precipitate from the solution. Ion concentrations in the solution were monitored throughout the evaporation by taking small sample aliquots for analysis by Ion Chromatography. Prior to analysis the precipitated solids were filtered off. Table 10 shows the concentration of ions in solution (normalized to 100% in the feed sample) as the BDO was concentrated from approximately 10 to 95%. The ion concentrations increased up to the saturation point in the solution (at approximately 30% BDO). After this point further evaporation forced crystallization (precipitation) of the salts. Overall, this evaporative crystallization step caused 97.5% of the salt ions to precipitate from the BDO solution.

TABLE 10

Evaporative precipitation of synthetic broth

| Time, h | BDO wt % | % Monoatomic cations | % Diatomic cations | % Anions |
|---|---|---|---|---|
| 0 | 10.00 | 100.00 | 100.00 | 100.00 |
| 0.25 | 15.74 | 159.75 | 132.32 | 161.25 |
| 0.5 | 33.79 | 344.61 | 159.73 | 353.02 |
| 0.75 | 81.32 | 35.49 | 0.00 | 47.24 |
| 1.5 | 94.25 | 22.43 | 0.00 | 20.17 |

EXAMPLE VI

Salt Solubility

This example shows salt solubility profiles in various small carbon chain diols, including 1,4-BDO.

Salt solubility in different solutions containing varying amounts of 1,4-Butanediol (BDO), 1,3-Propanediol (PDO) or 1,2-Ethanediol (mono etheylene glycol, MEG) was measured. The salts were added to 10 mL of the solution until the solution was saturated. The saturated salt solubility was measured using Ion Chromatography. Table 11 shows salt solubility of four different salts at room temperature (approximately 20° C.). The salt solubility decreases significantly with increases in BDO concentration demonstrating the feasibility of salt removal using evaporative crystallization. Table 12 shows salt solubility of three different salts in different concentrations of 1,4-BDO, PDO or MEG solutions at room temperature. The results show a decrease in salt solubilities going from MEG, to PDO, to 1,4-BDO, demonstrating that 1,4-BDO is best suited for an evaporative crystallization among the three compounds.

TABLE 11

Solubility of four different salts in solutions containing 0 to 100% 1,4-Butanediol (1,4-BDO)

| Solution (% 1,4-BDO) | Average Measured Solubility (wt %) ~20 C. | | | |
|---|---|---|---|---|
| | $KH_2PO_4$ | NaCl | $MgSO_4$ | $(NH_4)_2SO_4$ |
| 0 (Water) | 20.101 | 32.300 | 34.354 | 57.375 |
| 33 | 3.296 | 10.803 | 7.346 | 11.639 |
| 80 | 0.056 | 2.529 | 0.035 | 0.173 |
| 90 | 0.011 | 0.314 | 0.015 | 0.022 |
| 95 | 0.005 | 0.314 | 0.028 | 0.008 |
| 98 | 0.031 | 0.175 | 0.011 | 0.005 |
| 100 | 0.003 | 0.050 | 0.009 | 0.004 |

TABLE 12

Solubility of three different salts in 50, 80 or 100% of 1,4-Butanediol (BDO), 1,3-Propanediol (PDO) or 1,2-Ethanediol (MEG)

| Solvent | Solution (% Solvent) | Average Measured Solubility (wt %) ~20 C. | | |
|---|---|---|---|---|
| | | KCl | $Na_2SO_4$ | $(NH_4)H_2PO_4$ |
| BDO | 50 | 8.21 | 0.63 | 2.97 |
| | 80 | 0.94 | 0.04 | 0.16 |
| | 100 | 0.05 | 0.00 | 0.01 |
| PDO | 50 | 8.70 | 2.38 | 3.62 |
| | 80 | 1.45 | 0.10 | 0.46 |
| | 100 | 0.30 | 0.01 | 0.09 |

TABLE 12-continued

Solubility of three different salts in 50, 80 or 100% of 1,4-Butanediol (BDO), 1,3-Propanediol (PDO) or 1,2-Ethanediol (MEG)

| Solvent | Solution (% Solvent) | Average Measured Solubility (wt %) ~20 C. | | |
| --- | --- | --- | --- | --- |
| | | KCl | Na$_2$SO$_4$ | (NH$_4$)H$_2$PO$_4$ |
| MEG | 50 | 14.11 | 9.42 | 8.06 |
| | 80 | 7.72 | 1.81 | 2.90 |
| | 100 | 4.76 | 0.69 | 1.22 |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A process of isolating 1,4-butanediol (1,4-BDO) from a fermentation broth comprising
    separating a liquid fraction enriched in 1,4-BDO from a solid fraction comprising cells, wherein said step of separating said liquid fraction comprises microfiltration;
    removing water from said liquid fraction, wherein removing water is accomplished by evaporation with an evaporator system comprising one or more effects and a mechanical vapor recompressor;
    removing salts from said liquid fraction, wherein salts are removed by nanofiltration and by ion exchange; and
    purifying 1,4-BDO.

2. The process of claim 1, wherein microfiltration comprises filtering through a membrane having pore sizes from about 0.05 microns to about 5.0 microns.

3. The process of claim 1, wherein said step of separating said liquid fraction further comprises ultrafiltration.

4. The process of claim 3, wherein ultrafiltration comprises filtering through a membrane having pore sizes from about 0.005 to about 0.1 microns.

5. The process of claim 1, wherein said evaporator system comprises a double- or triple-effect evaporator.

6. The process of claim 1, wherein said evaporator system comprises an evaporator selected from the group consisting of a falling film evaporator, a short path falling film evaporator, a forced circulation evaporator, a plate evaporator, a circulation evaporator, a fluidized bed evaporator, a rising film evaporator, a counterflow-trickle evaporator, a stirrer evaporator, and a spiral tube evaporator.

7. The process of claim 1, wherein said evaporator system comprises a vacuum.

8. The process of claim 1, wherein substantially all of the salts are removed prior to removal of water.

9. The process of claim 1, wherein substantially all of the salts are removed after removal of a portion of water.

10. The process of claim 1, wherein salts are removed after removal of substantially all of the water.

11. The process of claim 1, wherein nanofiltration comprises filtering through a membrane having a pore size range from about 0.0005 to about 0.005 microns.

12. The process of claim 1, wherein said solid fraction comprising cells is recycled into said fermentation broth.

13. The process of claim 1, wherein said removed water is recycled into said fermentation broth.

14. The process of claim 1, wherein said removed salts are recycled into said fermentation broth.

15. The process of claim 1, wherein said step of purifying 1,4-BDO comprises distillation.

16. A process for producing 1,4-BDO comprising:
    culturing a 1,4-BDO-producing microorganism in a fermentor for a sufficient period of time to produce 1,4-BDO, said 1,4-BDO producing microorganism comprising a microorganism having a 1,4-BDO pathway comprising one or more exogenous genes encoding a 1,4-BDO pathway enzyme and/or one or more gene disruptions;
    isolating 1,4-BDO by a process according to claim 1.

17. The process of claim 1, wherein removing salts by ion exchange comprises removing salts by cation exchange followed by anion exchange.

* * * * *